(12) United States Patent
Sarles et al.

(10) Patent No.: US 10,481,120 B1
(45) Date of Patent: Nov. 19, 2019

(54) DROPLET BASED MEASUREMENT OF SPECIFIC CAPACITANCE AND INTERFACIAL TENSIONS

(71) Applicant: University of Tennessee Research Foundation, Knoxville, TN (US)

(72) Inventors: Stephen Andrew Sarles, Knoxville, TN (US); Graham Jeffrey Taylor, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 364 days.

(21) Appl. No.: 15/230,242

(22) Filed: Aug. 5, 2016

Related U.S. Application Data

(60) Provisional application No. 62/201,716, filed on Aug. 6, 2015.

(51) Int. Cl.
| | | |
|---|---|---|
| *G01N 27/22* | (2006.01) | |
| *G01N 33/483* | (2006.01) | |
| *G01N 33/52* | (2006.01) | |
| *G01N 21/27* | (2006.01) | |
| *C08J 5/00* | (2006.01) | |

(52) U.S. Cl.
CPC ............ *G01N 27/228* (2013.01); *C08J 5/00* (2013.01); *G01N 21/27* (2013.01); *G01N 27/226* (2013.01); *G01N 33/4833* (2013.01); *G01N 33/525* (2013.01); *C08J 2383/12* (2013.01)

(58) Field of Classification Search
CPC .... G01N 27/228; G01N 27/226; G01N 21/27; G01N 33/4833; G01N 33/525; C08J 5/00; C08J 2383/12
See application file for complete search history.

(56) References Cited

U.S. PATENT DOCUMENTS

| 8,268,627 | B2 | 9/2012 | Bayley et al. |
| 8,691,586 | B2 | 4/2014 | Bayley et al. |

FOREIGN PATENT DOCUMENTS

| WO | WO 2009/024775 A1 | 2/2009 |

OTHER PUBLICATIONS

Taylor, Graham J., et al. "Direct in situ measurement of specific capacitance, monolayer tension, and bilayer tension in a droplet interface bilayer." Soft matter 11.38 (Aug. 5, 2015): 7592-7605.*
Edelstein et al., "Advanced methods of microscope control using uManager software," J Biol Methods.; 1(2), p. 1-18 (2014).

(Continued)

*Primary Examiner* — Robert J Eom
(74) *Attorney, Agent, or Firm* — Jenkins, Wilson, Taylor & Hunt, P.A.

(57) ABSTRACT

Disclosed are methods and apparatus for determining the properties of artificial membranes (e.g., artificially prepared lipid bilayers and biomimetic membranes comprising amphiphilic copolymers). Multiple physical properties of the membranes can be determined via a combination of electrical and optical measurements. The optical and electrical measurements can be determined using a single apparatus, which can also be used to prepare the artificial membrane. Methods are also disclosed for determining the effects changes in the composition of the artificial membrane, such as the addition of a drug or a change in lipid content.

26 Claims, 19 Drawing Sheets

(56) References Cited

OTHER PUBLICATIONS

Petelska et al., "The interfacial tension of the lipid membrane formed from lipid-amino acid systems," Cell Biochem. Biophys., 61, p. 289-296 (2011).
A. Fischer et al., "Ultrasensitive detection of protein translocated through toxin pores in droplet-interface bilayers," Proceedings of the National Academy of Sciences, 108, p. 16577-16581 (2011).
Thiam et al., "Adhesive emulsion bilayers under an electric field: from unzipping to fusion," Physical review letters, 107, 068301-1-068301-4 (2011).
Verma et al., "Surface structure-regulated cell membrane penetration by monolayer protected nanoparticles," Nat. Mater., 7, p. 588-595 (2008).
Boreyko et al., "Air-stable droplet interface bilayers on oil-infused surfaces," Proceedings of the National Academy of Sciences, 111, p. 7588-7593, (2014).
Li et al., "Structure of Magainin and Alamethicin in Model Membranes Studied by X-Ray Reflectivity," Biophysical Journal, 91, p. 3285-3300 (2006).
Nardin et al., "Giant Free-Standing ABA Triblock Copolymer Membrane," Langmuir 16, p. 7708-7712 (2000).
Quilliet et al., "Electrowetting: a recent outbreak," Current Opinion in Colloid & Interface Science, 6, p. 34-39 (2001).
Bach et al., "Letter to the editor—Glyceryl Monoleate Black Lipid Membranes Otained from Squalene Solutions," Biophys. J Biophysical Scoiety, vol. 29, p. 183-188, (Jan. 1980).
Needham et al., "Tensions and free energies of formation fo 'solventless' lipid bilayers," Biophys. J., 41, p. 251-257 (1983).
Baykal-Caglar et al., "Preparation of giant unilamellar vesicles from damp ilpid film for better lipid compositional uniformity," Biochimica et Biophysica Acta (BBA)—Biomembranes 1818, p. 2598-2604 (2012).
Mugele et al., "Electrowetting: from basics to applications," Journal of Physics: Condensed Matter, 17, p. R705-R774 (2005).
Barrera et al., "Membrane physical properties inluence transmembrane helix formation,", Proceedings of the National Academy of Sciences, vol. 109, p. 14422-14427 (2012).
Beaucage et al., Symmetric, Isotopic Blends of Poly(dimethylsiloxane), Macromolecules, 29, p. 8349-8356 (1996).
Villar et al., "A tissue-like printed material," Science, 340, p. 48-52 (2013).
Villar et al., "Formation of droplet networks that function in aqueous environments," Nat Nano, 6, p. 803-808 (2011).
Bayley et al., "Droplet interface bilayers," Molecular BioSystems, 4(12), p. 1191-1208 (2008).
Poulos et al., "Electrowetting on dielectric-based microfluidics for integrated lipid bilayer formation and measurement," Applied Physics Letters, 95, p. 013706-1-103706-3 (2009).
Liu et al., "Uncovering molecular mechanisms of electrowetting and saturation with simulations," Physical review letters, 108, p. 216101-1-216101-5 (2012).
Reyes et al., "Effect of the anesthetics benzyl alcohol and chloroform on bilayers made from monolayers," Biophysical journal, 28, p. 259-279 (1979).
Ebihara et al., "Effect of benzyl alcohol on lipid bilayers," Biophysical Journal, 28, p. 185-196 (1979).
Othman et al., "Dielectric constant and refractive index of poly (siloxane-imide) block copolymer," Materials & Design, 32, p. 3173-3182 (2011).
Kučerka et al., "The effect of cholesterol on short- and long-chain monounsaturated lipid bilayers as determined by molecular dynamics simulations and x-ray scattering," Biophysical Journal, 95, p. 2792-2805 (2008).
Alvarez et al., "Voltage-dependent capacitance in lipid bilayers made from monolayers," Biophysical Journal, vol. 21 ,p. 1-17 (1978).
Carney et al., "Dynamic cellular uptake of mixed-monolayer protected nanoparticles," Biointerphases, 7:17 p. 2-9 (2012).
White et al, "A study of lipid bilayer membrane stability using precise measurements of specific capacitance,", Biophysical Journal, 10, p. 1127-1148 (1970).
White et al., "Phase transitions in planar bilayer membranes," Biophysical Journal, 15, p. 95-117 (1975).
Punnamaraju et al., "Voltage control of droplet interface bilayer lipid membrane dimensions," American Chemlcal Society, 27, p. 618-626 (2010)
White et al., "Letter to the editor: voltage dependence of the capacitance and area of black lipid membranes," Biophysical journal, 36, p. 449-453 (1981).
White et al., "Formation of 'solvent-free' black lipid bilayer membranes from glyceryl monooleate dispersed in squalene," Biophysical journal, 23, p. 337-347 (1978).
Hung et al., "The condensing effect of cholesterol in lipid bilayers," Biophysical Journal, 92, p. 3960-3967 (2007).
Suzuki, "Effect of protein, cholesterol, and phyosphatidylglycerol on the surface activity of the lipid-protein complex reconstituted from pug pulmonary surfactant," Journal of lipid research, 23, p. 62-69 (1982).
Wu et al., "X-ray diffraction study of lipid bilayer membranes interacting with amphiphilic helical peptides: diphytanoyl phosphatidylcholine with alamethicin at low concentrations," Biophys. J., 68, p. 2361-23.69 (1995).
Liu et al., "Droplet-based electro-coalescence for probing threshold disjoining pressure," RSC Publishing, Lab on a Chip, 15, 9, p. 2018-2024 (2015).
Clowes et al., "Physical Properties of Lecithin-Cerebroside Bilayers," Biochimica et Biophysica Acta (BBA)—Biomembranes, 249, pp. 301-317 (1971).
Petelska et al., "Interfacial tension of the two-component bilayer lipid membrane modelling of cell membrane," Bioelectrochemistry and Bioenergetics, 46, pp. 199-204 (1998).
Petelska et al., "Interfacial tension of phosphatidylcholine-phosphatidylserine system bilayer lipid membrane," Biophys. Chem., 120, pp. 199-206 (2006).
Petelska, "Interfacial tension of bilayer lipid membranes," Cent. Eur. J. Chem., 10, pp. 16-26 (2012).
Heron et al., "Direct Detection of Membrane Channels from Gels Using Water-in-Oil Droplet Bilayers," Journal of the American Chemical Society, 129, pp. 16042-16047 (2007).
Heron et al., "Simultaneous Measurement of Ionic Current and Fluorescence from Single Protein Pores," Journal of the American Chemical Society, 131, pp. 1652-1653 (2009).
Quinn et al., "Contact Angle Saturation in Electrowetting," The Journal of Physical Chemistry B, 109, pp. 6268-6275 (2005).
Thiam et al., "From Stability to Permeability of Adhesive Emulsion Bilayers," Langmuir, 28, pp. 6291-6298 (2012).
Babakov et al., "Influence of Electric Field on the Capacity of Phospholipid Membranes," Nature, 210, pp. 953-955 (1996).
Hille, "Ion channels of excitable membranes: Current Problems and Biophysical Approaches," Sinauer Sunderland, MA, Biphys. J., pp. 283-294 (2001).
Pope et al., "The influence of n-alkanols and cholesterol on the duration and conductance of gramicidin single channels in monoolein bilayers," Biochimica et Biophysica Acta (BBA)—Biomembranes, 688, pp. 279-283 (1982).
Karolis et al., "Eifferential effects of cholesterol and oxidised-cholesterol in egg lecithin bilayers," Biochimica et Biophysica Acta (BBA)—Biomembranes, 1368, pp. 247-255 (1988).
Leduc et al., "Direct Investigation of Intracellular Presence of Gold Nanoparticles via Photothermal Heterodyne Imaging," ACS Nano, 5, pp. 2587-2592 (2011).
Brooks et al., "Van Der Waals Forces in Oil-Water Systems from the Study of Thin Lipid Films. III. Comparison of Experimental Results with Hamaker Coefficients Calculated from Lifshitz Theory," Proceedings of the Royal Society of London. A. Mathematical and Physical Sciences, 347, pp. 179-194 (1975).
Morton et al., "Tailored polymeric membranes for *Mycobacterium smegmatis* porin A (MspA) based biosensors," Journal of Materials Chemistry B, 3,pp. 5080-5086 (2015).
Wong et al., "Single molecule measurements of channel proteins incorporated into biomimetic polymer membranes," Nanotechnology, 17, pp. 3710-3717 (2006).

(56) References Cited

OTHER PUBLICATIONS

Bamberg et al., "Voltage-induced thickness changes of lipid bilayer membranes and the effect of an electric field on gramicidin a channel formation," Biochimica et Biophysica Acta (BBA)—Biomembranes, 426, pp. 570-580 (1976).
Venkatesan et al., "Adsorption kinetics dictate monolayer self-assembly for both lipid-in and lipid-out approaches to droplet interface bilayer formation," ACS Publication, Langmuir, 31, pp. 12883-12893 (2015).
Taylor et al., "Heating-Enabled Formation of Droplet Interface Bilayers Using *Escherichia coli* Total Lipid Extract," Langmuir, 31, pp. 325-337 (2015).
Taylor et al., "Supporting Information: Heating-Enabled Formation of Droplet Interface Bilayers Using *Escherichia coli* Total Lipid Extract," Bioinspired materials and transduction laboratory, pp. 1-27 (2014).
Valincius et al., "Soluble Amyloid B-Oligomers Affect Dielectric Membrane Properties by Bilayer Insertion and Domain Formation: Implications for Cell Toxicity," Biophysical Journal, 95, pp. 4845-4861 (Nov. 2008).
Genco et al., "Electroporation in symmetric and asymmetric membranes," Biochimica et Biophysica Acta (BBA)—Biomembranes, 1149, pp. 10-18 (1993).
Levin et al., "A Raman spectroscopic study on the effect of cholesterol on lipid packing in diether phosphatidylcholine bilayer dispersions," Biochimica et Biophysica Acta (BBA)—Biomembranes, 820, pp. 40-47 (1985).
Alonzo et al., "Forces of interaction between surfaces bearing looped polymer brushes in good solvent," Soft Matter, 5, pp. 1897-1904 (2009).
Weaver et al., "Theory of electroporation: A review," Bioelectrochemistry and Bioenergetics, 41, pp. 135-160 (1996).
Poulos et al., "Ion channel and toxin measurement using a high throughput lipid membrane platform," Biosensors and Bioelectronics, 24, pp. 1806-1810 (2009).
Dilger, "The thickness of monoolein lipid bilayers as determined from reflectance measurements," Biochimica et Biophysica Acta (BBA)—Biomembranes, 645, pp. 357-363 (1981).
Pan et al., "Effect of cholesterol on structural and mechanical properties of membranes depends on lipid chain saturation," Physical review. E, Statistical, nonlinear, and soft matter physics, 80, 021931:1-021931:12 (2009).
Poulos et al., "Automatable lipid bilayer formation and ion channel measurement using sessile droplets," Journal of Physics: Condensed Matter, 22, 454105, pp. 1-6 (2010).
Elliott et al., "The influence of n-alkanols on the capacity per unit area of planar lipid bilayers," Biochimica et Biophysica Acta (BBA)—Biomembranes, 773, 165-168 (1984).
Thompson et al., "Enhanced Stability and Fluidity in Droplet on Hydrogel Bilayers for Measuring Membrane Protein Diffusion," Nano Lett., 7, 3875-3878 (2007).
Thompson et al., "Enhanced Stability and Fluidity in Droplet on Hydrogel Bilayers for Measuring Membrane Protein Diffusion: Supporting Information," Nano Lett., 7, 1-12 (2007).
Requena et al., "The Lippmann Equation and the Characterization of Black Lipid Films," Journal of Colloid and Interface Science, 51, 315-327 (1975).
Requena et al., "Van Der Waals Forces in Oil-Water Systems from the Study of Thin Lipid Films. II. The Dependence of the Van Der Waals Free Energy of Thinning on Film Composition and Structure," Proceedings of the Royal Society of London. A. Mathematical and Physical Sciences, 347, 161-177 (1975).
Requena et al., "Letter to the editor: Lenses and the compression of black lipid membranes by an electric field," Biophysical Journal, 15, 77-81 (1975).
Requena et al., "Van Der Waals Forces in Oil-Water Systems from the Study of Thin Lipid Films. I. Measurement of the Contact Angle and the Estimation of the Van Der Waals Free Energy of Thinning of Film," Proceedings of the Royal Society of London. A. Mathematical and Physical Sciences, 347, pp. 141-159 (1975).

Gross et al., "Determining Membrane Capacitance by Dynamic Control of Droplet Interface Bilayer Area," Langmuir, 27, pp. 14335-14342 (2011).
Gross et al., "Determining Membrane Capacitance by Dynamic Control of Droplet Interface Bilayer Area: Supplemental Information," Langmuir, 27, pp. 1-5 (2011).
Gross et al., "Dynamic and reversible control of 2D membrane protein concentration in a droplet interface bilayer," Nano Letters, 11, 3324-3328 (2011).
Holden et al., "Functional Bionetworks from Nanoliter Water Droplets," Journal of the American Chemical Society, 129, pp. 8650-8655 (2007).
Naumowicz et al., "Impedance analysis of phosphatidylcholine-cholesterol system in bilayer lipid membranes," Electrochimica Acta, 50, pp. 2155-2161 (2005).
Yanagisawa et al., "Adhesive force between paired microdroplets coated with lipid monolayers," Soft Matter, pp. 5891-5897 (2013).
Malmstadt et al., "Automated Formation of Lipid-Bilayer Membranes in a Microfluidic Device," Nano letters, 6, pp. 1961-1965 (2006).
Stuurman et al., "Computer Control of Microscopes using uManager," NIH Public Access, Curr Protoc Mol Biol., pp. 1-22 (2010).
De Gennes, "Conformations of Polymers Attached to an Interface," Macromolecules, 13, pp. 1069-1075 (1980).
Poulin et al., "Adhesion of Water Droplets in Organic Solvent," Langmuir, 14, 6341-6343 (1998).
Benz et al., "Voltage-induced capacitance relaxation of lipid bilayer membranes: effects of membrane composition," Biochimica et Biophysica Acta (BBA)—Biomembranes, 455, pp. 721-738 (1976).
Benz et al., "Electrical capacity of black lipid films and of lipid bilayers made from monolyers," Biochimica et Biophysica Acta (BBA)—Biomembranes, 394, pp. 323-334 (1975).
Shamai et al., "Water, electricity, and between . . . on electrowetting and its applications," Soft Matter, 4, pp. 38-45 (2008).
Sarles et al., "Regulated attachment method for reconstituting lipid bilayers of prescribed size within flexible substrates," Analytical Chemistry, 82, pp. 959-966 (2010).
Chevalliot et al., "Experimental Validation of the Invariance of Electrowetting Contact Angle Saturation," Journal of Adhesion Science and Technology, 26, pp. 1909-1930 (2012).
White et al., "Capatcitance, area, and thickness variations in thin lipid film," Biochimica et Biophysica Acta (BBA)—Biomembranes, 323, pp. 7-22 (1973).
White, "Temperature-dependent structural changes in planar bilayer membranes solvent 'freeze-out,'" Biochimica et Biophysica Acta (BBA)—Biomembranes, 356, pp. 8-16 (1974).
White, "The lipid bilayer as a 'solvent' for small hydrophobic molecules," Nature, 262, pp. 421-422 (1976).
Punnamaraju et al., "Triggered Release of Molecules across Droplet Interface Bilayer Lipid Membranes Using Photopolymerizable Lipids," Langmuir, 28, pp. 7657-7664 (2012).
Dixit et al., "Droplet Shape Analysis and Permeability Studies in Droplet Lipid Bilayers," Langmuir, 28, pp. 7442-7451 (2012).
Thutupalli et al., "Bilayer membranes in micro-fluidics: from gel emulsions to soft functional devices," Soft Matter, 7, pp. 1312-1320 (2011).
Hanai et al., "The variation of capacitance and conductance of bimolecular lipid membranes with area," Journal of Theoretical Biology, 9, pp. 433-443 (1965).
McIntosh, "The effect of cholesterol on the structure of phosphatidylcholine bilayers," Biochimica et Biophysica Acta (BBA)—Biomembranes, 513, pp. 43-58 (1978).
McIntosh et al., "The organization of n-alkanes in lipid bilayers," Biochimica et Biophysica Acta (BBA)—Biomembranes, 597, pp. 445-463 (1980).
McMullen et al., "Differential scnning calorimetric study of the effect of cholesterol on the thermotropic phase behavior of a homologous series of linear saturated phosphatidycholines," Biochemistry, 32, pp. 516-522 (1993).
Thapliyal et al., "Automated lipid bilayer and ion channel measurement platform," Biosensors and Bioelectronics, 26, pp. 2651-2654 (2011).

(56) References Cited

OTHER PUBLICATIONS

Hwang et al., "Electrical behavior of droplet interface bilayer networks: experimental analysis and modeling," Journal of the American Chemical Society, 129, pp. 11854-11864 (2007).

Hwang et al., "Asymmetric droplet interface bilayers," J. Am. Chem. Soc., 130, pp. 5878-5879 (2008).

Wang et al., "Conrol of self-assembled structure through architecturally and compositionally complex block copolymer surfactant mixtures," Macromolecules, 47, pp. 7138-7150 (2014).

Elani et al., "Vesicle-based artificial cells as chemical microreactors with spatially segregated reaction pathways," Nat Commun, 5, pp. 1-5 (2014).

Elani et al., "Protein synthesis in artificial cells: using compartmentalization for spatial organization in vesicle bioreactors," Physical Chemistry Chemical Physics, 17, pp. 15534-15537 (2015).

* cited by examiner

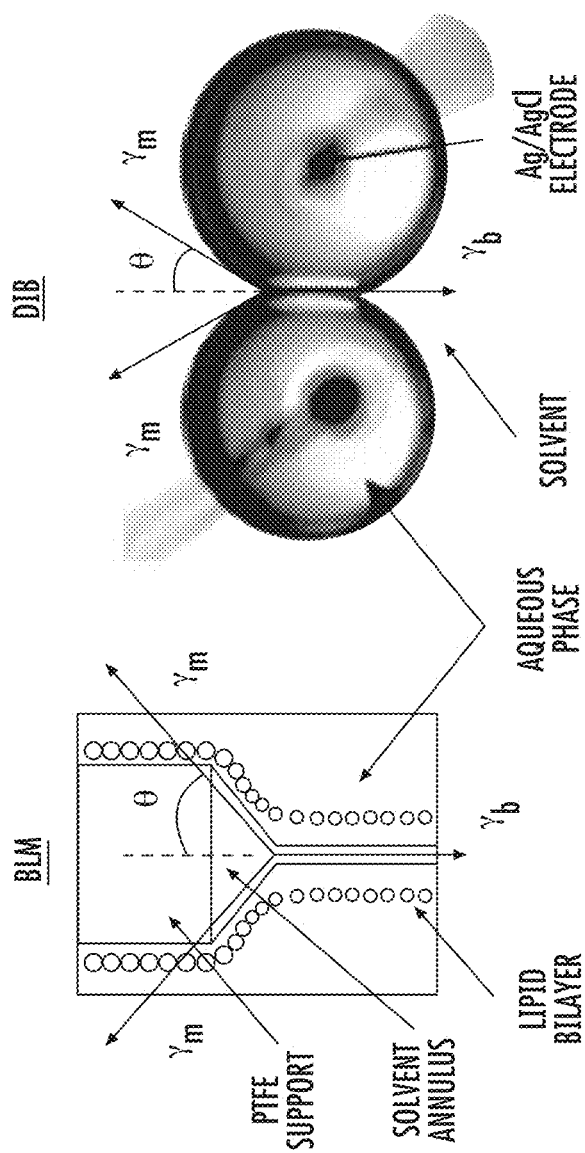

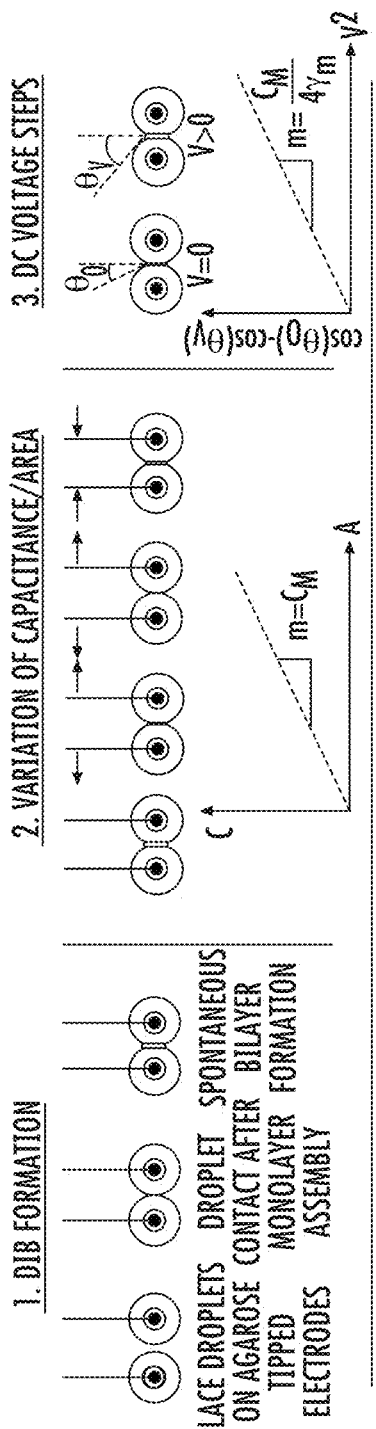
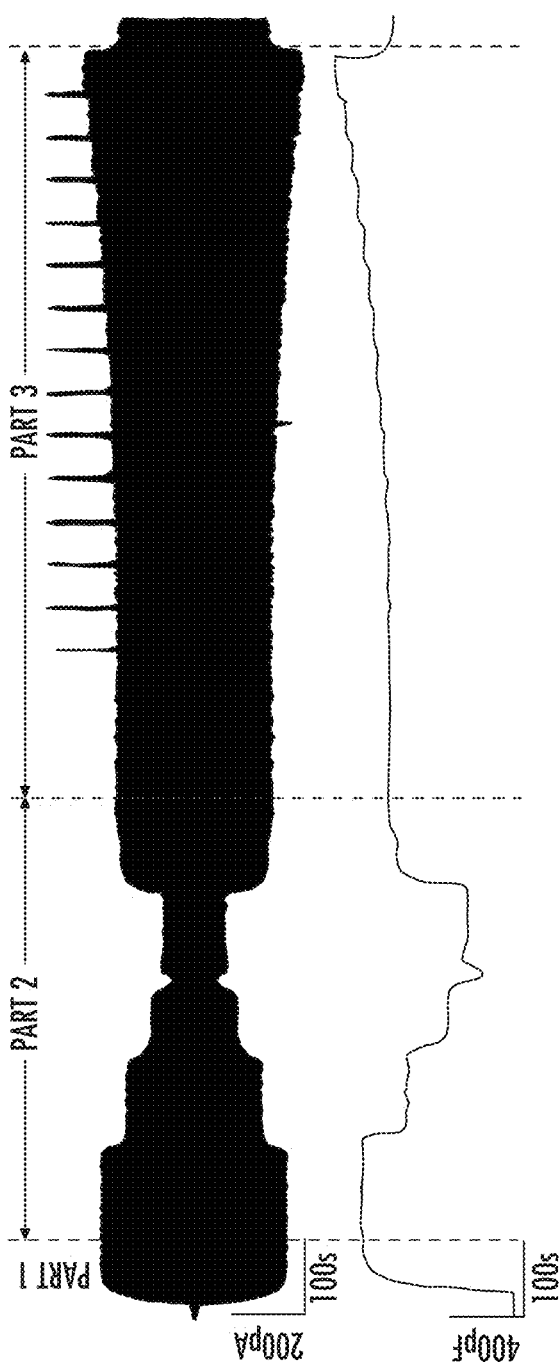
FIG. 3A
FIG. 3B
FIG. 3C

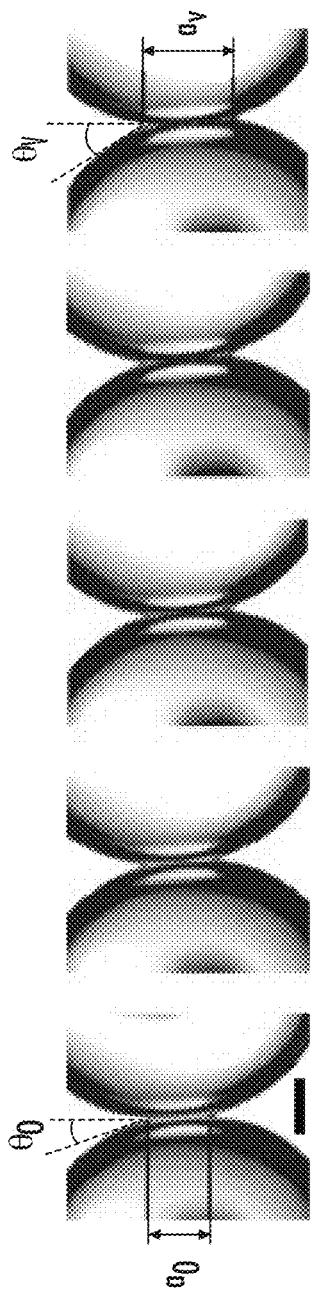
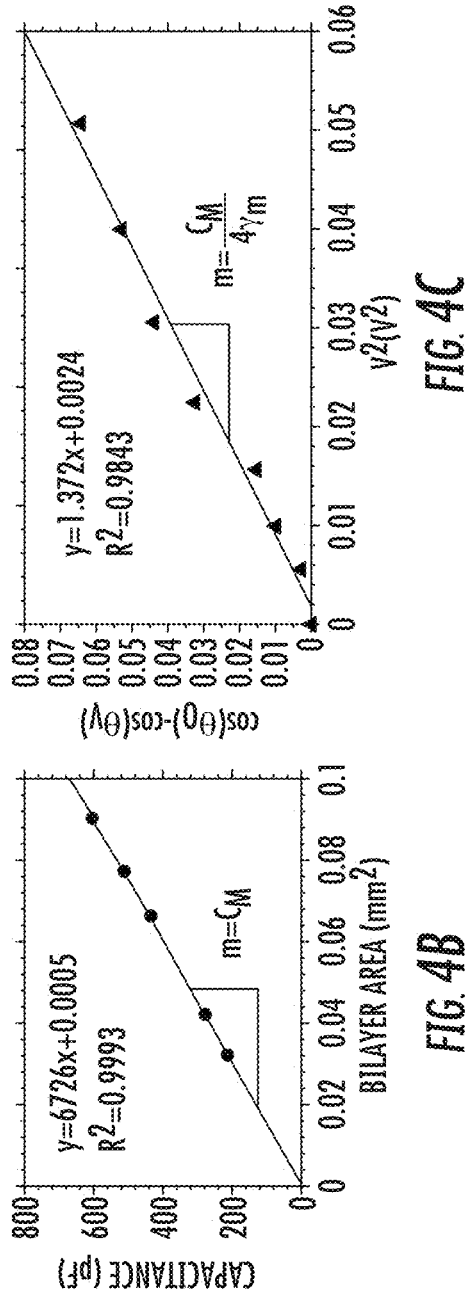
FIG. 4A
FIG. 4B
FIG. 4C

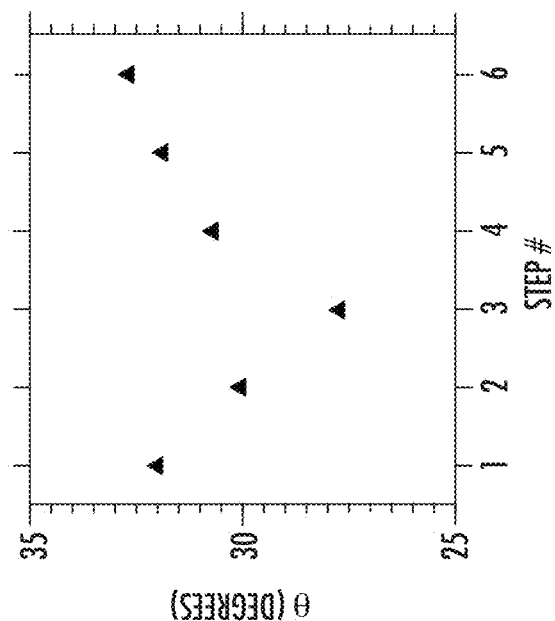
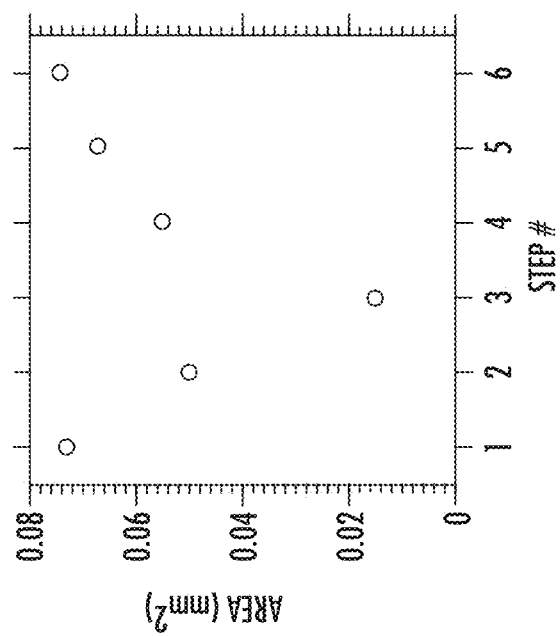
FIG. 9A
FIG. 9B

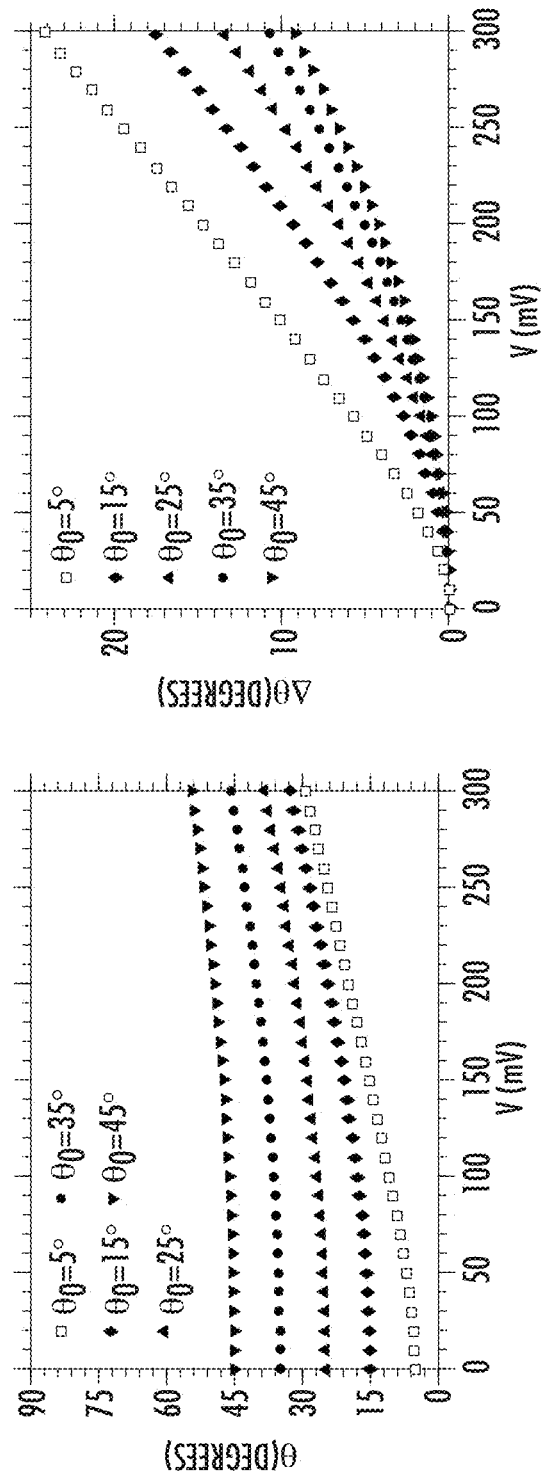

DROPLET BASED MEASUREMENT OF SPECIFIC CAPACITANCE AND INTERFACIAL TENSIONS

RELATED APPLICATIONS

The presently disclosed subject matter claims the benefit of U.S. Provisional Patent Application No. 62/201,716, filed Aug. 6, 2015, the disclosure of which is incorporated herein by reference in its entirety.

STATEMENT OF GOVERNMENT SUPPORT

This invention was made with government support under grant no. FA 9550-12-1-0464 from the United States Air Force Office of Scientific Research. The government has certain rights to this invention.

TECHNICAL FIELD

The presently disclosed subject matter relates generally to assessing thickness and tension in model cell membranes. In some embodiments, the presently disclosed subject matter relates to employing a combination of mechanical manipulation of bilayer area followed by electrowetting of the capacitive interface to examine the sensitivities of bilayer capacitance to area and contact angle to voltage, respectively.

BACKGROUND

Cell membranes are soft materials that play critical roles in physiological processes both by acting as selectively permeable barriers and by providing a two-dimensional, liquid crystalline bilayer in which transmembrane proteins are anchored. The membrane is involved in physiological processes ranging from homeostasis to vesicle trafficking and many other forms of cellular signaling. For these reasons, methods to quantify physical properties of membranes provide direct insight into how their structures impact their functions.

Further, there is increasing evidence that biomacromolecules,[1-3] cell-penetrating peptides[4,5] and nanoparticles,[6-8] and other small molecules such as anesthetics or drugs[9-12] affect the packing and conformations of lipids in the membrane. For example, the bulk hydrophobic region of cholesterol is known to affect the structural order and fluidity of phospholipid bilayers by interdigitating between the acyl chains of neighboring lipids.[13-17] And because the interactions between lipid bilayers and cholesterol, transmembrane proteins, and membrane active pharmaceuticals can alter the tension of the membrane, methods for quantifying membrane tension can be applied to study the uptake and accumulation of a variety of important species into lipid bilayers.[1]

Conditions for studying biological membranes in vivo can be limited by the requirement to keep cells healthy. Thus, artificially prepared models of biological membranes (i.e., biomimetic membranes) are often used to study biological membranes in vitro. However, efforts to determine multiple different physical properties of the same artificial membrane can be difficult due to the need to use different apparatus.

As a consequence, compositions, systems, and methods for determining multiple physical properties of model biological membranes with accuracy and sensitivity are needed. In particular, methods and apparatus to determine multiple properties using the same apparatus or general experimental conditions are needed to make the study of biomimetic membranes more efficient, both with regard to time and expense.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides a method of determining a plurality of physical properties of an artificial cellular membrane, wherein the method comprises: (a) preparing an artificial cellular membrane comprising a bilayer of amphiphilic molecules at an interface between a first droplet and a second droplet, wherein the first and second droplets each comprise an aqueous solution, wherein the first droplet is attached to a first electrode and the second droplet is attached to second electrode, and wherein the first and second droplets are suspended in a hydrophobic liquid medium; (b) determining a specific capacitance of the artificial cellular membrane, wherein the determining comprises determining a nominal capacitance and an artificial cellular membrane area for the artificial cellular membrane at each of a plurality of artificial cellular membrane areas, wherein the area of the artificial cellular membrane is varied by changing the position of the first or second droplet relative to the other of the first or second droplet, and wherein the specific capacitance is calculated from the nominal capacitance and artificial cellular membrane area data, optionally from the slope of a linear least squares regression of nominal capacitance versus area data; and (c) determining an artificial cellular membrane tension, wherein the determining comprises fixing the positions of the first and the second droplets relative to each other, measuring a contact angle between the droplets at a plurality of applied bias voltages, and calculating monolayer tension and bilayer tension.

In some embodiments, the plurality of physical properties comprise specific capacitance, monolayer tension, and bilayer tension. In some embodiments, the method further comprises determining one or more of membrane thickness, free energy of formation, and a parameter that describes electrowetting behavior, optionally alpha, beta, and/or B coefficients.

In some embodiments, the amphiphilic molecules are selected from the group comprising a lipid, an amphiphilic polymer, a biological membrane extract, and a mixture thereof. In some embodiments, the aqueous solution further comprises one or more of the group comprising a small molecule, a peptide, a protein, a biomolecule, and a pharmaceutically active agent.

In some embodiments, the amphiphilic molecules comprise a lipid or lipid mixture selected from the group comprising a fatty acyl, a glycerolipid, a glycerophospholipid, a shingolipid, a sterol lipid, a prenol lipid, a saccharolipid, a polyketide, a phospholipid, a fluorescent lipid, a glycolipid, cholesterol, a biological membrane extract, and a mixture thereof. In some embodiments, the amphiphilic molecules comprise one or more of the group comprising 1,2-diphytanoyl-sn-glycero-3-phosphocholine (DPhPC), 1,2-dioleoyl-sn-glycero-3-phosphocholine (DOPC), palmitoyl oleoyl phosphatidylcholine (POPC), 1-palmitoyl-2-oleoyl-phosphatidylethanolamine (POPE), 1-palmitoyl-2-oleoylphosphatidylglycerol (POPG), 1,2-di-O-phytanyl-sn-glycero-3-phosphocholine (DoPhPC), dipalmitoyl phosphaditdylcholine (DPPC), 1,2-dioleoyl-sn-glycero-3-phosphoglycerol (DOPG), 1,2-distearoyl-sn-glycero-3-phosphocholine (DSPC), diphytanoyl phosphatidylglycerol (DPhPG), diphytanoyl phosphatidylserine (DPhPS), 1,2-dioleoyl-sn-glycero-3-phophoserine (DOPS), 1,2-dipalmitoyl-sn-glycero-3-phosphoserine (DPPS), 1,2-dipalmitoyl-sn-glycero-3-phosphoethanolamine (DPPE), Rhodamine-DPPE, 1,2-dipalmitoyl-sn-glycero-3-phosphoethanolamine-N-(7-nitro-2-1,3-benzoxadiazol-4-yl) (NDB-DPPE), and cholesterol.

In some embodiments, the hydrophobic liquid medium comprises a natural oil, an alkane, an alkene, a fluorocarbon, a silicone oil, a hydrophobic polymer, an amphiphilic polymer, a wax, or a mixture thereof. In some embodiments, the hydrophobic liquid medium is one or more of the group comprising n-hexadecane, heptadecane, tetradecane, squalene, dodecane, silicone oil, decane and mixtures thereof.

In some embodiments, the hydrophobic liquid medium is contained in a transparent chamber, wherein a side of said chamber, optionally a top side of the chamber, is completely or partially open to receive the electrodes, further optionally wherein the transparent chamber comprises or consists of polydimethylsiloxane (PDMS), glass, acrylic or rubber. In some embodiments, a microscope and/or camera is positioned to obtain optical images of the artificial cellular membrane.

In some embodiments, the first electrode and the second electrode are coated with one of the group comprising a hydrogel, agarose, polyacrylamide, nitro-cellulose, cellulose acetate, glass, mesoporous silica, cross-linked polyethylene glycol, a chemically linked layer of biomolecules, proteins, or other species to provide a hydrophilic surface, and a patterned or textured surface created to display a desired wetting property. In some embodiments, the first and second electrode each comprise silver/silver chloride. In some embodiments, at least one of the first and the second electrodes is attached to a micromanipulator. In some embodiments, a three-axis micromanipulator is attached to each of the first electrode and the second electrode, and the positioning of the first and/or second droplets is performed using one or more of the micromanipulators.

In some embodiments, the first and second droplets each have a volume of between about 10 nanoliters (nL) and about 1000 nL, optionally between about 200 nanoliters and about 500 nanoliters. In some embodiments, the first and second droplets each have a volume of about 300 nL.

In some embodiments, the preparing of step (a) comprises: (i) preparing the aqueous solution, wherein the aqueous solution comprises an amphiphilic molecule or mixture of amphiphilic molecules; (ii) attaching the first droplet of the aqueous solution to a tip of the first electrode and attaching the second droplet of the aqueous solution to a tip of the second electrode; (iii) suspending the first and second droplets in the hydrophobic liquid medium; and (iv) moving the first and/or second electrode to position the first and second droplets relative to one another to form an interface between the first and second droplets. In some embodiments, the amphiphilic molecule or mixture of amphiphilic molecules comprises an amphiphilic polymer, optionally an ABA block copolymer, and step (iv) further comprises applying a voltage.

In some embodiments, the determining of a nominal capacitance and an artificial cellular membrane area at each of a plurality of artificial cellular membrane areas in step (b) comprises: (v) moving the first and/or second electrode to change the relative position of the first and second droplets and thus the artificial cellular membrane area; (vi) waiting for the nominal capacitance to stabilize, optionally wherein the waiting is for between about 30 seconds and about 60 seconds; (vii) recording the nominal capacitance and acquiring an optical image of the artificial cellular membrane; (viii) calculating the area of the artificial cellular membrane using data from the optical image; and (ix) repeating steps (v)-(viii) one or more times, optionally four times, prior to calculating the specific capacitance.

In some embodiments, the contact angle between droplets at each of the plurality of applied bias voltages is measured using an optical image of the droplets taken during the application of each of the applied bias voltages. In some embodiments, calculating the monolayer tension comprises determining the slope of a linear least squares regression of a plot of the change in the cosine of the contact angle as a function of voltage squared and using the slope and the specific capacitance determined in step (b) to determine monolayer tension using the Young-Lippmann equation. In some embodiments, calculating the bilayer tension comprises using the Young-Dupre equation.

In some embodiments, the presently disclosed subject matter provides a method of determining the effect of a change in the chemical composition of an artificial cellular membrane, wherein the method comprises: (a) preparing an artificial cellular membrane at an interface between a first droplet and a second droplet of a first aqueous solution wherein the first aqueous solution comprises an amphiphilic molecule or mixture of amphiphilic molecules, and wherein the first droplet and the second droplet are each attached to separate electrodes and suspended in a hydrophobic liquid medium; (b) determining specific capacitance of the artificial cellular membrane, wherein the determining comprises determining a nominal capacitance and an artificial cellular membrane area at each of a plurality of artificial cellular membrane areas, wherein artificial cellular membrane area is varied by changing the position of the first or second droplet relative to the other of the first and second droplets, and optionally wherein the specific capacitance is calculated from the slope of a linear least squares regression of the nominal capacitance versus area data; (c) determining an artificial cellular membrane tension, wherein the determining comprises fixing the positions of the first and the second droplets relative to each other, measuring the contact angle of the droplets at a plurality of applied bias voltages, and calculating the monolayer and bilayer tension; (d) repeating steps (b)-(c) for an artificial membrane formed at the interface of a first and a second droplet of a second aqueous solution, wherein the second aqueous solution comprises an amphiphilic molecule or molecules, and wherein the chemical composition of the second aqueous solution differs from the chemical composition of first aqueous solution, and wherein the first and the second droplet of the second aqueous solution are each attached to separate electrodes and suspended in a hydrophobic liquid medium; and (e) comparing the data obtained in for the artificial cellular membrane formed with droplets of the first aqueous solution to that obtained for the artificial membrane formed with droplets of the second aqueous solution, thereby determining the effect of a change in chemical composition of the artificial cellular membrane.

In some embodiments, the second aqueous solution comprises a small molecule, peptide, protein, biomolecule, or pharmaceutically active agent that may or may not be present in the first aqueous solution, and wherein the method determines the effect of the small molecule, peptide, protein, biomolecule, or pharmaceutically active agent on the artificial cellular membrane. In some embodiments, the second aqueous solution comprises a small molecule or pharmaceutically active agent, wherein the pharmaceutically active agent is an anesthetic or model anesthetic, optionally lidocaine or ethanol.

In some embodiments, the presently disclosed subject matter provides an apparatus for determining a plurality of physical properties of an artificial cellular membrane, said apparatus comprising: a first and a second electrode, wherein the first and the second electrode each comprise a coated tip, wherein the coated tip comprises an amphiphilic or hydrophilic material, optionally agarose; a transparent chamber for holding a hydrophobic liquid medium, wherein the transparent chamber is at least partially open on a side of the chamber; a waveform generator in electrical communication with the first and the second electrodes; an amplifier and a data acquisition system, for collecting electrical data; and a camera positioned for imaging the transparent vessel. In some embodiments, one or both of the first and the second electrodes are attached to a micromanipulator, optionally wherein each of first and the second electrodes are attached to a separate three-axis micromanipulator.

In some embodiments, the presently disclosed subject matter provides a method of determining a plurality of physical properties of an artificial cellular membrane, wherein the plurality of physical properties include at least specific capacitance, monolayer tension, and bilayer tension, wherein the method comprises: forming and obtaining electrical measurements and optical images of an artificial cellular membrane using an apparatus comprising a first and a second electrode, wherein the first and the second electrode each comprise a coated tip, wherein the coated tip comprises an amphiphilic or hydrophilic material, optionally agarose; a transparent chamber for holding a hydrophobic liquid medium, and wherein the transparent chamber is at least partially open on a side of the chamber; a waveform generator in electrical communication with the first and the second electrodes; an amplifier and a data acquisition system, for collecting electrical data; and a camera positioned for imaging the transparent vessel; and calculating values for the plurality of physical properties from the data obtained using the apparatus.

In some embodiments, the presently disclosed subject matter provides a method of forming an artificial cellular membrane comprising an amphiphilic block copolymers, wherein the method comprises: (a) preparing an aqueous solution comprising an amphiphilic block copolymer, optionally wherein the amphiphilic block copolymer is an ABA block copolymer comprising hydrophilic A blocks and a hydrophobic B block; (b) attaching a first droplet of the aqueous solution to a tip of a first electrode and attaching a second droplet of the aqueous solution to a tip of a second electrode; (c) suspending the first and second droplets in a hydrophobic liquid medium; (d) moving the first and/or second electrode to position the first and second droplets in physical contact with one another; and (e) applying a voltage, thereby forming the artificial cellular membrane, wherein the artificial cellular membrane comprises a copolymer-stabilized interface (CSI) between the first and the second droplets.

In some embodiments, the amphiphilic copolymer is an ABA block copolymer comprising poly(ethylene oxide) (PEO) A blocks and a polydimethylsiloxane (PDMS) B block. In some embodiments, the hydrophobic liquid medium comprises a mixture of a hydrophobic solvent and an amphiphilic copolymer, optionally an ABA block copolymer. In some embodiments, the method further comprises characterizing the artificial cellular membrane via electrical measurements and/or optical imaging.

In some embodiments, the presently disclosed subject matter provides an artificial cellular membrane comprising a copolymer stabilized interface (CSI) between a polymer-coated first droplet of an aqueous solution and a polymer-coated second droplet of an aqueous solution. In some embodiments, the artificial cellular membrane comprises an ABA block copolymer, optionally block copolymer comprising poly(ethylene oxide) (PEO) A blocks and a polydimethylsiloxane (PDMS) B block.

Accordingly, it is an object of the presently disclosed subject matter to provide new methods and apparatus for determining the physical properties of artificial cellular membranes. These objects and other objects are achieved in whole or in part by the presently disclosed subject matter.

An object of the presently disclosed subject matter having been stated hereinabove, and which is achieved in whole or in part by the presently disclosed subject matter, other objects will become evident as the description proceeds when taken in connection with the accompanying drawings and examples as best described hereinbelow.

BRIEF DESCRIPTION OF THE DRAWINGS

FIGS. 2A and 2B are schematic illustrations showing common model membranes include the black lipid membrane (FIG. 2A) and the droplet interface bilayer (FIG. 2B). In both cases, the tension of the lipid bilayer that forms is in equilibrium with the vertical sum of the two opposing monolayer tensions.

FIG. 3A is schematic illustration showing a representative three-part process used to characterize DIBs in accordance with the presently disclosed subject matter: Part 1 represents bilayer formation; Part 2 represents the mechanical tuning of the bilayer area to determine specific capacitance; and Part 3 represents electrical tuning of the contact angle to determine monolayer tension via the Young-Lippmann equation (eqn (3)).

FIG. 3B is a typical current trace recorded during the course of an experiment in which all three parts shown in FIG. 3A are performed.

FIG. 3C is a plot of membrane capacitance versus time computed from the raw square current waveform shown in FIG. 3B.

FIG. 4A is a set of representative images of a DPhPC DIB in decane during a Young-Lippmann test for monolayer and bilayer tensions (bottom-view images, scale bar represents 100 mm). The DIB is allowed to equilibrate at each voltage before capturing any images used for contact angle measurements. The contact angle and the contact area increase with increasing voltage. This behavior is a result of reduction in bilayer surface tension by an amount equal to the energy stored on the capacitor.

FIG. 4B is a plot showing results from specific capacitance measurement (V=0 mV, Part 2 in FIGS. 3A-3C).

FIG. 4C is a plot based on the Young-Lippmann equation, which describes the linear relationship between applied bias voltage and the resulting change in the cosine of the contact angle. Experimental observation of the contact angle at various applied voltages then allows for calculation of the monolayer tension. FIGS. 4B and 4C represent data obtained from a DPhPC DIB in hexadecane.

FIGS. 9A and 9B are plots showing, respectively, area and contact angle at each step during Part 2 of the DPhPC DIB experiment shown in FIGS. 6A-6B. With each step, area is either decreased or increased by changing the distance between electrodes. Generally, contact angle is seen to increase with increasing bilayer area and vice versa.

FIG. 10A is a plot showing theoretical contact angle predicted by the Young-Lippmann equation for various hypothetical zero-volt contact angles ($\theta_0$) (5°, squares; 15°, diamonds; 25°, upward-pointing triangles; 35°, circles; and 45°, downward-pointing triangles) with a DPhPC DIB formed in hexadecane ($C_M$=0.65 µF/cm$^2$, $\gamma_m$, =1.18 mN/m). The simulated input voltage is linearly varied across the range from 0-300 mV.

FIG. 10B is a plot of data in FIG. 10A converted to show the change in contact angle (Δθ) with increasing applied voltage. Data for various hypothetical zero-volt contact angles ($\theta_0$) is shown (5°, squares; 15°, diamonds; 25°, upward-pointing triangles; 35°, circles; and 45°, downward-pointing triangles).

(FIG. 18C) Monolayer tensions, (FIG. 18D) contact angles at the threshold voltage, and (FIG. 18E) computed average membrane tensions for a DPhPC DIB in hexadecane and for all CSIs.

DETAILED DESCRIPTION

Figure 1:
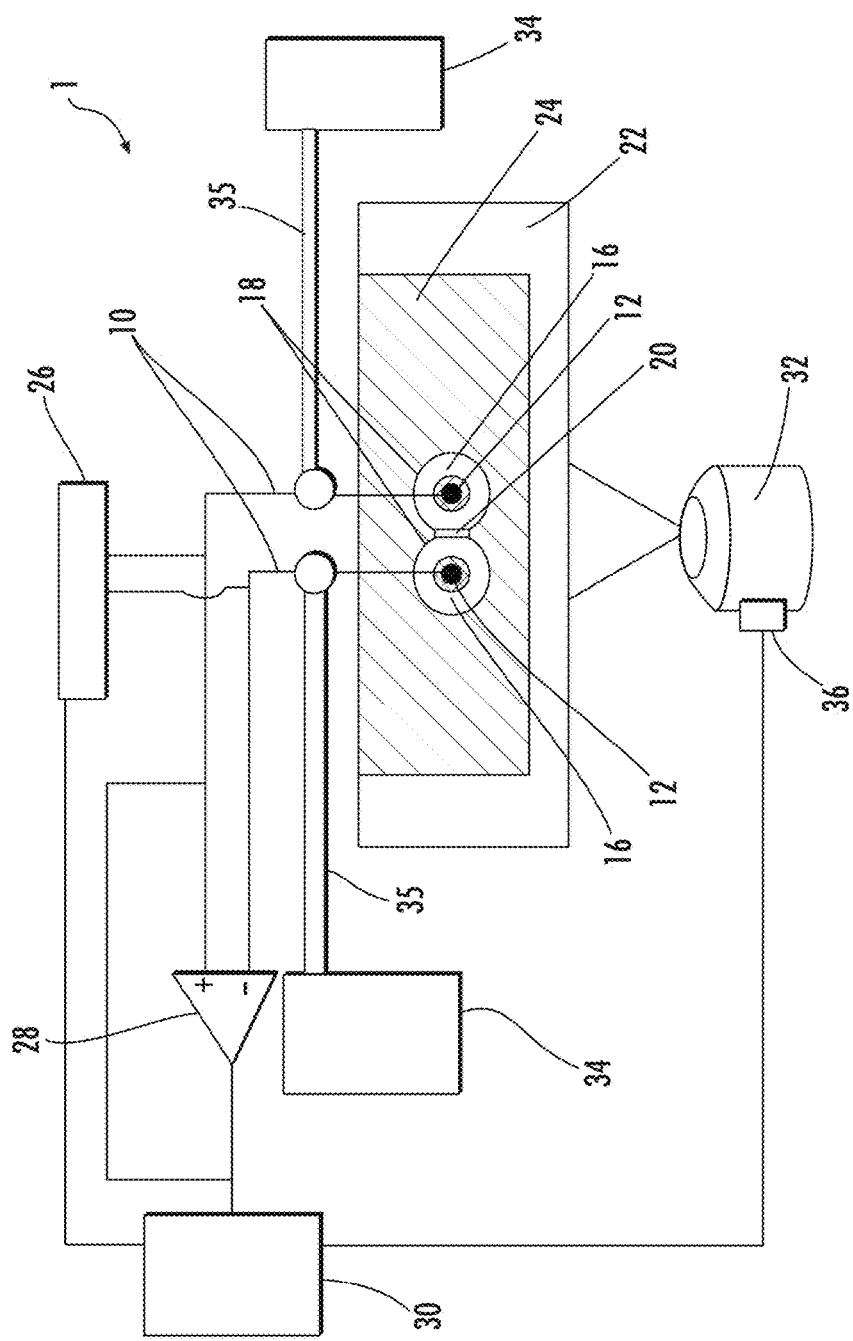
FIG. 1 is a schematic drawing showing an exemplary apparatus of the presently disclosed subject matter for use in forming artificial cellular membranes and collecting electrical and optical data to determine physical properties of the membranes.

Thickness and tension are important physical parameters of model cell membranes. However, traditional methods to measure these quantities require multiple experiments using separate equipment. The presently disclosed subject matter provides in some embodiments a new multi-step procedure for directly accessing in situ multiple physical properties of droplet interface bilayers (DIB), including specific capacitance (related to thickness), lipid monolayer tension in the Plateau-Gibbs border, and bilayer tension. In some embodiments, the presently disclosed subject matter employs a combination of mechanical manipulation of bilayer area followed by electrowetting of the capacitive interface to examine the sensitivities of bilayer capacitance to area and contact angle to voltage, respectively. These data allow for determining the specific capacitance of the membrane and surface tension of the lipid monolayer, which are then used to compute bilayer thickness and tension, respectively. The use of DIBs affords accurate optical imaging of the connected droplets in addition to electrical measurements of bilayer capacitance, and it allows for reversibly varying bilayer area. The data obtained also allows for calculation of the free energy of adhesion, or free energy of formation, for the interface.

In one particular example, the accuracy of a technique of the presently disclosed subject matter was validated with diphytanoyl phosphatidylcholine (DPhPC) DIBs in hexadecane. In another particular example, a method in accordance with the presently disclosed subject matter was applied to quantify separately the effects on membrane thickness and tension caused by varying the solvent in which the DIB is formed and introducing cholesterol into the bilayer. The presently disclosed subject matter employs capacitance measurements and optical images to determine both thickness and tension and thus is particularly well-suited for studying the effects of peptides, biomolecules, natural and synthetic nanoparticles, and other species that accumulate within membranes without altering bilayer conductance.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a solvent" includes a plurality or mixture of solvents, and so forth.

Unless otherwise indicated, all numbers expressing quantities of size, weight, percentage, temperature or other reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size, weight, concentration, temperature, percentage, or the like is meant to encompass variations of, in some embodiments±20%, in some embodiments±10%, in some embodiments±5%, in some embodiments±1%, and in some embodiments±0.1% from the specified amount, as such variations are appropriate to perform the disclosed methods.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" can mean at least a second or more.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

The terms "artificial membrane", "artificial cellular membrane" and "model cell membrane" as used herein refer to a biomimetic membrane that is not present in a living plant or animal cell. In some embodiments, the artificial membrane can comprise a planar, annular or semi-annular structure with two outer surfaces and an inner layer, having hydrophilic surface groups on at least one outer surface or a hydrophilic surface layer on one or both outer surface and a hydrophobic interior layer. Thus, in some embodiments, the membrane can be, for example, an artificially created lipid bilayer or other artificially created bilayer of two monolayers of amphiphilic molecules, wherein hydrophilic groups of one layer of lipid or other amphiphilic molecule are oriented toward one outer surface of the bilayer, hydrophilic groups of another layer of lipid or other amphiphilic molecule are oriented toward the other outer surface of the bilayer, and hydrophobic groups of the lipid or other amphiphilic molecule of both monolayers are oriented in the interior of the bilayer. In some embodiments, the artificial membrane is a copolymer-stabilized interface (CSI) formed between the polymer coatings of aqueous droplets coated with an amphiphilic polymer, such as a block copolymer comprising hydrophobic and hydrophilic blocks (e.g., an AB diblock copolymer). In some embodiments, the block copolymer is an ABA or ABC triblock copolymer comprising a hydrophobic middle B block and hydrophilic outer blocks.

The terms "polymer" and "polymeric" refer to chemical structures that have repeating units (i.e., multiple copies of a given chemical substructure). Polymers can be formed from polymerizable monomers. A polymerizable monomer is a molecule that comprises one or more reactive moieties that can react to form bonds (e.g., covalent bonds) with reactive moieties on other molecules of polymerizable monomer. Generally, each polymerizable monomer molecule can bond to two or more other molecules. In some cases, a polymerizable monomer will bond to only one other molecule, forming a terminus of the polymeric material. In some embodiments, the term "polymer" refers to a molecule with at least 10, at least 20, at least 50, at least 100, at least 1,000, at least 5,000, at least 10,000, or at least 100,000 repeating units. The term "oligomer" can refer to a molecule with a small plurality (e.g., 2, 3, 4, 5, 6, 7, 8, 9, or 10) of repetitive units derived from a monomer or monomers.

A "copolymer" refers to a polymer derived from more than one species of monomer.

As used herein, a "block macromolecule" refers to a macromolecule that comprises blocks in a linear sequence. A "block" refers to a portion of a macromolecule that has at least one feature that is not present in the adjacent portions of the macromolecule. A "block copolymer" refers to a copolymer in which adjacent blocks are constitutionally different, i.e., each of these blocks comprises constitutional units derived from different characteristic species of monomer or with different composition or sequence distribution of constitutional units.

For example, a diblock copolymer of poly(ethylene oxide) and polyethylene is referred to as poly(ethylene oxide)-block-polyethylene. Such a copolymer is referred to generically as an "AB block copolymer" because it contains two types of polymer, i.e., an A block and a B block. Likewise, a triblock copolymer can be represented as "ABA." Other types of block polymers exist, such as multiblock copolymers of the $(AB)_n$ type, ABC block polymers comprising three different blocks, and star block polymers, which have a central point with three or more arms, each of which is in the form of a block copolymer, usually of the AB type.

The term "hydrophilic" can refer to a molecule or species that has an ability to interact with (e.g., dissolve in) water. The terms "hydrophilic polymer" and "hydrophilic polymer block" as used herein generally refers to hydrophilic organic polymers, such as but not limited to, polyvinylpyrrolidone, polyvinylmethylether, polymethyloxazoline (PMOXA), polyethyloxazoline, polyhydroxypropyloxazoline, polyhydroxypropylmethacrylamide, polymethyacrylamide, polydimethylacrylamide, polyhydroxylpropylmethacrylate, polyhydroxyethylacrylate, hydroxymethylcellulose, hydroxyethylcellulose, polyethylenimine (PEI), polyethyleneglycol (i.e., PEG, which can also be referred to as poly(ethylene oxide) or (PEO)) or another hydrophilic poly(alkyleneoxide), polyglycerine, and polyaspartamide. Thus, hydrophilic polymers typically have groups that are polar or that can hydrogen bond to water.

The term "hydrophobic" refers to molecule or species that has a lack of ability to interact with water. Thus, hydrophobic molecules or species typically are relatively non-polar and/or lack groups (e.g., —COOH, —NH$_2$, —NH$_3^+$) that are charged or that can ionize. The terms "hydrophobic polymer" and "hydrophobic polymer block" can refer to polymers, such as, but not limited to, polyolefins (e.g., polyethylene, polypropylene, polybutadiene, etc.), polyvinyls (e.g., polystyrenesor polyvinyl chloride), polydimethylsiloxane, polyethers, nylons (e.g., nylon 66), polycarbonate, polymethylmethacrylate, and polytetrafluoroethylene.

The term "amphiphilic" refers to a molecule or species that has both hydrophilic and hydrophobic groups or regions.

The term "lipid" can refer to a hydrophobic or amphiphilic small molecule, such as, but not limited to a fatty acid, a phospholipid, a glycerolipid, a glycerophospholipid, a sphingolipid, a saccharolipid, or a polyketide. The term lipid can refer to natural or synthetic lipids. The term lipid can also refer to lipids attached to detectable moieties, such as lipids labeled with fluorescent moieties (e.g., Rhodamine, etc.)

The term "lipid bilayer" refers to a flat or annular bilayer of lipid molecules wherein the hydrophilic regions or groups of the amphiphilic molecules are positioned on the outer surfaces of the bilayer and the hydrophobic groups regions or groups of the amphiphilic molecules are located in the interior of the bilayer, thus providing a hydrophobic interior region.

The term "small molecule" as used herein can refer to a chemical compound with a mass of less than about 1000 Daltons, less than about 750 Daltons, less than about 700 Daltons, less than about 650 Daltons, less than about 600 Daltons, less than about 550 Daltons, or less than about 500 Daltons. The small molecule can be a naturally occurring small molecule or a synthetic small molecule. In some embodiments, the small molecule can be biologically active. In some embodiments, the small molecule can be hydrophobic or amphiphilic.

The term "pharmaceutically active agent" as used herein can refer to any molecule or used to treat, cure, diagnose, or prevent a disease or other medical condition (e.g., a cut or a broken bone) in a human or animal subject and/or that is typically used in a medical or veterinary setting to provide an physiological effect in a human or animal subject. The pharmaceutically active agent can be, for example, but is not limited to, an anti-infective agent (e.g., an antifungal, an anti-tubercular, an antiprotozoal, an alcohol or phenol, an oxidizing agent, etc.), a sulfonamide, a folate reductase inhibitor, a sulfone, an antimalarial, an antibacterial (e.g., a β-lactam antibiotic, a tetracycline, a macrolide, an antibacterial polypeptide), an antiviral, a antineoplastic, a central nervous system depressant (e.g., a general anesthetic, an sedative, a hypnotic, an antipsychotic, an anticonvulsant, an antiepileptic), a central nervous system stimulant (e.g., a analeptic, a methylxanthine, a psychomotor stimulant, a monoamine oxidase inhibitor, a tricyclic antidepressant, a psychedelic), an adrenergic agent (e.g., an adrenergic neurotransmitter, an adrenergic receptor antagonist, a sympathomimetic agent), a cholinergic agonist, a cholinergic receptor antagonist, a cholinergic blocking agent, a ganglionic blocking agent, a neuromuscular blocking agent, a alkaloid, a diuretic, (e.g., a carbonic anhydrase inhibitor, a thiazide, a loop diuretic, a potassium-sparing diuretic), a cardiovascular agent (e.g., a antianginal, a vasodilator, an antiarrhythmic, an antihypertensive, an antihyperlipidemic, an anticoagulant, an thyroid hormone), a local anesthetic agent, an antihistamine, histamine, an analgesic (e.g., morphine, an antitussive), a steroid (e.g., estrogen, an adrenal cortex hormone, a progestin, an androgen, a gonadotropin, a cardiac steroid), an eicosanoid (e.g., a prostaglandin or a leukotriene), a carbohydrate, an amino acid, a protein, an enzyme, a peptide hormone, a vitamin (e.g., a lipid soluble vitamin, such as a vitamin A, D, E, or K), or a water soluble vitamin. Other agents include, but are not limited to diagnostic agents, including small molecule and nanoparticle diagnostic agents.

As used herein, the term "polypeptide" means any polymer comprising any of the 20 natural protein amino acids or synthetic or modified amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted.

The terms "hydrophobic liquid medium" and "solvent" as used herein can refer to a hydrophobic liquid or mixture of hydrophobic liquids, such as, but not limited to hydrocarbons (e.g., straight chain or branched alkanes and alkenes having 5 to 30 carbon atoms, or 10 to 17 carbon atoms), natural oils (e.g., vegetable oil, olive oil, etc.) neutral lipids (e.g., triolein, monoolein, etc.) fluorocarbons, and silicone oils (i.e. polymerized siloxanes or "polysiloxanes"). In some embodiments, the hydrophobic medium can also include waxes. Suitable alkanes or alkenes include, but are not limited to alkanes and alkenes with five to 30 carbon atoms, for example, hexadecane, dodecane, tetradecane, heptadecane, decane, pentane or squalene. In some embodiments, the hydrophobic liquid medium could be or could include another non-polar organic solvent, e.g., carbon tetrachloride. In some embodiments, the terms "hydrophobic liquid medium", "solvent" and "oil" are used interchangeably. In some embodiments, the hydrophobic liquid medium can further include a hydrophobic or amphiphilic polymer or another amphiphilic or hydrophobic molecule, such as a pharmaceutically active agent or a lipid. The term "siloxane" refers to a compound comprising a —Si—O—Si— linkage. The term "poly(siloxane)" as used herein refers to a polymeric group or compound of the formula $R_2SiO$, wherein R is H, alkyl, aralkyl (e.g., benzyl), or aryl.

The term "aqueous solution" refers to a solution comprising water. The aqueous solutions describe herein typically include at least one lipid or other amphiphilic molecule that can form a monolayer coating on a droplet of the aqueous solution. However, in some embodiments, the aqueous solution is free of amphiphilic molecules and/or lipids and the amphiphilic and/or lipid molecules that can form a monolayer on the surface of droplets of the aqueous solution are present in hydrophobic liquid medium into which the droplets of aqueous solution are suspended. In some embodiments, both the aqueous solution used to form droplets and the hydrophobic liquid medium contain amphiphilic and/or lipid molecules that can be present in a monolayer that can form on the surface of a droplet of the aqueous solution suspended in the hydrophobic liquid medium.

In any of the embodiments described herein, the aqueous solution can also include additional solutes, such as, but not limited to salts (e.g., NaCl, KCl, $MgCl_2$, etc.) and buffering agents (e.g., Bis-tris, Tris, Hepes, sodium phosphate, potassium phosphate, and the like). Other solutes can include hydrophilic polymers, sugars, denaturants (e.g., urea or guanidine HCl), and pharmaceutically active agents.

The term "droplet" as used herein refers to a volume of a hydrophilic body, which can be a liquid, semi-liquid, or solid body. Droplets are bodies upon which amphiphilic molecules can self-assemble into a monolayer when the droplet is placed in a hydrophobic medium and amphiphilic molecules are present (i.e., in either or both of the hydrophilic body and the hydrophobic medium). In some embodiments, the droplet can have a volume of about 10, 20, 30, 40, 50, 60, 70, 80, 90, 100, 125, 150, 175, 200, 225, 250, 275, 300, 325, 350, 375, 400, 425, 450, 475, 500, 525, 550, 575, 600, 650, 700, 750, 800, 850, 900, 950, or 1000 nL. In some embodiments, the droplet can be larger, e.g., between about 1 microliter (μL) and about 10 μL. Generally, "droplet" refers to a liquid droplet. For example, in some embodiments, the term "droplet" refers to a volume (e.g., between about 10 nL and about 1000 nL, or between about 200 nL and about 500 nL) of an aqueous solution comprising an outer monolayer coating of a lipid or other amphiphilic molecule. In some embodiments, the droplet can be generally spherical. However, in some embodiments, the spherical shape can be distorted such that the droplet can be wider at the bottom, thus having more of a pear or tear shape. In some embodiments, a hydrophilic non-liquid body (e.g., a hydrogel) can take the place of a liquid droplet (e.g., can take the place of a liquid droplet comprising an aqueous solution). Thus, in some embodiments, the droplet is a hydrogel coated with a lipid or amphiphilic molecule or polymer.

The term "artificial cellular membrane area" can refer to the interfacial area formed between two droplets, e.g., wherein a lipid bilayer is present.

The term "suspended" as used herein refers to the positioning of droplets in a liquid medium, wherein the droplet is not in contact with the interface of the liquid medium and air or with the interface of the liquid medium and the transparent vessel/substrate holding the liquid medium.

The terms "forming an interface", "creating an interface" and variants thereof as used herein can refer to positioning two droplets or other hydrophilic bodies relative to one another is such a way that the coatings of the droplets interact (e.g., to form a lipid bilayer). The positioning can involve actual physical contact between droplets or bringing the droplets into sufficiently close proximity that an interface (e.g., a lipid bilayer) forms. In some embodiments, the terms can further include applying a voltage.

II. General Considerations

As described hereinabove, the study of cell membrane properties can provide important information with regard to physiological processes. Synthetic biomimetic membranes can be used to study cell membrane properties in vitro.

Methods exist for measuring tension in synthetic model membranes known as lipid bilayers or black lipid membranes (BLM).[18-20] In many of these studies, the lipid bilayer was formed by spreading a lipid-oil mixture across a small aperture in a hydrophobic solid support submerged in water.[18,20] As illustrated in FIG. 2A, the suspended BLM includes a thinned bilayer region of the painted film, which is stabilized at its perimeter by an annulus of excess solvent. It is well known that the bilayer region and the annulus reach mechanical equilibrium through a balance of surface tensions, obeying Young's equation[21-24]:

$$\gamma_b = 2\gamma_m \cos\theta. \quad\text{Equation 1}$$

Specifically, the interfacial bilayer tension ($\gamma_b$) is balanced by the two lipid monolayer tensions ($\gamma_m$) at the annulus-water interface oriented away from the plane of the membrane by the contact angle ($\theta$). Knowledge of the contact angle and monolayer tension allows for direct calculation of bilayer tension via the Young equation as well as the specific free energy of bilayer adhesion (also known as free energy of formation, $\Delta F$)[18, 21-23, 25].

$$\Delta F = 2\gamma_m(1-\cos\theta). \quad\text{Equation 2}$$

Given a number of established methods for measuring monolayer tension (e.g. drop volume, pendant drop, Wilhelmy plate, etc.), the most difficult aspect of determining bilayer tension in a suspended BLM is obtaining an accurate measurement of the contact angle at the annulus.

Requena, Needham, and Haydon[18,20] developed specialized techniques to measure the contact angle of suspended BLMs such that they could combine them with monolayer tension values obtained from separate drop volume experiments to calculate the interfacial tensions of glycerol monooleate and phospholipid bilayers.[18,20] Via their technique, BLM contact angle measurements are made after introducing a lens of excess solvent into thinned lipid bilayer. Requena and Haydon's measurements of contact angle relied on imaging the concentric fringe patterns (visible rings created by constructive and destructive interference) cast by transmitted light passing through the solvent lens,[20] while Needham and Haydon imaged the lens directly to compute y from the geometric relationship between the radius and volume of the lens.[18] In both cases, bilayer tension was computed using Young's equation by combining contact angles measured in situ with monolayer tension values obtained a priori via the drop-volume method. The approach is sufficiently quantitative; however, separate equipment and multiple experiments are required to determine monolayer and bilayer tensions. A method that provides simultaneous access to both monolayer tension and contact angle would thus enable in situ measurement of lipid bilayer tension and determination of free energy of formation.

Petelska et al. presented a different approach for measuring BLM tension, which they used to study the effects of cholesterol,[1,26] charged lipids,[2] pH,[19] and the presence of amino acids on the tension state in membranes.[19] Petelska's method of bilayer tension measurement involves forming a planar bilayer and applying a differential hydrostatic pressure across the membrane, such that the Young-Laplace equation ($\Delta P = 2\gamma_b/R$) could be used to determine bilayer tension from the radius of curvature of the bulging bilayer.[19] The Young-Laplace equation relates the pressure differential to the radius and tension of the bilayer only. Thus, one drawback of this technique is that it does not allow for direct determination of contact angle, monolayer tension, or free energy of formation.

Applying voltage across a BLM affects the equilibrium interfacial geometry of the suspended film through a process known as electrowetting.[20,24,27,28] Specifically, an applied electric field increases the external contact angle at the annulus, which drives a subsequent increase in area of the bilayer. The relationship between the contact angle and the applied electric field is described by the Young-Lippmann equation that relates the change in contact angle at the edge of the bilayer to the specific capacitance of the membrane and monolayer tension. When the membrane specific capacitance and monolayer tension are themselves not functions of voltage, the change in contact angle is described by $$\cos\theta_0 - \cos\theta_V = \frac{C_M}{4\gamma_m} V^2.$$

Equation 3

Equation 3 includes the contact angle measured at a nonzero applied voltage ($\theta_0$), the zero-volt contact angle ($\theta_0$), the capacitance per unit area of the membrane ($C_M$), the monolayer surface tension, and the voltage applied across the membrane (V). Equation 3 shows that if $C_M$ is known, $\gamma_m$ can be determined experimentally by measuring the voltage dependent change in the cosine of the contact angle.

Requena and Haydon[20] were the first to verify that this relationship could provide access to $\gamma_b$, though they suggested that either $C_M$ or $\gamma_m$ would be known ahead of time from a separate experiment. Their work also highlighted the difficulty in determining an accurate value for the area of a suspended BLM, which is required to precisely determine $C_M$. Consequently, rather than using Equation 3 to extract monolayer or bilayer tensions, they used this relationship and separate measurements of $\gamma_m$ as a way to determine $C_M$ from the electrowetting response.[20] This approach contrasts the more commonly used discrete measurements of electrical capacitance and bilayer area to determine specific capacitance.[20, 28-45] Yet, if $C_M$ and $\theta_V$ can be measured in situ, then the Young-Lippmann relationship and Young's equation show that $\gamma_m$, $\gamma_b$, and the free energy of bilayer formation can be comprehensively and simultaneously determined.

The droplet interface bilayer (DIB) method is a technique for assembling planar lipid bilayers to study membrane properties and membrane protein activity.[27, 46-57] Droplet interface bilayers form spontaneously between lipid-coated aqueous volumes immersed in oil. DIBs offer several advantages to other methods for bilayer formation, including long lifetimes (hours-days),[58] low-volume, tunable bilayer area,[24, 27, 54-56, 58, 59] control over the composition of each leaflet and of each droplet,[57] and potential for scale-up by forming multi-membrane networks with many droplets.[47-53] DIBs have been successfully used as soft functional building blocks for bottom-up synthetic biology, for example in the construction of tissue-like materials[48] and in the construction of spatially arranged artificial cells.[60,61] As illustrated in FIG. 2B, a DIB is energetically balanced by lipid monolayer tensions that oppose bilayer tension in the same manner as a suspended BLM. DIBs also possess the appropriate thickness and amphiphilic, two-dimensional liquid crystalline structure to reconstitute transmembrane proteins and peptides while retaining their natural function.[58,62, 63] However, unlike suspended BLMs, the DIB allows for optically tracking both the contact angle and the interfacial area between droplets, in addition to permitting electrical measurements of membrane capacitance.

In accordance with the presently disclosed subject matter, DIBs are employed to study the effects of proteins, cell-penetrating peptides, and other biomolecules and lipophilic species on bilayer capacitance, tension, and free energy of formation by combining methods for determining membrane specific capacitance with a technique to measure contact angle. Using a coupled approach, the presently disclosed subject matter demonstrates that both monolayer and bilayer tensions can be measured in situ by tracking changes in $C_M$ and θ with a droplet interface bilayer (DIB) at varying bias voltages. Representative advantages of DIBs for this type of experiment include: 1) control of droplet positions relative to one another allows for direct tuning of the area of the interface, which allows for accurate determination of $C_M$; and 2) simple optical imaging of the adjoined pair can be used to determine both membrane area and θ across a range of applied electric fields.

Disclosed herein in some embodiments is the demonstration of the accuracy and sensitivity of a multi-step tuning technique that allows for measurement of monolayer and bilayer tension in a DIB. First, mechanical tuning of the interfacial area is used to determine specific membrane capacitance. Then, an electrical tuning routine is performed to determine lipid monolayer tension via $C_M$ and θ values obtained at various applied voltages. Bilayer tension is subsequently determined from values of $\gamma_m$ and θ using Equation 1 (Young's equation). In situ measurements of monolayer tension are compared to separate measurements of monolayer tension obtained via the pendant drop method. After confirming that monolayer tensions can be accurately obtained via measurements of $C_M$ and θ, the presently disclosed subject matter is employed for measuring changes in membrane capacitance, monolayer tension, and bilayer tension (via the Young's equation) caused by the addition of cholesterol, known to affect lipid packing and order and, separately, the incorporation of silicone oil into the oil phase surrounding the droplets. The ability to detect cholesterol-induced changes in thickness help validate the method for future use in studies of the effects of other biomolecules, while measurements using different mixtures of oils confirms what is known about size-selectivity of oil retention versus exclusion in a BLM. These oil mixtures also represent commonly used oils in DIB assembly.[48, 64]

III. Presently Disclosed Methods and Apparatus

In some embodiments, the presently disclosed subject matter provides a method and an apparatus for determining a plurality of physical properties of an artificial cellular membrane. An exemplary apparatus 1 of the presently disclosed subject matter is shown in FIG. 1. As shown in FIG. 1, apparatus 1 includes transparent chamber 22 which can hold or is holding hydrophobic liquid medium 24. Transparent chamber 22 is open at the top to receive first and second electrodes 10. First and second electrodes 10 each include a coated tip 12, e.g., a hydrogel or other hydrophilic coating During use of apparatus 1, first and second droplets 16 are attached to first and second electrodes 10 at the coated tips 12. First and second droplets 16 comprise an aqueous solution that can comprise an amphiphilic molecule or mixture of molecules. The amphiphilic molecules form a monolayer coating 18 on the outer surface of droplets 16. Additionally or alternatively, hydrophobic liquid medium 24 can include an amphiphilic molecule or mixture of molecules that can form or also take part in forming monolayer coating 18. As indicated in FIG. 1, artificial membrane forms at the interface of droplets 16, when droplets 16 are brought into contact with each other. In the embodiment shown in FIG. 1, apparatus 1 includes optional micromanipulators (e.g., three axis micromanipulators) 34 attached to each of first and second droplets 16 via micromanipulator arms 35 to aid in the positioning of droplets 16.

Transparent chamber 22 is positioned over inverted microscope 32. Inverted microscope 32 comprises camera 36 which can record optical images of droplets 16 and artificial membrane 20. Alternatively or additionally, one or more camera(s) and/or objective lens(es) could be positioned elsewhere to view and/or obtain images of droplets 16. For example, a camera or objective lens could be placed along or adjacent to a side of chamber 22 to view droplets 16 horizontally. One or more camera angles can be employed, such as one from the bottom and one from the side, together. Optionally, as shown in apparatus 1 of FIG. 1, camera 36 is in communication with data acquisition system 30, which can include for example, a computer. Data acquisition system 30 can control microscope 32 and camera 36, and process images of artificial membrane 20.

Apparatus 1 also includes wave form generator 26, which is in electrical communication with first and second electrodes 10. In some embodiments, wave form generator 26 is also in electrical communication with data acquisition system 30, such that wave form generator 26 can be controlled by the data acquisition system 30. Apparatus 1 can further include amplifier 28 (e.g., a patch clamp amplifier), which can be used in combination with data acquisition system 30 to measure artificial membrane current response.

In some embodiments, the presently disclosed subject matter provides a method of determining a plurality of physical properties of an artificial cellular membrane using an apparatus, such as that described above and/or by forming an artificial cellular membrane at an interface between two droplets of an aqueous solution, wherein the artificial cellular membrane comprises an amphiphilic molecule or mixture of amphiphilic molecules, and wherein the method comprises taking various electrical and optical measurements of the artificial cellular membrane and calculating the physical properties based on the data thereby obtained. Thus, in some embodiments, the presently disclosed subject matter provides a method comprising: droplet interface bilayer (DIB) formation; specific capacitance measurement via a series of simultaneous electrical measurements of membrane capacitance and optical imaging to determine membrane area; and monolayer and bilayer tension determination via electrowetting.

In some embodiments, the apparatus and/or method can be used to compare the effects of a change in membrane composition by comparing the properties of two artificial cellular membranes. For example, the method and/or apparatus can be used to determine the effect of changing lipid composition (e.g., adding or changing the concentration of cholesterol) or the effect of a drug (e.g., an anesthetic, such as lidocaine or ethanol) on membrane properties (e.g., specific capacitance, monolayer tension, bilayer tension, thickness, and/or free energy of formation).

In some embodiments, the plurality of physical properties comprise specific capacitance, monolayer tension, and bilayer tension. In some embodiments, the method further comprises determining one or more of membrane thickness, free energy of formation, and a parameter that describes electrowetting behavior, optionally alpha, beta, and/or B coefficients.

In some embodiments, a hydrophilic non-liquid body (e.g., a hydrogel) coated with a lipid or amphiphilic molecule or polymer can take the place of a liquid droplet. In some embodiments, a droplet is attached to hydrated gel on a surface (a "droplet hydrogel bilayer", referred to as a DHB. In some embodiments, amphiphilic molecules are selected from the group consisting of a lipid, an amphiphilic polymer, a biological membrane extract, and a mixture thereof. In some embodiments, the aqueous solution and/or hydrophobic medium further comprises one or more of the group consisting of a small molecule, a peptide, a protein, a biomolecule, and a pharmaceutically active agent. In some embodiments, the amphiphilic molecules comprise a lipid or lipid mixture selected from the group consisting of a fatty acyl, a glycerolipid, a glycerophospholipid, a shingolipid, a sterol lipid, a prenol lipid, a saccharolipid, a polyketide, a phospholipid, a fluorescent lipid, a glycolipid, cholesterol, a biological membrane extract, and a mixture thereof. In some embodiments, the amphiphilic molecules comprise one or more of the group consisting of 1,2-diphytanoyl-sn-glycero-3-phosphocholine (DPhPC), 1,2-dioleoyl-sn-glycero-3-phosphocholine (DOPC), palmitoyl oleoyl phosphatidylcholine (POPC), 1-palmitoyl-2-oleoyl-phosphatidylethanolamine (POPE), 1-palmitoyl-2-oleoylphosphatidylglycerol (POPG), 1,2-di-O-phytanyl-sn-glycero-3-phosphocholine (DoPhPC), dipalmitoylphosphaditdylcholine (DPPC), 1,2-dioleoyl-sn-glycero-3-phosphoglycerol (DOPG), DSPC, DPhPG, DPhPS, DOPS, DPPS, DPPE, Rhodamine-DPPE, NDB-DPPE, and cholesterol. In some embodiments, the hydrophobic liquid medium comprises a natural oil (such as but not limited to olive oil, vegetable oil, triolein, monoolein, and other neutral lipids that are largely hydrophobic), an alkane, an alkene, a fluorocarbon, a silicone oil, a hydrophobic polymer, an amphiphilic polymer, a wax, or a mixture thereof. In some embodiments, the hydrophobic liquid medium is one or more of the group consisting of n-hexadecane, heptadecane, tetradecane, squalene, dodecane, silicone oil, decane and mixtures thereof. In some embodiments the hydrophobic liquid medium is contained in a transparent chamber, wherein a side of said chamber, optionally a top side of the chamber, is completely or partially open to receive the electrodes. Optionally, the transparent chamber comprises or consists of polydimethylsiloxane (PDMS), glass, acrylic or rubber.

In some embodiments, the first electrode and the second electrode are coated with one of the group consisting of a hydrogel, agarose, polyacrylamide, nitro-cellulose, cellulose acetate, glass, mesoporous silica, cross-linked polyethylene glycol, a chemically linked layer of biomolecules, proteins, or other species to provide a hydrophilic surface, and a patterned or textured surface created to display a desired wetting property. In some embodiments, the first and second electrode each comprise silver/silver chloride.

In some embodiments, the method comprises (i) preparing the aqueous solution, wherein the aqueous solution comprises an amphiphilic molecule or mixture of amphiphilic molecules; (ii) attaching the first droplet of the aqueous solution to a tip of the first electrode and attaching the second droplet of the aqueous solution to a tip of the second electrode; (iii) suspending the first and second droplets in the hydrophobic liquid medium; and (iv) moving the first and/or second electrode to position the first and second droplets relative to one another to form an interface between the first and second droplets.

In some embodiments, the amphiphilic molecule or mixture of amphiphilic molecules comprises an amphiphilic polymer, optionally an ABA block copolymer, and wherein step (iv) further comprises applying a voltage.

In some embodiments, determining of a nominal capacitance and an artificial cellular membrane area at each of a plurality of artificial cellular membrane areas comprises: (v) moving the first and/or second electrode to change the relative position of the first and second droplets and thus the artificial cellular membrane area; (vi) waiting for the nominal capacitance to stabilize, optionally wherein the waiting is for between about 30 seconds and about 60 seconds; (vii) recording the nominal capacitance and acquiring an optical image of the artificial cellular membrane; (viii) calculating the area of the artificial cellular membrane using data from the optical image; and (ix) repeating steps (v)-(viii) one or more times, optionally four times, prior to calculating the specific capacitance.

In some embodiments, the contact angle between droplets at each of the plurality of applied bias voltages is measured using an optical image of the droplets taken during the application of each of the applied bias voltages.

In some embodiments, calculating the monolayer tension comprises determining the slope of a linear least squares regression of a plot of the change in the cosine of the contact angle as a function of voltage squared and using the slope and the specific capacitance determined in step (b) to determine monolayer tension using the Young-Lippmann equation. In some embodiments, calculating the bilayer tension comprises using the Young-Dupre equation.

In some embodiments, a method of determining the effect of a change in the chemical composition of an artificial cellular membrane is provided. In some embodiments, the method comprises:
(a) preparing an artificial cellular membrane at an interface between a first droplet and a second droplet of a first aqueous solution wherein the first aqueous solution comprises an amphiphilic molecule or mixture of amphiphilic molecules, and wherein the first droplet and the second droplet are each attached to separate electrodes and suspended in a hydrophobic liquid medium;
(b) determining specific capacitance of the artificial cellular membrane, wherein the determining comprises determining a nominal capacitance and an artificial cellular membrane area at each of a plurality of artificial cellular membrane areas, wherein artificial cellular membrane area is varied by changing the position of the first or second droplet relative to the other of the first and second droplets, and optionally wherein the specific capacitance is calculated from the slope of a linear least squares regression of the nominal capacitance versus area data;
(c) determining an artificial cellular membrane tension, wherein the determining comprises fixing the positions of the first and the second droplets relative to each other, measuring the contact angle of the droplets at a plurality of applied bias voltages, and calculating the monolayer and bilayer tension;
(d) repeating steps (b)-(c) for an artificial membrane formed at the interface of a first and a second droplet of a second aqueous solution, wherein the second aqueous solution comprises an amphiphilic molecule or molecules, and wherein the chemical composition of the second aqueous solution differs from the chemical composition of first aqueous solution, and wherein the first and the second droplet of the second aqueous solution are each attached to separate electrodes and suspended in a hydrophobic liquid medium; and
(e) comparing the data obtained in for the artificial cellular membrane formed with droplets of the first aqueous solution to that obtained for the artificial membrane formed with droplets of the second aqueous solution, thereby determining the effect of a change in chemical composition of the artificial cellular membrane.

In some embodiments, the second aqueous solution comprises a small molecule, peptide, protein, biomolecule, or pharmaceutically active agent that is not be present in the first aqueous solution, and wherein the method determines the effect of the small molecule, peptide, protein, biomolecule, or pharmaceutically active agent on the artificial cellular membrane. In some embodiments, the second aqueous solution comprises a small molecule or pharmaceutically active agent, wherein the pharmaceutically active agent is an anesthetic or model anesthetic, optionally lidocaine or ethanol. In some embodiments, the small molecule, peptide, protein, biomolecule or pharmaceutically active agent is present in both the first and second aqueous solution, but can, for example, be present in different concentrations and/or the artificial membrane formed at the interface of droplets of the first solution and the artificial membrane formed at the interface of droplets from the second solution can contain a different composition of amphiphilic molecules. In some embodiments, a method of forming an artificial cellular membrane comprising an amphiphilic block copolymer is provided. In some embodiments, the method comprises: (a) preparing an aqueous solution comprising an amphiphilic block copolymer, optionally wherein the amphiphilic block copolymer is an ABA block copolymer comprising hydrophilic A blocks and a hydrophobic B block; (b) attaching a first droplet of the aqueous solution to a tip of a first electrode and attaching a second droplet of the aqueous solution to a tip of a second electrode; (c) suspending the first and second droplets in a hydrophobic liquid medium; (d) moving the first and/or second electrode to position the first and second droplets in physical contact with one another; and (e) applying a voltage, thereby forming the artificial cellular membrane, wherein the artificial cellular membrane comprises a copolymer-stabilized interface (CSI) between the first and the second droplets.

In some embodiments, the amphiphilic copolymer is an ABA block copolymer comprising poly(ethylene oxide) (PEO) A blocks and a polydimethylsiloxane (PDMS) B block. In some embodiments, the hydrophobic liquid medium comprises a mixture of a hydrophobic solvent and an amphiphilic copolymer, optionally an ABA block copolymer. In some embodiments, the method further comprises characterizing the artificial cellular membrane via electrical measurements and/or optical imaging.

In some embodiments, an artificial cellular membrane comprising a copolymer stabilized interface (CSI) between a polymer-coated first droplet of an aqueous solution and a polymer-coated second droplet of an aqueous solution is provided. In some embodiments, the artificial cellular membrane comprises an ABA block copolymer, optionally block copolymer comprising poly(ethylene oxide) (PEO) A blocks and a polydimethylsiloxane (PDMS) B block.

IV. EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Materials and Methods Used in Examples 1-7

Materials

Sodium chloride (NaCl), 3-(N-morpholino)propanesulfonic acid (MOPS), sodium hydroxide (NaOH), agarose (A9539), n-hexadecane (99%), AR 20 silicone oil (product number 10836), acetone, and isopropyl alcohol (IPA) are acquired from Sigma Aldrich, St. Louis, Mo., United States of America. Aqueous buffer (pH 7.4, 100 mM NaCl, 10 mM MOPS) is prepared as described previously.[56] 1,2-diphytanoyl-sn-glycero-3-phosphocholine (DPhPC) and cholesterol (ovine wool, >98%) are acquired as lyophilized powders from Avanti Polar Lipids, Inc., Alabaster, Ala., United States of America, and stored at −20° C. To prepare solutions of single unilamellar DPhPC liposomes, lipids are first suspended in aqueous buffer at a concentration of 2 mg/mL before being subjected to 5 freeze/thaw cycles to create stock solutions of multilamellar liposomes. Unilamellar DPhPC liposomes are formed by extruding thawed stock lipid solution through 100 nm-pore polycarbonate membranes (Whatman, Maidstone, United Kingdom) using an Avanti Mini Extruder. To create liposomes containing DPhPC and cholesterol, the lyophilized (powder) form of each component is dissolved in chloroform to create separate 5 mg/mL stock solutions. Appropriate volumes of each chloroform stock are mixed to obtain the desired DPhPC: cholesterol molar ratio, and the vial containing the mixture is placed under vacuum for several hours to remove the solvent. The resulting films are rehydrated with buffer to achieve a final DPhPC concentration of 2 mg/mL, incubated between 35-45° C. to help dissolution, and then sonicated at 45° C. using a bath sonicator (FS20D, Fisher Scientific, Waltham, Mass., United States of America) for several hours or until the solution is completely clear. Sonication is preferred over extrusion with cholesterol-containing mixtures to prevent removal of cholesterol by the polycarbonate membranes during extrusion. Sonicated and extruded liposome solutions are stored at 4° C. until further use. Cholesterol-containing solutions are checked for optical clarity before testing and re-sonicated to clarity if there is any evidence of cholesterol demixing.

Methods for DIB Formation and Characterization

DIBs are formed between two aqueous droplets suspended in the oil-filled reservoir of a transparent PDMS substrate, as described elsewhere.[56] Briefly, aqueous droplets (300 nL unless otherwise stated) are pipetted onto agarose-coated, ball-end silver/silver-chloride electrodes made from 50 μm silver wire (Sigma). Suspended droplets "hang" on the gel-coated electrode tips under oil and are intentionally free of contact with either the upper oil/air interface or the PDMS substrate. Optical clarity is improved by injecting a small volume (<10 μL) of hexadecane between the substrate and microscope slide. Each electrode is affixed to a 3-axis micromanipulator (World Precision Instruments, Kite-L and Kite-R models, Sarasota, Fla., United States of America) to allow precise control over the position of each droplet. To dynamically vary bilayer area when determining specific capacitance, one droplet is moved closer to or further away from the other droplet using the micromanipulator. Current measurements are made using an Axopatch 200B patch clamp amplifier and Digidata 1440 data acquisition system (Molecular Devices, Sunnyvale, Calif., United States of America). All recordings are made with appropriate shielding in place to reduce noise to less than ±5 pA. Nominal capacitance measurements are based on the bilayer's current response to a 10 mV, 10 Hz triangular voltage waveform output from an Agilent 33210A waveform generator (Agilent, Santa Clara, Calif., United States of America).[56] Membrane capacitance is extracted from sections of the square-wave current response using MATLAB (MathWorks, Natick, Mass., United States of America). To induce electrowetting between droplets, custom dc step voltage routines are employed as described previously.[56] Images of DIBs taken from below through the 4× objective lens of an Olympus IX50 inverted microscope are acquired with a QI Click CCD camera (Olympus, Center Valley, Pa., United States of America) controlled using pManager software (pManager, San Francisco, Calif., United States of America).[65] DIB images are post-processed using custom scripts in MATLAB to extract bilayer contact length (used for bilayer area calculation) and contact angle (for measurements of tensions and free energies). Bilayer area calculations account for droplet sagging due to differences in density between the aqueous and oil phases. In every DIB test, droplets are freely suspended under oil and above the substrate surface to reduce error in calculation of bilayer ellipticity. The droplets are positioned at the same height such that the waist of each droplet is in focus when viewed from the bottom-up. The height of each droplet is adjusted before specific capacitance and tension measurements to maintain appropriate focus.

Pendant Drop Measurements of Monolayer Tension

For comparative purposes, interfacial tension of lipid and lipid-cholesterol monolayers formed at various oil-water interfaces can also be measured via the pendant drop method with a Model 590 goniometer and DROPimage Advanced software (Ramé-Hart Instrument Co., Succasunna, N.J., United States of America). The method involves forming a pendant drop from one of the liquid phases (i.e. aqueous solution) at the tip of a needle submerged in the other phase (i.e. oil). A horizontally mounted camera acquires images of the droplet profile at a frequency of 1 Hz, which are used by the software to compute the surface tension versus time. Due to the extremely low interfacial tension ($\leq 1$ mN/m) achieved by lipid monolayer self-assembly, a pendant drop of aqueous lipid solution formed at the tip of a needle in oil often falls off, making it hard to measure the equilibrium tension. This can be problematic when the effects of gravity are significant, for instance when testing with hexadecane which has a much lower density than the aqueous phase ($\rho_{hexadecane}$=0.77 g/mL compared to $\rho_{buffer}$=1.00 g/mL). To circumvent this problem, a J-shaped needle can be used to form an oil drop in the lipid aqueous solution. A glass cuvette is thoroughly cleaned by rinsing in acetone, isopropyl alcohol (IPA), and then deionized water before placing the cuvette in an oven (80° C.) for several minutes or until it is fully dry. Clean, dry cuvettes are filled with 2 mL of liposome solution ($\rho$=1.0007 g/mL). A clean 23 gauge steel needle (Rame-Hart) is bent to form the J-shaped dispensing tip, taking care to ensure that the tip of the needle will be vertically oriented once assembled onto the goniometer. After fitting the needle on the automatic dispenser, a few μL of the appropriate oil mixture is drawn into the needle. In order to prevent wetting of oil on the needle's exterior surface, the tip of the needle is dabbed with a clean wipe to remove residual oil before lowering the needle into the cuvette such that the tip is fully submerged into the aqueous solution. A 1 μL drop of the oil mixture is dispensed at the tip of the needle and the interfacial tension measurement begins. Measurements are taken at a rate of 60 samples per minute until an equilibrium value is reached. All measurements are performed at room temperature.

Example 1

Specific Capacitance, Monolayer Tension, and Bilayer Tension Measurement with a DIB FIG. 3A illustrates the three-part process for measuring $C_M$, $\gamma_m$, and $\gamma_b$ on a DIB. In Part 1, a DIB is formed between two aqueous droplets suspended on agarose tipped ball-ended electrodes in oil. The initial thinning of the bilayer occurs generally within 1-2 minutes of initial contact and results in a rapid increase in the amplitude of the capacitive current signal due to the formation of a thinned bilayer region between droplets. The area of the thinned region and the angle between droplets stabilize to constant values when the total energy of the connected droplets reaches a local minimum.[48]

Part 2 of the process involves incrementally changing the bilayer area, and thus the nominal capacitance of the interface, by moving one electrode in a stepwise fashion relative to the other. As others have shown,[27] returning the mobile electrode to its original position results in a reversible change in the capacitive current and bilayer area. The size of the bilayer at each position stabilizes within about 30 s of the electrode positioning. At each level of contact area (typically >5 contact areas are prescribed), the steady-state amplitude of the square-waveform current signal is recorded and an image of the DIB is acquired simultaneously. Nominal capacitance is computed using $C=i/(4Af)$, where i is the amplitude of the current waveform measured at steady state and A and f are the amplitude and frequency, respectively, of the applied triangular waveform voltage. Specific capacitance is obtained simply from the slope of a linear least squares regression of nominal capacitance versus area data from all electrode positions (FIG. 3A, center).[27, 56]

Part 3 uses an applied dc transmembrane voltage that increases in a stepwise fashion in addition to the ac triangular voltage required for capacitance measurement. This procedure begins by fixing the electrode (i.e. droplet) positions, setting the bias voltage to zero, and allowing the DIB to equilibrate for several minutes to ensure the droplets reach a steady contact area and angle. Images are taken at the 0 mV equilibrium point to allow measurement of $\theta_0$ before voltage is increased in a stepwise fashion. The bilayer is held at each new voltage for 15-30 seconds, during which electrowetting causes the external bilayer contact angle to increase as predicted by the Equation 3 (Young-Lippmann equation). Images ($n \geq 10$) of the contact angle ($\theta_V$) are obtained at the end of each voltage step and the process is repeated at successively higher voltage levels. This part of the experiment takes only a few minutes to perform. Using the average contact angle from each voltage level, the change in the cosine of the contact angle is plotted versus the square of the applied bias voltage (FIG. 3A, right). As noted above with Equation 3, the change in the cosine of the contact angle is recorded with respect to the cosine of $\theta_0$.

FIG. 3B shows the square current waveform induced by the ac triangular voltage applied to a DPhPC DIB formed in hexadecane during all three parts of the experiment. FIG. 3C shows the corresponding bilayer capacitance, computed from the same current response, versus time. During Part 1 of the experiment, the amplitude of square current waveform stabilizes at ~240 pA. Images of the connected droplet pair show that $\theta_0$ is 29.3° for this type of lipid and oil.

The second and third parts of the measurement process result in stepwise changes to bilayer capacitance, caused by mechanical and electrical tuning, respectively. During Part 2, the measurement shows that at each successive electrode position (i.e. farther apart), the square wave current stabilizes to smaller amplitude, which corresponds to smaller area of contact and thus capacitance. Conversely, the application of an increasing dc bias (of either polarity) drives the square wave current and bilayer capacitance to successively higher levels in Part 3.

The micrographs of a DPhPC DIB in hexadecane in FIG. 4A show that increasing levels of electrowetting lead to increases in the external contact angle, $\theta$, as well as the projected length of the interface, a. FIG. 4B presents the capacitance versus area data obtained in Part 2 of the same test on this DIB, and the change in the cosine of the contact angle versus voltage data from Part 3 are shown in graphical form in FIG. 4C. Typically, tests to measure $\gamma_m$ conclude when the bilayer ruptures at voltages between |200-350| mV. In this test, $\theta$ increased from 28.8° at 0 mV to 35.9° at +225 mV. The change in cosine of the contact angle is well represented by a linear least squares regression with respect to $V^2$ across the range from 0 to 225 mV with an R-squared value >0.98. From Equation 3, it can be seen that the slope of the regression (m) is related to both $C_M$ and $\gamma_m$, as given by $$m = \frac{C_M}{4\gamma_m}.$$ Equation 4

Equation 4 is rearranged to solve for monolayer tension using the value of $C_M$ obtained in Part 2 and the value of m obtained in Part 3. The specific data shown in FIG. 4C yield a slope of m=1.372 which, combined with the $C_M$ value (slope from FIG. 4B) of 0.673 μF/cm$^2$, yields a computed value of monolayer tension, $\gamma_m$, equal to 1.23 mN/m. For a group of eight DPhPC DIBs formed in hexadecane, this method results in an average (±one standard deviation) monolayer tension of 1.18±0.136 mN/m, which is in agreement with prior results[25] and the results of independent pendant drop measurements of DPhPC monolayer tension (1.19±0.067 mN/m, n=3). A student t-test confirms that there is no significant difference (p<0.005) between the values obtained with either tension measurement method, which serves to validate an approach that leverages the electrowetting response of DIBs to determine the tension state. In summary, the measurement method introduced herein is capable of determining lipid monolayer tensions at the surfaces of the droplets that are consistent with those obtained using accepted techniques such as pendant drop goniometry.

After computing monolayer tension, the bilayer tension at zero volts is readily computed for each trial using Young's equation (Equation 1) along with the measured contact angle at 0 mV.[18, 21, 66] For the example shown in FIG. 4, the calculated monolayer tension (1.197 mN/m) and zero-volt contact angle of 28.7° 10 results in a calculated value for $\gamma_b$ of 2.10 mN/m. For the pool of eight different DPhPC DIBs in hexadecane that are tested, an average value of 2.04±0.222 mN/m for the tension of DPhPC bilayers in hexadecane was obtained. Prior studies obtained values of 1.62 mN/m and 1.9±0.3 mN/m for planar lecithin bilayers[19, 67] and DPhPC DIBs,[25] respectively. The latter value, provided by Dixit et al., was obtained using Equation 1 along with the monolayer tension determined via independent goniometer measurements and the contact angle estimated using images of connected droplets. It is possible to calculate bilayer tension via Equation 1 using the data herein: the average value of monolayer tension obtained from the goniometer and the average contact angle in DIB measurements (29.3°, see Table 1) yields an estimate of 2.08±0.198 mN/m for bilayer tension. All of these results are in strong agreement with one another, and there is no significant difference (p<0.005) between bilayer tensions computed from monolayer tensions obtained via the pendant drop and DIB methods.

Figure 5:
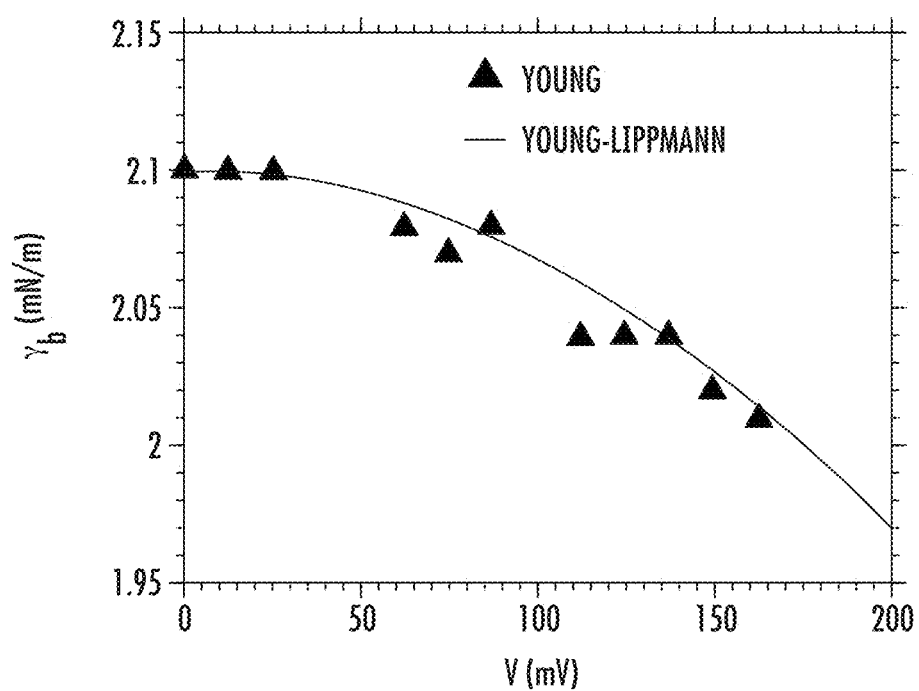
FIG. 5 is a plot showing bilayer tension (gb) as a function of applied voltage (V) for a DIB, calculated using the representative data presented in FIGS. 4A-4C. Triangle, Young; Line, Young-Lippmann.

It is also possible to use Equation 1 to discretely compute bilayer tension as a function of bias voltage using the measured values of $\gamma_m$ (fixed) and DIB contact angle at each voltage applied during Part 3 of the experiment. Additionally, the average bilayer tension can be empirically projected in a continuous fashion versus voltage using experimentally determined values of $C_M$, $\gamma_m$, and $\theta_0$. This second method evaluates bilayer tension versus voltage using a rearranged form of Equation 3, $$\gamma_{b,V}(V) = \gamma_{b,0} - \frac{C_M}{2}V^2,$$ Equation 5 along with the bilayer tension at 0 mV ($\gamma_{b,0}$) computed using Equation 1. FIG. 5 compares $\gamma_b$ as a function of voltage computed discretely and continuously using the values of θ, $C_M$, $\gamma_m$, and V obtained for the data presented in FIG. 4B-4C. Clearly, $\gamma_b$ decreases with increasing voltage, which illustrates that the stored electrical energy across the bilayer acts to mechanically relax the interface. Further, close agreement between the discrete data points and the continuous curve show that the measured contact angles and thus the computed bilayer tension, conform to the Young-Lippmann relationship for bilayer tension at voltages between 10-1751 mV. This agreement suggests that bilayer tension can also be computed accurately at a non-zero voltage provided the contact angle is measured at that potential and the monolayer tension is known. Monolayer tension is assumed to be independent of applied potential due to the fact that the thinned bilayer contributes the dominant electrical impedance between droplets. This occurs because of the presence of nonconductive oil in the Plateau-Gibbs border that is much thicker and has a lower capacitance per unit area than the bilayer. As a result, the applied voltage produces an electric field predominantly across the membrane.

For further comparison of the DIB Young-Lippmann equation with prior studies, it is possible to evaluate the reduction in free energy obtained upon droplet adhesion (Equation 2). For a DPhPC DIB formed in hexadecane, the calculated monolayer tension and average contact angle at 0 mV (29.3°) yield 0.301 mJ/m$^2$ as the free energy of bilayer formation. As further validation of the accuracy of the approach, the estimated free energy of formation is in direct agreement with the value of 0.31±0.02 mN/m for DPhPC bilayers formed in squalene,[23] as well as other reported values which fall between 0-2 mN/m.[18, 21, 22, 25]

Example 3

Effects of Mechanical Manipulation on Electrowetting and Tension Measurements

Figure 6C:
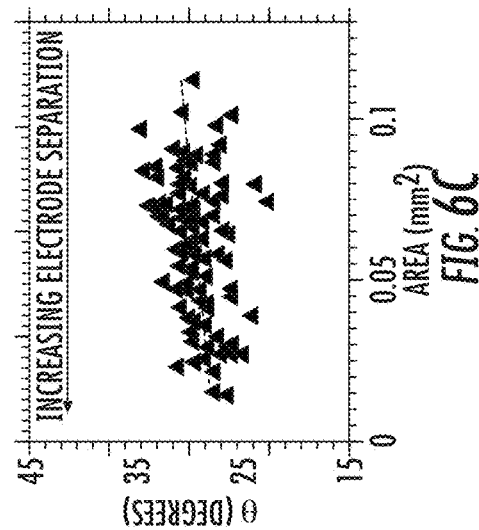
FIG. 6C is a plot of contact angle (y) measured from n>100 images obtained at varying area steps with 13 separate DPhPC DIBs during CM measurements.
Figure 6B:
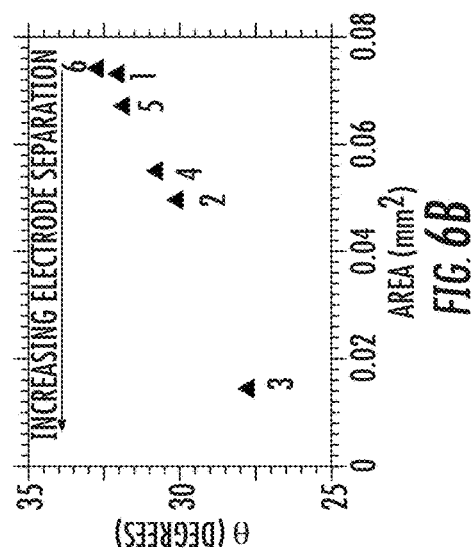
FIG. 6B is a plot of contact angle (y) measured from images of the DIB at each area step.
Figure 6E:
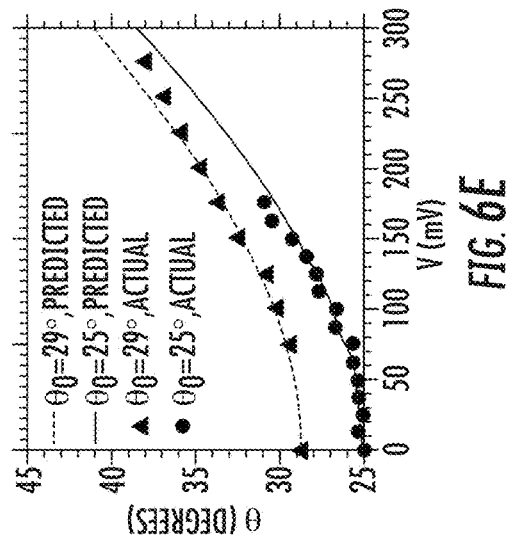
FIG. 6E is a plot showing theoretical ("predicted"; $y_0=29°$ (dashed line) and 25° (solid line)) and experimentally observed ("actual"; $y_0=29°$ (triangles) and 25° (circles)) nominal y as a function of voltage for the trials shown in FIG. 6D.
Figure 6D:
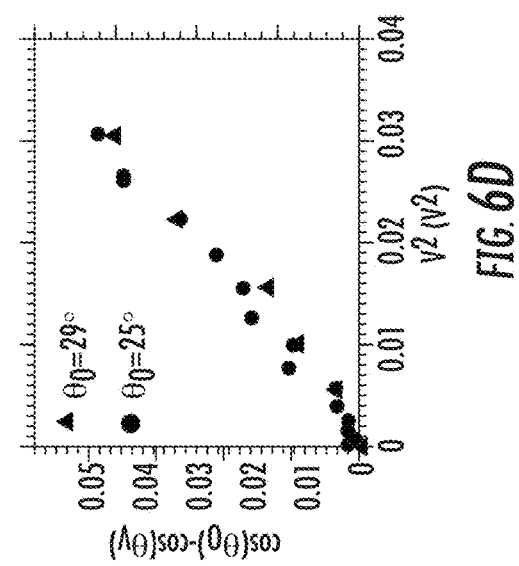
FIG. 6D is plot showing change in the cosine of y as a function of voltage for a DPhPC DIB mechanically manipulated to obtain two different zero-volt contact angles: $y_0=29°$ (triangles) and 25° (circles).
Figure 6A:
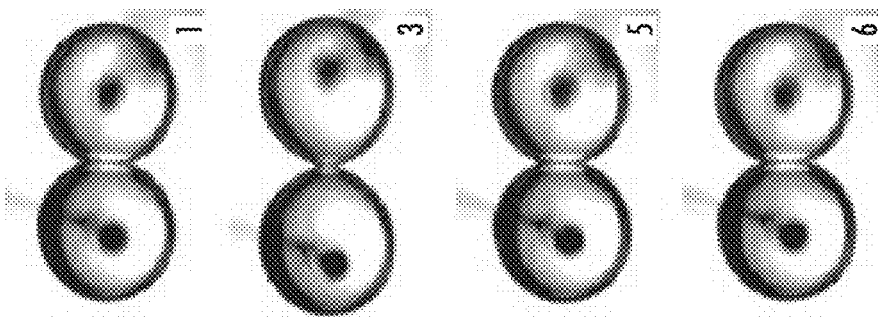
FIG. 6A is a series of images of a DPhPC DIB at varying steps during Part 2 (see FIG. 3A) of an experiment where DIB area is mechanically varied by moving one electrode and changing the distance between droplets.

In analyzing images obtained during specific capacitance measurements of DIBs (FIG. 3A, Part 2), the zero-Volt contact angle at equilibrium appeared to be directly affected by mechanical manipulation (i.e. positioning) of the droplets, which is used to intentionally vary the area of the bilayer. To explore this relationship, FIGS. 6A-6B show the results of a representative experiment in which droplets were successively pulled apart in 3 steps and then sequentially pushed back together in 3 area steps (see also FIGS. 9A and 9B). The data in FIG. 6B shows that the contact angle reversibly increases by as much as 5-6° as 300 nL droplets are pushed together to yield a larger interfacial area. To further test this response, FIG. 6C shows zero-Volt contact angle versus bilayer area obtained from n=115 various measurements made via Part 2 of the method on 13 different DPhPC DIBs. The larger population of data confirms that contact angle increases with mechanically driven increases in bilayer area. While the precise mechanism for this change in angle remains undetermined, the data suggest that pushing or pulling the droplets in a direction perpendicular to the interface reversibly alters the equilibrium tension balance that establishes the contact angle.

FIGS. 9A and 9B respectively show area and contact angle at each step during Part 2 of the DPhPC DIB experiment shown in FIG. 6A-6B. With each step, area is either decreased or increased by changing the distance between electrodes. Generally, contact angle is seen to increase with increasing bilayer area and vice versa.

The fact that changing the electrode separation distance alters droplet contact angle begs the question: how much does mechanical manipulation required for Part 2 affect the accuracy of the electrowetting-based method in Part 3 for determining monolayer tension in a DIB? To examine this possibility, the role of the zero-Volt starting contact angle, which was shown in FIG. 6A-6B to be a function of droplet positioning, was considered. Based on Equation 3, tuning or altering the initial wetting condition ($\theta_0$) should not affect the magnitude of the change in the cosine of the contact angle across a range of voltage assuming fixed $C_M$ and $\gamma_m$. However, the nominal change in contact angle does appear to depend on $\theta_0$ since the cosine of an angle varies nonlinearly. Such behavior is observed experimentally as portrayed in FIG. 6D and FIG. 6E, which show the theoretical and experimentally observed values for $\cos(\theta_0)-\cos(\theta_V)$ and $\theta_V$, respectively, with increasing applied voltage. The data portrayed is from two different electrowetting trials where the zero-Volt contact angle is varied ($\theta_0=29°$ and $\theta_0=25°$) by mechanical manipulation between trials. The data in FIG. 6D provides slope values of m=1.548 and m=1.579. With a specific capacitance value of 0.652 Uf/cm2, the resulting calculated monolayer tensions are 1.05/1.03 mN/m for ($\theta_0=29°/25°$) and the Young equation is used to calculate bilayer tension of 1.84/1.87 mN/m). The variation in $\theta_0$ causes <2% change to the slope, monolayer tension, and bilayer tension. Thus while mechanical manipulation can affect the zero-Volt contact angle, it does not significantly affect the ability to correctly determine monolayer and bilayer tension in the electrowetting-based method used in Part 3.

While varying $\theta_0$ does not affect the magnitude of the change in the cosine of the contact angle, the magnitude of the nominal voltage-dependent change in angle is expected to increase with decreasing zero-Volt contact angle due to the nonlinearity of the cosine function (see Example 7 herein below). This behavior is seen with both predicted and experimentally observed values for $\theta_V$ shown in FIG. 6E, which show that contact angles for DIBs starting at different contact angles appear be on converging trajectories at increasing voltage. These data also confirm that DIB contact angle follows the Young-Lippmann equation up to 175 mV, regardless of starting angle. At higher voltages, the data obtained from the DIB with $\theta_0=29°$ indicates that the change in the contact angle saturates. The saturation issue will be discussed later, but the immediate point to be made is that the lower initial $\theta_0$ incurs a larger nominal angle change as voltage increases. Thus, while a given amount of electrical energy (for fixed values of V, $C_M$ and $\gamma_m$) produces a fixed change in the cosine of the contact angle, the corresponding change in the nominal value of $\theta_0$ is greater when starting from a lower $\theta_0$ (closer to unity on the cosine curve, see FIG. 11). Because the presently disclosed method for measuring monolayer and bilayer tensions in a DIB can be limited by the resolution of contact angle measurement, the nonlinear relationship between angle change and applied voltage suggests that achieving a small $\theta_0$ (e.g. via mechanical manipulation or even through oil selection) could be used to maximize the nominal change in contact angle and improve the accuracy of this technique.

Nonetheless, it is useful to remember that the nominal contact angle is used in the Young Equation to compute bilayer tension. Thus, while the two membranes characterized in FIG. 6D-6E exhibited bilayer tensions within 2% of each other, the amplitude of error in determining bilayer tension also varies nonlinearly with starting contact angle. Thus, it can be advisable to initiate Part 3 of the method at a location where the droplets are minimally deformed by electrode separation in order to reduce the effects of mechanical manipulation on the accuracy of determining bilayer tension.

For completeness, the effect of starting contact angle on the voltage-induced change in membrane capacitance was also studied. The analysis showed that the sensitivities of nominal bilayer capacitance and area to voltage can be affected by the starting angle. However, the linear relationship between capacitance and area (FIG. 4B), and thus the determination of $C_M$, holds across a wide range of areas obtained via mechanical manipulation as previously shown.[56,27] In a following Example it was examined if specific capacitance varies under an applied dc voltage.

Example 4

Limits of Electrowetting in DPhPC DIBs

Numerous studies of electrowetting have shown that the change in the wetting angle saturates at high voltage, falling short of the expected angle change predicted by the Young-Lippmann equation.[68-71] With a single sessile droplet placed on a dielectric, common in many EWOD systems, the saturation limit is believed to be the result of dielectric charging or breakdown, charging of the insulating fluid surrounding the droplet, formation of instabilities and/or microdroplet ejection, or reduction of interfacial tension to zero.[69] The zero-tension theory, which states that the maximum angle change occurs at a voltage where the interfacial tension is zero,[69, 71] is capable of predicting the saturation angle for single droplet EWOD cases.[69] Applying this concept to a DPhPC DIB, the Young-Lippmann equation predicts that an applied voltage of nearly |800| mV is required to reduce a bilayer tension to zero (calculated using Equation 5 and values of $C_M$ and $\gamma_{b,0}$ for DPhPC DIBs in hexadecane, Table 1). However, because the typical rupture potential of DPhPC DIBs occurs at |200-300| mV,[56] it is unlikely that saturation of the contact angle could be caused by reducing tension to zero. Rather, the observed contact angle saturation at voltages above |175|mV appears to be likely due to dielectric breakdown and electroporation, which typically precede bilayer rupture.[56, 72]

Example 5

Effect of Increasing Voltage on $C_M$

When using specific capacitance to determine monolayer tensions in Equation 3, it can be of useful to understand how much $C_M$ varies when an electric field is applied to induce changes in the contact angle. The effect of voltage on $C_M$ has been shown previously to follow the experimental relation[27, 32, 40]

$$C_M = C_{M,0}(1+BV^2), \qquad \text{Equation 6}$$

which involves the specific capacitance at 0 mV ($C_{M,0}$), the magnitude of applied dc bias (V), and a parameter (B) describing the voltage dependence of $C_M$. While electrostriction of the membrane is a possible mechanism for voltage affecting $C_M$, prior works have suggested that planar lipid bilayers formed in the presence of solvents can exhibit voltage-dependent specific capacitance due to the electric field exerting a compressive force that excludes trapped oil from the membrane, thereby reducing the thickness of the hydrophobic core.[27, 32, 40] This effect can be significant when membranes are formed in the presence of organic solvents with high solubility in the hydrophobic region of the bilayer, and less in "solvent-free" membranes formed in the presence of large-molecule solvents that are more easily excluded from the hydrophobic region.[18, 73, 74]

Figure 7:
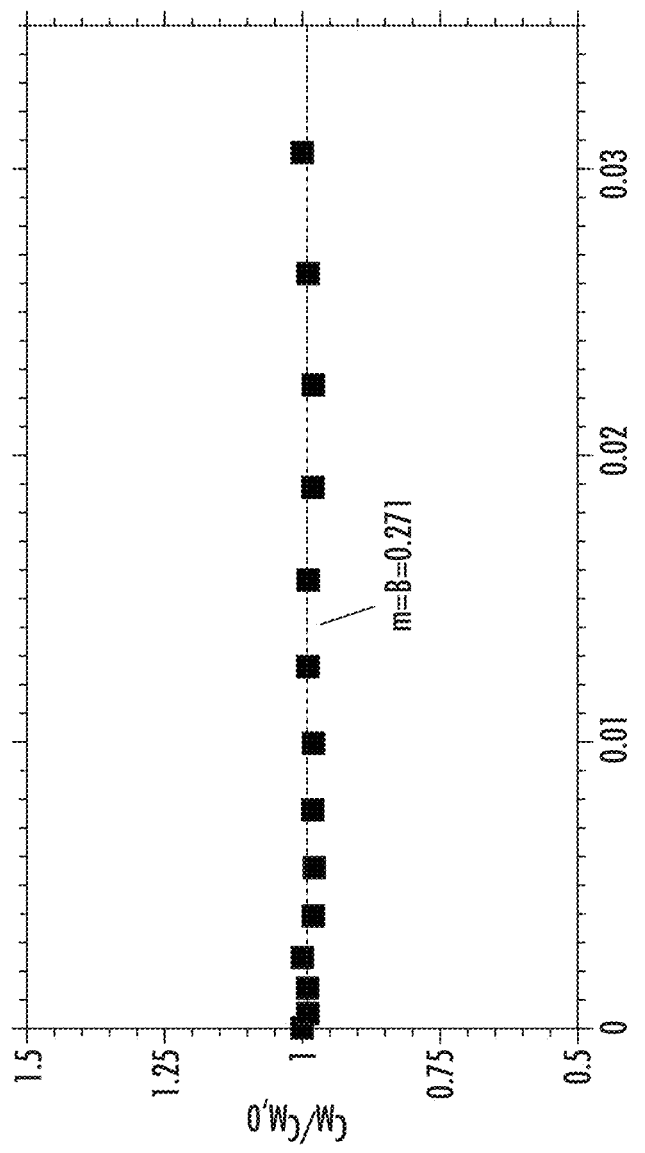
FIG. 7 is a plot showing normalized specific capacitance for a DPhPC DIB (hexadecane oil phase) as a function of applied voltage. $C_{M,0}$ is the specific capacitance measured via dynamic capacitance/area changes with voltage clamped at 0 mV (see FIG. 3A, part 2).

FIG. 7 shows values obtained for $C_M$ normalized by $C_{M,0}$ at each voltage step with a DPhPC DIB in hexadecane. Discrete values of $C_M$ at each voltage step are calculated using the capacitance and area at that voltage step (as opposed to dynamically varying area at each voltage step to determine $C_M$). Slight nonzero offset in the total measured capacitance is obtained from mechanical tuning and is used to correct the instantaneous calculated $C_M$. From Equation 6, a linear least squares regression of $C_M/C_{M,0}$ as a function of $V^2$ yields a straight line with an intercept of 1 and a slope of 0.27 $V^{-2}$ representing the value for parameter B. The resulting value of B indicates that $C_M$ would only increase by 0.01 µF/cm² at a voltage of |200|mV, a deviation that is approximately 1.6% of the value of specific capacitance measured at zero volts for DPhPC DIBs in hexadecane (0.67 µF/cm²). Compared to the larger B values measured for planar bilayers formed with decane as the oil-phase (4 $V^{-2}$),[27] this result is much lower, as could be expected due to the decreased solubility of hexadecane in the bilayer. The results are agreement with previously reported values of B in tests with solvent-free supported bilayers.[20, 27, 41] As a result, small values of B in solvent-free membranes can provide for monolayer and bilayer tensions based on contact angle and specific capacitance to be accurately determined using a value of specific capacitance obtained with zero bias applied. This approach is supported by previous reports that the Young-Lippmann equation can accurately predict the response of lipid bilayers subject to applied voltage when using a constant value for $C_{M,0}$.[20, 27, 75]

Example 6

Application of Capacitance and Tension Measurements

As described above, a multi-part procedure for determining monolayer and bilayer tension has been presented and validated with data obtained from DPhPC DIBs in hexadecane. However, to further demonstrate the value of this procedure, the presently disclosed procedure was also be used to study the effects of oil type and the addition of cholesterol on the specific capacitance and tension state of DIBs. As with DPhPC DIBs in hexadecane, equilibrium monolayer tensions are compared to values obtained on a pendant drop goniometer.

Figure 8A:
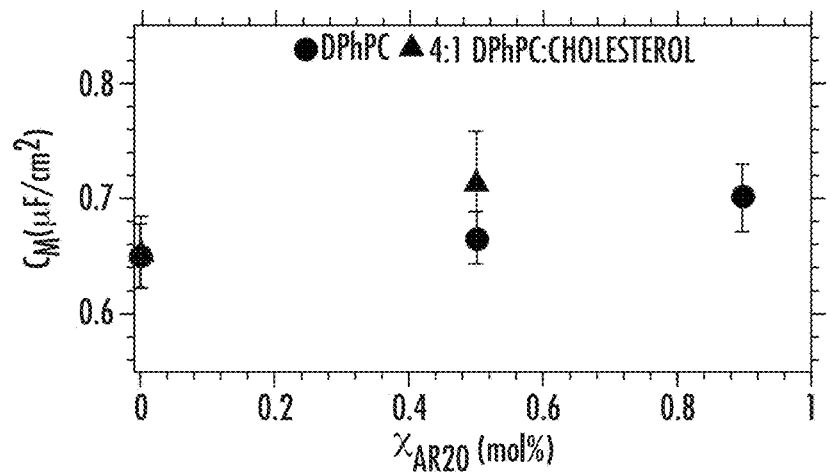
FIG. 8A is a plot of values obtained from measurements of specific capacitance for bilayers as a function of the fraction of silicone oil added to the hexadecane oil phase. Error bars show+/− one standard deviation. Two lipid compositions are tested in the various oil mixtures: pure DPhPC (circles); and DPhPC containing 20% (mol %) cholesterol (triangles).
Figure 8B:
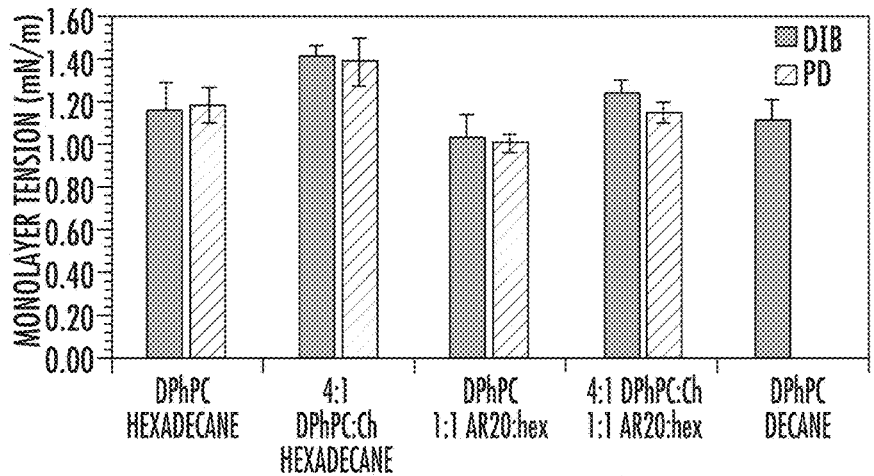
FIG. 8B is a bar graph showing "DIB" (gray bars)—monolayer tensions measured by monitoring Young-Lippmann related changes in DIB contact angle as voltage is increased; and "PD" (striped bars)—monolayer tensions measured using the pendant drop method with a goniometer.
Figure 8C:
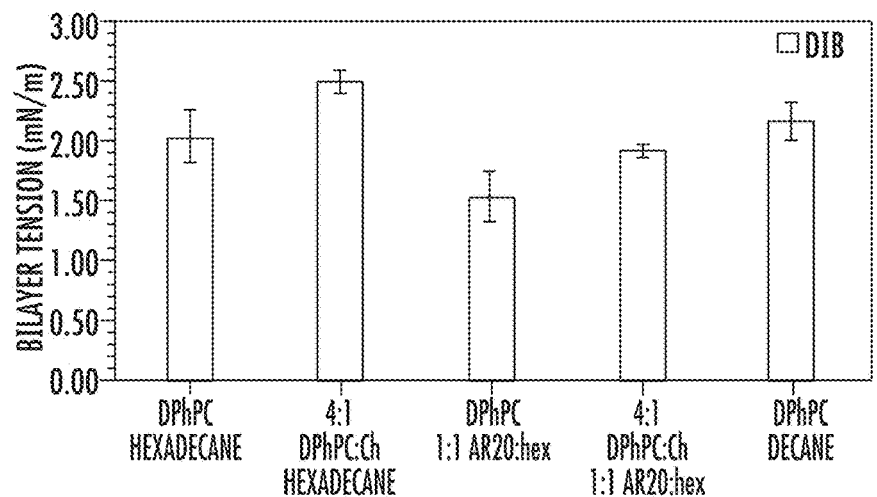
FIG. 8C is a bar graph showing bilayer tensions for each lipid-oil combination, calculated using average observed contact angle (case specific) and the monolayer tension measured via the DIB method used in FIG. 8B.

First, tests were performed to determine monolayer and bilayer tensions for DPhPC DIBs formed in a mixed solvent phase containing silicone oil (AR 20) and hexadecane. Prior to performing contact angle measurements versus voltage, values of specific capacitance are measured separately for DPhPC DIBs formed in pure hexadecane, in a 1:1 (vol:vol ratio) AR 20:hexadecane mixture, and in a 9:1 mixture of AR 20:hexadecane. Values obtained for $C_M$ (average±standard deviation) are shown in FIG. 8A as a function of the volume percentage of silicone oil. These values were then used in calculations of monolayer tension obtained via Part 3 of the experiment (FIG. 8B) and combined with measured values of $\theta_0$ for each to estimate bilayer tension at 0 mV (FIG. 8C). Table 1 presents average values, standard deviations, and the number of trials included for each case tested, as well as for DPhPC DIBs assembled in decane.

$C_M$ varies with the amount of solvent in the hydrophobic region.[27, 32, 73, 74] The solubility of solvent in the bilayer region generally increases with decreasing solvent molecule size.[18, 73, 74] As a result, techniques for measuring the thickness of the hydrophobic region are used to probe the amount of solvent trapped or dissolved in the bilayer.[27, 42] $C_M$ is related to the thickness of the hydrophobic region ($D_C$) and permittivity ($\varepsilon_r$) of the hydrophobic region of the bilayer, as well as the permittivity of vacuum ($\varepsilon_0$) by $$C_M = \frac{\varepsilon_r \varepsilon_0}{D_C}. \qquad \text{Equation 7}$$

The minimum value of $C_M$ for the three oil cases tested is obtained for DIBs formed in pure decane (0.488 µF/cm²), and the result is in close agreement with the value of 0.445 µF/cm² obtained elsewhere.[27] $C_M$ increases by 33% to 0.65 µF/cm² upon changing the solvent from decane to hexadecane, and the result is again consistent with previously reported values around 0.64 µF/cm².[27, 76] Compared to DIBs in hexadecane, $C_M$ increases by 3.1% to 0.67 µF/cm² for 1:1 AR 20:hexadecane and by 7.7% to 0.70 µF/cm² for 9:1 AR 20:hexadecane, respectively. The increase in $C_M$ with increasing silicone oil in the oil phase indicates a thinner, more solvent-free bilayer, while the reduced value of $C_M$ in decane indicates a thicker, oil-rich bilayer. Assuming a constant dielectric of $\varepsilon_r$=2.2 for the hydrocarbon-rich hydrophobic region of the bilayer, the present values of $C_M$ yield thickness values of 29.9, 29.2, and 27.8 Å for DPhPC DIBs in 1:0, 1:1, and 9:1 mixtures of silicone oil:hexadecane, respectively. The 9:1 mixture thus results in bilayers that are 7.3% thinner than those in pure hexadecane. Gross et al. reported that the hydrophobic region of DPhPC-hexadecane DIBs is 10% oil by volume, suggesting that with DIBs formed in the 9:1 mixture, the bilayer hydrophobic region consists of only 2.7% (10%-7.3%) solvent by volume. The 1:1 mixture invokes a similar effect, although the thickness reduces by only 2.7% leading to hydrophobic regions containing approximately 7.3% (10%-2.7%) oil by volume. These estimates assume that the changes in volume, based on $C_M$ measurements, are equal to the changes in membrane thickness (i.e. oil distributes evenly across the membrane area and the permittivity is unchanged). Converting percent volume oil to molar volume ratio provides a rough estimate of 6:1 for lipids:hexadecane in the hydrophobic region. The average thickness of DPhPC DIBs in decane is 39.9 Å. Based on the calculated thickness values, DIBs formed in decane are 33.4% thicker than those formed in hexadecane as a result of the increased solubility of small decane molecules in the hydrophobic region.[27] DPhPC bilayers formed in decane are expected to contain around 43% (10%+33.4%) oil by volume which is in close agreement with the estimate of 38% by Gross and Wallace.[27] Conversion of the volume ratio of lipid:decane to a molar volume ratio suggests that there are 1.7 decane solvent molecules for every lipid molecule present.

In addition to thickness, the oil used to form a DIB affects the tension state of a DIB.[18] Of the oils studied, bilayer tension is highest for DPhPC DIBs formed in decane. The data in FIG. 8 and Table 1 show that the presence of silicone oil has the opposite effect. The average monolayer tension decreases by 17% from 1.18 mN/m in pure hexadecane to 1.03 mN/m in the 1:1 mixture. Meanwhile, bilayer tension decreases by 29% from 2.04 mN/m in hexadecane to 1.54 mN/m in the 1:1 mixture. Note that for 0:1 and 1:1 AR 20:hexadecane mixtures, the monolayer tension values obtained via the multi-step technique introduced herein are not significantly different than the values obtained via pendant drop measurements with a goniometer. Tension values are not calculated for DIBs formed in the 9:1 AR20:hexadecane mixture, because these bilayers consistently ruptured at voltages near 100 mV which prevented the recording of increases in contact angle as applied bias voltage increases.

The free energy of formation is also a metric that can be used to understand the same phenomenon of oil-exclusion. Needham and Haydon[18] and Bibette et al.[21, 66, 77] reported that more solvent-free bilayers exhibit higher free energies of adhesion. The present results show that ΔF is nearly doubled in the 1:1 AR 20:hexadecane mixture compared to pure hexadecane, which itself has a ΔF value nearly four times that for decane-rich DIBs. Collectively, the DIB-electrowetting method appears to be a valid approach for measuring $\gamma_m$, $\gamma_b$, and ΔF, which serve as metrics for detecting solvent the presence of solvent and associated effects on lipid packing. The results of both $C_M$ and ΔF measurements herein support the understanding that addition of AR 20 silicone oil to the hexadecane oil phase surrounding the droplets reduces the amount of remaining solvent in a DPhPC DIB, resulting in a thinner, more relaxed interface. The fact that monolayer tension also decreases with increasing silicone oil content demonstrates that the hydrophobic regions of the lipid tails in monolayer are also better able to exclude silicone oil than pure hexadecane.

In a second study, the presently disclosed procedure was used to quantify the effects of cholesterol on $C_M$ and tensions in DPhPC DIBs formed in various organic solvents. This second study looked at the incorporation of 20 mol % cholesterol and did not pursue higher cholesterol levels due to its reduced solubility in DPhPC bilayers (40 mol % is the maximum for DPhPC,[78] compared with 50-60% across a range of acyl chain compositions (12:0, 16:0, and 22:0) and headgroup types (PC, PG, PE, and PS)[78]. When droplets containing DPhPC liposomes with 20 mol % cholesterol are used to form DIBs in pure hexadecane, a $C_M$ of 0.655±0.030 μF/cm², $\gamma_m$ equal to 1.42±0.051 mN/m, and $\gamma_b$ of 2.50±0.095 mN/m were obtained. In comparison, DIBs formed in 1:1 AR20:hexadecane from droplets of 20% cholesterol-DPhPC solution yield $C_M$ of 0.713±0.045 μF/cm², $\gamma_m$ equal to 1.24±0.056 mN/m, and $\gamma_b$ of 1.92±0.056 mN/m. The results for measured specific capacitance and tensions are illustrated in FIG. 8 and listed in Table 1.

The average value of $C_M$ is higher for DPhPC with 20% cholesterol compared to pure DPhPC in both oil cases tested. Assuming the effective dielectric constant of the interface is unchanged by the incorporation of cholesterol ($\varepsilon_r$=2.2)[79], Equation 8 suggests that the increase in $C_M$ could instead be attributed to thinning of the bilayer hydrophobic region. While numerous studies have identified lipid bilayer thickening upon incorporation of cholesterol,[13-16] the effect seems to depend on the length (relative to cholesterol) and degree of saturation of the lipid being used.[15, 17] For instance, McIntosh reports that bilayers comprised of phospholipids with up to 16-carbon acyl chains are thickened by the introduction of cholesterol, whereas 18-carbon chain bilayers in the solid phase (i.e. T<$T_m$) exhibit a reduction in thickness upon incorporation of cholesterol.[17] The effects of cholesterol on bilayer thickness are explained by comparing the hydrophobic lengths of the cholesterol and lipid chains[17]. Similar biphasic behavior regarding the effects of cholesterol on lipid transition temperature is also attributed to hydrophobic mismatch.[80] The cholesterol-induced decrease in thickness (FIG. 8A) measured herein suggests that a length mismatch exists between the DPhPC acyl chains and the embedded cholesterol. As encountered by McIntosh with 18-carbon acyl chains, the mismatch between rigid DPhPC tails and cholesterol hydrophobic lengths could create voids near the bilayer mid-plane that prompt the free ends of the acyl chains to bend or kink around embedded cholesterol molecules in an attempt to fill this space. The result is a net shortening of the lipid length and thinning of the bilayer hydrophobic region. This effect is also supported by molecular dynamics simulations showing flexible lipid acyl chains packing tightly around cholesterol molecules.[81]

The fact that $C_M$ increases with the addition of cholesterol in both pure hexadecane and the 1:1 AR20:hexadecane mixture shows that DPhPC bilayers containing cholesterol are thinner than those without cholesterol in each solvent case. Equation 8 allows calculation of bilayer thickness, again using $\varepsilon_r$=2.[2] as the dielectric constant, which reveals that bilayers containing 20% cholesterol possess a hydrophobic thickness of 29.7 Å or 27.3 Å when droplets are submerged in hexadecane or 1:1 AR20:hexadecane, respectively. Cholesterol reduces the thickness of bilayers in hexadecane by 0.14 Å (<0.5% of nominal value without cholesterol), however when DIBs are formed in a 1-1 AR20:hexadecane oil phase, cholesterol decreases bilayer thickness to 1.88 Å (a 6.4% reduction). This finding is consistent with prior studies that observed increased sensitivity of membrane specific capacitance to small molecules when bilayers are more solvent free, i.e. using solvents that are well-excluded from the hydrophobic region.[9, 12]

Additionally, the presently disclosed method shows that doping a DPhPC bilayer with cholesterol results in an increase in both monolayer and bilayer tension. This result is consistent with observations of previous studies[67,82] and could be explained by the fact that cholesterol interdigitation decreases packing in gel-phase bilayers,[83] such as those formed from DPhPC, which would drive increased interaction between water and the solvent or hydrophobic region of the bilayer. Incorporation of 20% cholesterol increases monolayer and bilayer tension by 0.24 mN/m and 0.21 mN/m in pure hexadecane and 1:1 AR20:hexadecane, respectively. The nominal changes to monolayer tension represent a 20.3% spike, while bilayer tension changes by 22.6% or 24.7% in hexadecane or the 1:1 AR20:hexadecane mixture. As with specific capacitance described above, bilayer tension can be more significantly affected by cholesterol when the membrane is solvent-free.

Free energy of adhesion (ΔF) also increases nominally through the incorporation of cholesterol into the bilayer. Raising cholesterol content to 20% increases ΔF of DPhPC DIBs formed in hexadecane by 0.010 mN/m (+3.3%). For DPhPC DIBs formed in the 1:1 AR20:hexadecane mixture, inclusion of 20% cholesterol causes ΔF to increase by +0.028 mN/m (+5.4%). It can be interesting to consider the mechanism by which cholesterol increases free energy of adhesion. Evidenced by the equation for free energy (Equation 2), ΔF increases with increases in either tension or contact angle. The present measurements demonstrate the cholesterol increases bilayer and monolayer tensions while causing the contact angle to decrease. To achieve such changes in all three parameters, Equation 1 verifies that the ratio $\gamma_b/2\gamma_m$ must in fact increase in response to the addition of cholesterol. Based on the experimentally obtained values in Table 1, increasing cholesterol content is accompanied by an increase in the ratio of $\gamma_b/2\gamma_m$ (0.853 and 0.880 at 0 and 20% cholesterol, respectively). The present data suggests that cholesterol causes less distortion of lipids positioned in the monolayers around the droplets compared to lipids in the bilayer interface, possibly due to the presence of bulk solvent molecules near the monolayers that fill voids between the sterol and lipid molecules. These results simultaneously support the notion that cholesterol affects bilayer tension more than monolayer tension through the same mechanism that results in membrane thinning: i.e. kinking and bending of the lipid acyl chains to "wrap" cholesterol molecules and fill sterol-induced voids in the hydrophobic region.

Collectively, results from the present measurements of $C_M$, $\gamma_m$, $\gamma_b$, and $\Delta F$ seem to confirm that the presently disclosed method is suitably capable for measuring changes to bilayer thickness and tension caused by changes in membrane composition or oil content. Interestingly, solvent-free DIBs formed in 1:1 AR20:hexadecane displayed a heightened sensitivity in terms of the effects of cholesterol on $C_M$, $D_C$, $\gamma_b$, and $\Delta F$. These takeaways provide guidance for investigating the effects of biomolecules, peptides, pharmaceutics, and other species on lipid bilayer thickness and tensions. Specifically, such studies could use 1:1 AR 20:hexadecane mixtures to amplify the effects on membrane thickness and tension caused by accumulation of a species of interest.

Example 7

Effects of Initial, Zero-Volt Contact Angle with Young-Lippmann

The Young-Lippmann equation can be used to predict the contact angle in response to applied voltage assuming that specific capacitance ($C_M$), monolayer tension ($\gamma_m$), and the zero-volt contact angle ($\theta_0$) are known. Rearranging Equation 3 from above yields $$\left( \cos(\theta_0) - \frac{C_M}{4\gamma_m} V^2 \right).$$ Equation 8

FIG. 10A shows theoretical $\theta$, as a function of voltage across the range of 0-300 mV for various initial contact angles ($\theta_0$=5°, 15°, 25°, 35°, 45°). $C_M$ and $\gamma_m$ values used in the calculations are taken from Table 1 herein (for DPhPC in hexadecane). The data in FIG. 10A can be used to compute the nominal change in the contact angle ($\Delta\theta$) in response to voltage for each zero-volt angle case using $$\Delta\theta(V) = \theta_V(V) - \theta_0.$$ Equation 9

Figure 11:
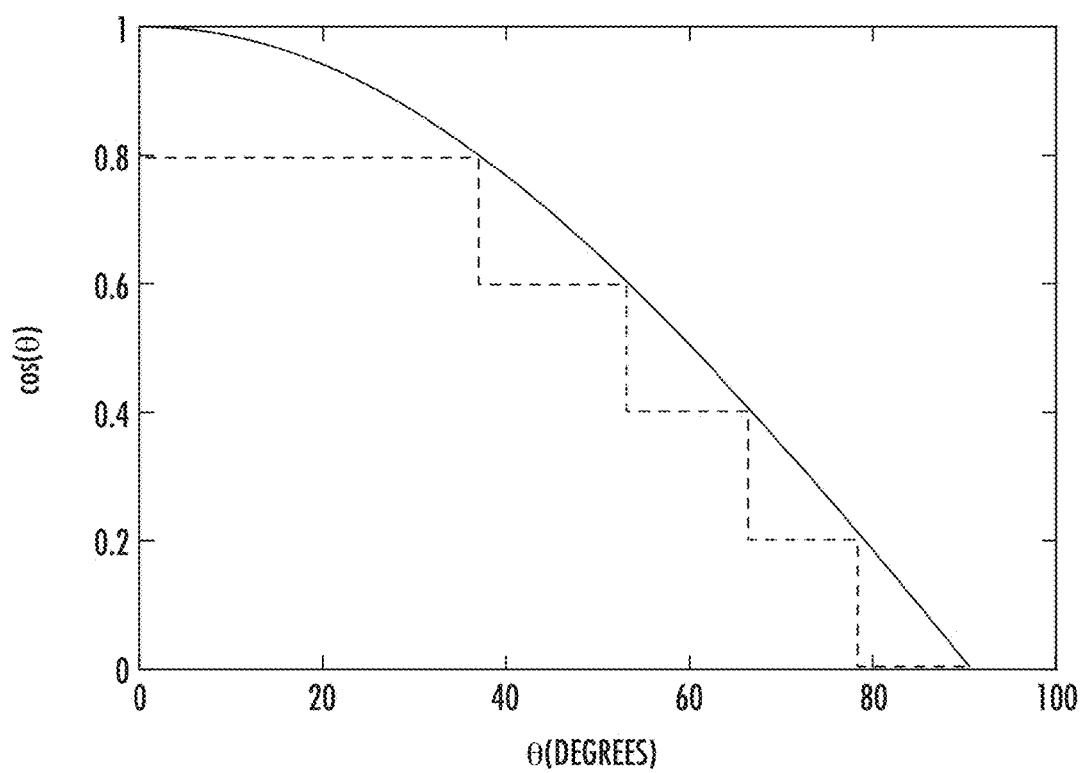
FIG. 11 is a plot wherein the solid line shows cos(θ) across the range of θ=0° to 90°, and the dashed line shows unitary stepwise (vertical) decreases in cos(6) and the associated (horizontal) increase in nominal θ.

FIG. 10B shows $\Delta\theta$ for each zero-volt angle case shown in FIG. 10A. For a given applied voltage, the magnitude of the nominal change in $\theta$ depends on $\theta_0$. For instance, 300 mV results in a 24° change when $\theta_0$=5° while the same voltage results in <10° change when $\theta_0$=450. Notably with DIBs, typical values for $\theta_0$ are closer to 25-35°, although it is clear that the zero-volt contact angle can be an important parameter affecting the electrowetting response described by the Young-Lippmann equation. The effect of initial contact angle on the total observed change in angle, for a given step in the cosine of the angle, is illustrated in FIG. 11.

Summary of Examples 1-7

The Young-Lippmann equation relates changes in contact angle to the applied voltage which affects the interfacial tension. In the DIB platform, where mechanical manipulation can be used to accurately measure $C_M$, and applied bias voltage induces measurable changes in contact angle, the Young-Lipmann relation provides a framework for simultaneous measurements of both monolayer and bilayer tension. The method is simple and involves measuring changes in the contact angle between droplets as applied bias voltage is increased. Contact angle alone is not sufficient for tension calculations as the Young-Lippmann equation includes membrane specific capacitance. However, specific capacitance is easily and precisely determined during the same test for tensions with droplets suspended on agarose-tipped electrodes. Knowledge of the shape (i.e. the circularity) of the interface can play a role in the accuracy of the measurement, particularly in light of observed droplet deformation due to gravity when there is a difference in densities of the oil and aqueous phases. Such density differences are encountered here with ≥200 nL droplets in tests using pure hexadecane or mixtures of hexadecane and silicone oil. Further, the presently disclosed subject matter indicates that the zero-Volt contact angle between droplets increases with increasing droplet area (as droplets are pushed together). However, while it was shown that values of monolayer tension do not appear affected by manipulation-induced changes to $\theta_0$, the nominal contact angle can affect the caculation of bilayer tension In both theory and practice, larger angle changes are obtained for lower $\theta_0$. This conclusion can allow tuning of the system (targeting $\theta_0 \le \theta_{eq}$) to achieve greater angle changes for the same voltage, which increases the signal-to-noise ratio of angle measurement.

With appropriate understanding of the shape of the interface, the presently disclosed subject matter demonstrates that the present procedure can exhibit comparable or better accuracy in measuring values of specific capacitance, bilayer tension, monolayer tension, and free energy of formation to methods described in the prior art. Further, all four physical properties can be measured in a single test over the course of 30 minutes or less. Further, there are several advantages of the DIB-Young-Lippmann approach over supported or painted lipid bilayer techniques:[18, 20] 1) forming bilayers between lipid coated droplets allows the area of the bilayer to be easily manipulated, which has been shown to enable accurate determination of specific capacitance; and 2) bilayer formation in a liquid environment (versus on a solid support) provides direct visual access to bilayer contact length and contact angle.

Measurements of $C_M$ (and thus $D_C$), $\gamma_b$, and $\Delta F$ support the conclusion that DPhPC DIBs formed in silicone oil:hexadecane mixtures are more solvent-free than DIBs formed in pure hexadecane or decane. Further, the solvent-free bilayers formed in silicone oil:hexadecane mixtures show an increased sensitivity to the effects of cholesterol on $C_M$, $D_C$, $\gamma_b$ and $\Delta F$. This conclusion suggests that, tuning oil composition to yield solvent-free bilayers could improve the ability to detect and quantify the effects of biomolecules, nanoparticles, peptides, or other species accumulating in lipid bilayers. The presently disclosed methods of measuring capacitance and tensions in a DIB also open the door to being able to study a wide variety of lipidic and non-lipidic species and their effects on membranes. An application of the presently disclosed method is the ability to characterize changes in bilayer physical properties driven by the incorporation of species (e.g. cholesterol) that, unlike transmembrane ion channels, do not elicit changes in membrane conductance. In some embodiments, the presently disclosed subject matter is employed in studies aimed at characterizing, monitoring, or sensing the interactions of a number of small molecules, peptides, pharmaceutic and therapeutic agents, or other lipophilic species with droplet interface bilayers.

Introduction to Examples 8-9

Biomimetic membranes comprised of amphiphilic phospholipids or polymers permit scientists to study a wide variety of processes that occur at or across cellular membranes. However, due to the fragility and short lifetimes (minutes to days) of phospholipid bilayers, scientists have aimed to create more robust membranes using polymerizable species, including phospholipids or polymers, and they have also looked to un-polymerized block copolymers that mimic the structure and amphiphilicity of lipids found in cellular membranes. Like lipids, amphiphilic block copolymers are known to self-assemble spontaneously into planar membranes, spherical vesicles called polymersomes, or rod-like structures in water, and yet they exhibit greater mechanical and chemical stability than lipids. In addition to a class of molecules called Janus dendrimers, diblock and triblock copolymers are the most commonly used types of amphiphilic polymers used to assemble biomimetic membranes. Diblock copolymers (i.e. those with an AB organization) include one hydrophilic polymer group attached to a hydrophobic group. With this architecture, diblock copolymers such as poly(etheylene oxide)-b-poly(ethylene ethylene) assemble to form 2-leaflet bilayer membranes in water, similar to the organization of phospholipids in lipid bilayers. Unlike diblocks, triblock architectures consisting of, for example, ABA or ABC block copolymers having hydrophilic end groups and a hydrophobic middle block can span the full thickness of the membrane they create. Representative ABA-format triblock copolymers can include hydrophilic poly(methyloxazoline) (PMOXA) end blocks and a hydrophobic poly(dimethyl siloxane) (PDMS) middle block. Notably, PMOXA-b-PDMS-b-PMOXA membranes exhibit greater stability than lipid membranes and they retain the ability to reconstitute functional protein channels and pores due to the elastic, fluid nature of the PDMS block that permits the hydrophobic interior to accommodate transmembrane proteins of varying lengths.

Planar freestanding copolymer membranes can be formed by painting a mixture of copolymer and organic solvent across the aperture of a solid support in water via the methods for forming black lipid membranes (BLMs). While this approach enables the assembly of a functional planar membrane, significant skill is required to initiate membrane thinning and this approach yields only one membrane per experiment. In contrast, as discussed herein above, droplet interface bilayers (DIBs) are planar bilayer membranes formed between lipid-coated water droplets immersed in oil. The DIB approach for membrane assembly is straightforward, allows for independent control of droplet and leaflet compositions, and uniquely enables the construction of multiple membrane networks, which have been shown to enable collective functionality, simply by adjoining more than two droplets. Thus, the ability to construct durable block copolymer membranes using the DIB approach could be used to develop new types of robust, compartmentalized materials for sensing, actuation, and energy harvesting. However, DIBs to-date have only been formed with phospholipids or single-tailed amphiphilic surfactants, for which it is known that the structures and sizes of these surfactant molecules play roles in adhesion properties of the membranes formed between droplets.

Spontaneous adhesion between surfactant-encased droplets and stabilization against coalescence, as observed with DIBs, are the result of a combination of intermolecular forces between surfactant (i.e. solute) and solvent molecules acting in the region between droplets. The term poor solvent describes a solvent where solvent-solvent or solute-solute contacts are preferred, rather than solute-solvent interactions; on the other hand, a good solvent is one in which solute-solvent interactions are more favorable than solute-solute interactions or solvent-solvent interactions. As a result, the portion of a surfactant (e.g. phospholipid or polymer chain) in the good solvent expands to maximize segment-solvent contacts, whereas it collapses to minimize these unfavorable interactions in poor solvent.

Adhesion between surfactant-coated water droplets is favored when the surrounding oil is a poor solvent for the hydrophobic region of the surfactant, which leads to the spontaneous exclusion of excess solvent from between droplets to form a solvent-free region. Entropic in nature, this exclusion generates an osmotic pressure that drives the droplets together (in addition to van der Waals attractive forces) to the point where short-range repulsive forces (steric in origin) between opposing surfactant monolayers stabilize adhesion and prevent coalescence. On the other hand, when the solvent is a good solvent for the hydrophobic coronae of the surfactant-coated water droplets, excluded volume interactions between surfactant tails and solvent molecules sterically stabilizes the droplets, preventing spontaneous solvent exclusion and droplet coalescence.

Examples 8 and 9 present the formation and characterization of fully reversible, voltage-activated copolymer stabilized droplet interfaces-which are referred to as copolymer stabilized interfaces (CSIs)-assembled between aqueous droplets coated in a monolayer of triblock copolymer molecules. The ABA triblock copolymer used in Examples 8 and 9 include poly(ethylene oxide) (PEO) end groups with a poly(dimethylsiloxane) (PDMS) middle group. Our results show that unlike prior studies (D. Wong, T.-J. Jeon and J. Schmidt, *Nanotechnology*, 2006, 17, 3710; D. Morton, S. Mortezaei, S. Yemenicioglu, M. J. Isaacman, I. C. Nova, J. H. Gundlach and L. Theogarajan, *Journal of Materials Chemistry* B, 2015, 3, 5080-5086), which demonstrated spontaneous thinning of planar triblock membranes in the presence of a poor organic solvent for the copolymer hydrophobic block, the use of PEO-b-PDMS-b-PEO-coated droplets immersed in good solvents for the middle block does not result in spontaneous membrane thinning and droplet adhesion. However, stable droplet adhesion and film formation is achieved when a voltage-induced compression is used to drive excess solvent from the hydrophobic regions of opposing triblock monolayers. Unlike spontaneous droplet adhesion, voltage-induced thinning is fully reversible: removing the applied voltage allows the droplets to completely separate as solvent returns to the region between droplets.

Examples 8 and 9 also describe a mechanism of reversible CSI formation between water droplets placed in various good solvents. More particularly, we perform experiments with the same copolymer dispersed in the organic solvents to investigate the role of solvent quality on voltage-driven exclusion and the resulting properties of the interface. In each solvent, we determine the minimum voltage required to initiate membrane thinning, and we utilize techniques disclosed herein with respect to lipid-based DIBs, to measure the specific capacitance and electrowetting response, which allow us to then determine the hydrophobic thickness and lateral tension of the CSI, respectively. These data allow us to investigate structural differences between lipid-based DIBs and CSIs, and our results show that planar copolymer membranes are considerably thicker than lipid DIBs due to solvent retention and polymer midblock length. Additionally, we observe that CSIs exhibit increased resistance to rupture during physical perturbation and significantly higher rupture potentials compared to DIBs. Simultaneously, CSIs also exhibit similar magnitudes of membrane resistance to ion transport as lipid bilayers even though they can exist in a lower tension state when formed in a silicone oil-based solvent. Thus, the ability to prevent coalescence/mixing between aqueous volumes and be reversibly connected and disconnected with voltage provides a new approach for membrane-based smart materials and reconfigurable droplet-based assays.

Materials and Methods Used in Examples 8-9

Five oil compositions are used in this study: n-decane, n-hexadecane, AR20 silicone oil, a 3:1 (v:v) mixture of hexadecane and AR20, and a 1:1 (v:v) mixture of hexadecane and AR20. All solvents, sodium chloride (NaCl), 3-(N-Morpholino)-propane-sulfonic acid (MOPS), sodium hydroxide (NaOH), and agarose (A9539) are acquired from Sigma Aldrich. PEO-b-PDMS-b-PEO (2 kDa-b-2 kDa-b-2 kDa, P7300-EODMSEO) triblock copolymer is obtained from Polymer Source Inc. 1,2-diphytanoyl-sn-glycero-3-phosphocholine (DPhPC) phospsholipid is obtained in powder form from Avanti Polar Lipids, Inc.

Copolymer-stabilized droplet interfaces are created between adjacent 200 nL droplets of aqueous buffer placed in a copolymer-oil mixture, or using the droplet-on-hydrogel bilayer method for forming a gel-supported CSI. For each oil type, PEO-PDMS-PEO triblock is incorporated into the oil at a concentration of 4 mg/ml, vortexed, and then stirred on a magnetic hot plate at a temperature of >60° C. to facilitate complete dissolution of the polymer. The application of heat ensures that the PEO end-blocks remain above their transition temperature (30° C.), as evidenced by obtaining a clear, homogeneous polymer-oil mixture. For comparison, DPhPC DIBs are formed in hexadecane between droplets containing 2 mg/mL unilamellar DPhPC liposomes (~100 nm) in aqueous buffer prepared via extrusion as described by W. L. Hwang, M. Chen, B. Cronin, M. A. Holden and H. Bayley, *J. Am. Chem. Soc.*, 2008, 130, 5878-5879 elsewhere. The aqueous buffer used in CSI and DIB experiments is 100 mM NaCl, 10 mM MOPS, balanced to pH 7.4 via titration with an identical solution supplemented with 0.5M NaOH. Buffer pH is verified using a Fisher Scientific Accumet pH probe. Liposome solutions are stored at 4° C. and are used within 2-3 weeks of preparation. Liposome-free aqueous buffer and polymer-oil solutions are stored at room temperature (23° C.), and polymer-oil solutions are reheated before tests to ensure complete dispersion of polymer in the oil phase. Note that only reported values of rupture potential for DPhPC DIBs in hexadecane are measured herein. All other reported values of DPhPC DIBs, including specific capacitance, thickness, contact angle, and monolayer and bilayer tensions, were sourced from other Examples disclosed herein. All DIB and CSI tests are performed at room temperature.

Electrical measurements and optical imaging are used collectively to assess adhesive interfaces between lipid- and copolymer-coated aqueous volumes in oil. The application of voltage and measurement of current across CSIs and DIBs are made using wire-type silver/silver chloride (Ag/AgCl) electrodes. Electrodes for DIB measurements are ball-ended as described by M. A. Holden, D. Needham and H. Bayley, *J. Am. Chem. Soc.*, 2007, 129, 8650-8655, whereas those for most CSI measurements lack a ball-ended tip and hydrogel coating, since these features complicate insertion of electrodes into polymer-encased droplets where the monolayer forms rapidly. In these experiments positive current represents flow of electrons into the headstage, and measurements are performed only at positive biases due to symmetric membrane compositions in all tests. Droplet positions are controlled manually via the electrodes; each electrode is attached to a 3-axis micromanipulator (KITE-R, World Precision Instruments). An AxoPatch200B and Digidata 1440A (Molecular Devices) are used to measure the square-wave current induced by a 10 mV, 10 Hz triangular voltage waveform generated by an Agilent 33210A function generator. Measurements of interfacial current are performed with grounded shielding placed near the positive electrode to minimize electromagnetic interference, and all measurements are sampled at 20 kHz and low-pass filtered with a 4-pole Bessel filter at 1 kHz. Side-by-side droplet pairs and droplets on a polymer-coated hydrogel surface are viewed through a 4× objective lens on an Olympus IX51 inverted microscope. Images are acquired with a QI Click CCD camera controlled using µManager 1.4.14 software (A. D. Edelstein, M. A. Tsuchida, N. Amodaj, H. Pinkard, R. D. Vale and N. Stuurman, 2014, 2014). Adhesive droplet images are post-processed in MATLAB to extract bilayer area for determining specific capacitance and contact angle for measuring interfacial tension and free energy.

Example 8

Voltage-Induced Adhesion of Triblock-Coated Droplets Placed in a Good Solvent

Figure 12B:
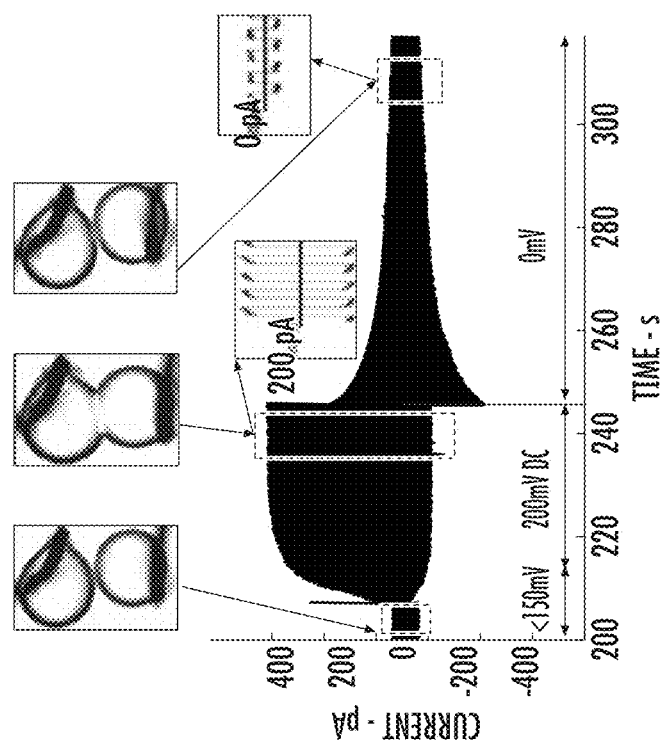
FIG. 12B is an image and plot showing voltage-induced thinning of a CSI in a 1:1 (v:v) hexadecane:AR20 mixture. Droplet diameters are ca. 700-800 µm.
Figure 12A:
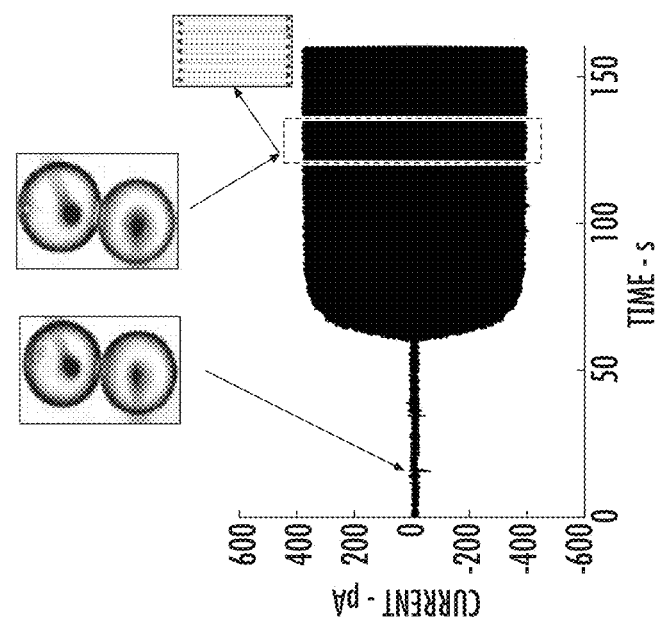
FIG. 12A is an image and plot showing spontaneous thinning of a DPhPC DIB in hexadecane.

CSIs and DIBs between adjacent aqueous droplets are prepared using a similar procedure with only very minor differences. In both CSI and DIB cases, aqueous droplets are pipetted into a less-dense nonpolar solvent and allowed to incubate for a short period of time (<30 s for droplets in copolymer-oil mixtures versus 2-5 min for liposome droplets in oil (W. L. Hwang, M. Chen, B. Cronin, M. A. Holden and H. Bayley, *J. Am. Chem. Soc.*, 2008, 130, 5878-5879)) to allow the amphiphiles time to self-assemble into monomolecular layers at the water-oil interfaces. Each adsorbed copolymer molecule is believed to be arranged in a looped configuration, i.e., with both hydrophilic endblocks in water and the hydrophobic midblock looping out into the oil. However, once droplets are brought into contact, the two systems show significant differences. Lipid-coated droplets FIG. 12A) spontaneously adhere upon the exclusion of excess solvent from between opposing lipid monolayers, as previously reported (H. Bayley, B. Cronin, A. Heron, M. A. Holden, W. L. Hwang, R. Syeda, J. Thompson and M. Wallace, *Molecular BioSystems,* 2008, 4, 1191-1208). Spontaneous thinning and subsequent growth of the lipid bilayer increases the interfacial electrical capacitance which results in a measurable increase in the amplitude of the squarewave current (FIG. 12A). We also observe a brighter, planar connection between adhered droplets (right inset) that is different from what is seen in adjacent, but disconnected droplets prior to the capacitive current increase (left inset). A 10 mV amplitude triangular voltage waveform is applied continuously to induce the squarewave current necessary for measuring interfacial capacitance; however, it is important to note that adhesion between lipid-coated droplets in hexadecane occurs even in the absence of electrodes and applied voltage. In contrast, PEO-b-PDMS-b-PEO-coated droplets in a 1:1 (v:v) mixture of hexadecane and AR20 silicone oil (as used elsewhere (G. Villar, A. J. Heron and H. Bayley, *Nat Nano,* 2011, 6, 803-808) to minimize density differences between the aqueous and organic phase) do not adhere spontaneously when placed in contact. The same result also occurs when aqueous droplets are placed in pure decane, hexadecane, or silicone oil.

Applied voltage can be used to expedite bilayer thinning in lipid-based DIBs. Therefore a voltage difference was applied between non-adhseive copolymer-coated droplets in 1:1 hexadecane:AR20 oil to see if adhesion could be also obtained for this system. The leftmost section of the current trace in FIG. 12B corresponds to separated droplets (see left inset image) despite the application of 150 mV (note, voltage was increased incrementally to this level). The background capacitive current in FIG. 12B is slightly larger than in FIG. 12A due to higher electrical noise during this experiment. In the next section of FIG. 12B (middle inset), increasing the voltage from 150 mV to 200 mV results in a sudden significant increase in the amplitude of the square-wave current response. Images obtained simultaneously show that there is a visible interface to accompany the increase in interface capacitance. The middle inset image shows that the droplets are clearly connected, sharing a large planar interface and a larger contact angle between droplets at a voltage of 200 mV. Finally, when the voltage is reduced to 0 mV, the capacitive current returns to its original amplitude and an image of the droplet pair shows that the droplets return to a separated state. This process is repeatable, and adhesion could be regenerated by increasing the applied voltage again to above 150 mV. Moreover, the area of adhesion between droplets can be reversibly varied by modulating the applied voltage at a level greater than the minimum required to drive adhesion (and quantified herein below). In summary, the voltage activated CSI's are manipulatable and reversible.

Figure 13:
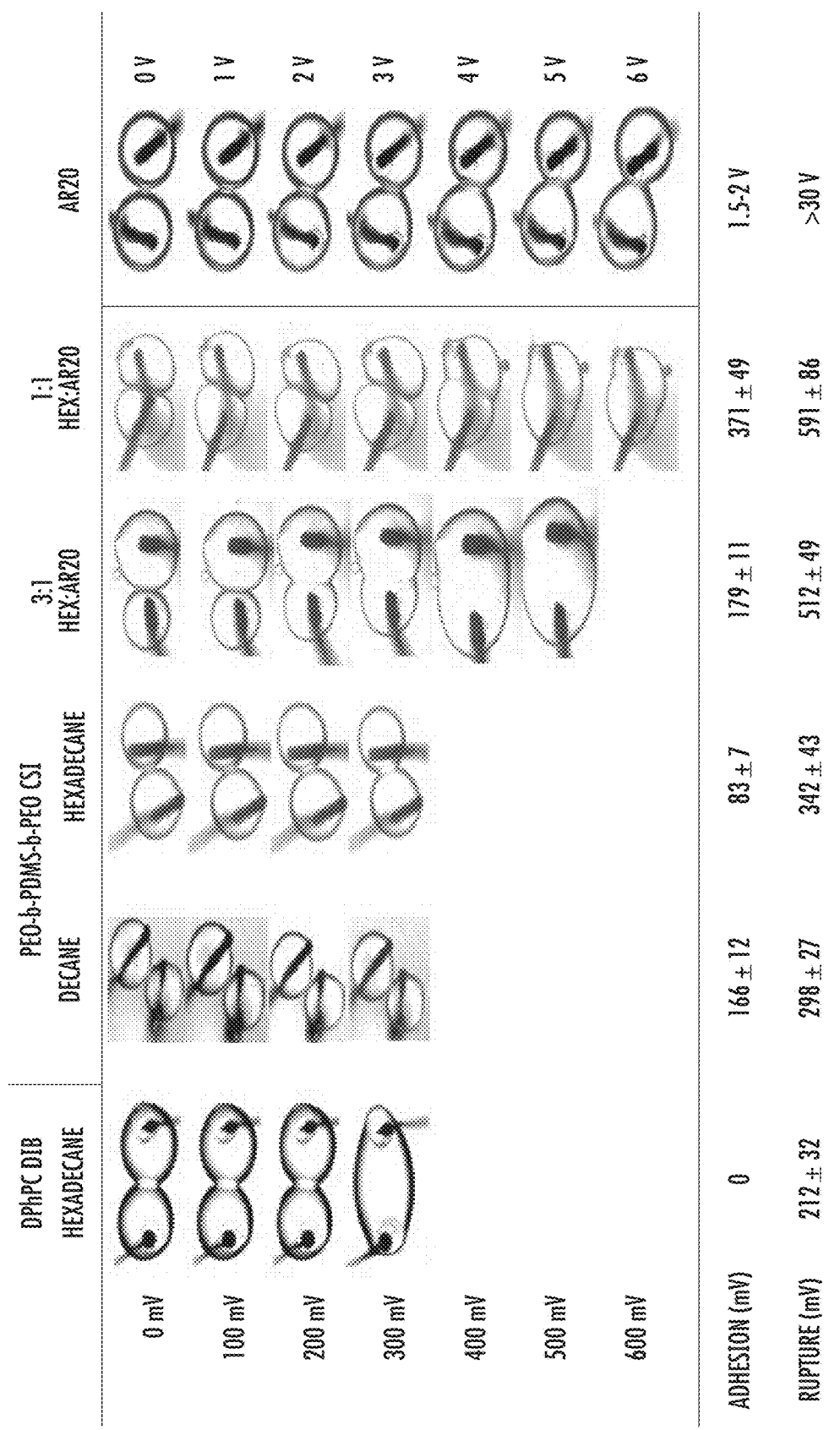
FIG. 13 is a table schematic showing DPhPC DIB versus voltage-induced CSI formation and rupture in different oils. Droplet diameters are ca. 700-800 µm (200 nL).

FIG. 13 shows that this same type of fully reversible, voltage-induced adhesion between droplets is also obtained for triblock-coated droplets placed in n-decane, n-hexadecane, a 3:1 (v:v) hexadecane:AR20 mixture, and pure AR20 silicone oil, each containing the same concentration (4 mg/mL) of PEO-b-PDMS-b-PEO copolymer. By incrementally increasing voltage in 20 mV steps, we determine that the average minimum voltage, $V_T$, required to initiate adhesion between droplets is 166 mV (n=5) in decane, 83 mV (n=5) in hexadecane, 179 mV (n=5) in 3:1 hexadecane:AR20 (n=5), 371 mV (n=5) in 1:1 hexadecane:AR20 (n=5), and >1V (n=5) in pure AR20. FIG. 13 also lists the rupture potential (the voltage at which the interface ruptures causing the droplets to coalesce) for a DPhPC DIB and for CSIs assembled in each solvent. Similar to the threshold potential for adhesion, we observe that CSIs assembled in oil mixtures containing AR20 silicone oil display higher rupture potentials than those obtained in alkanes. Interestingly, a rupture potential was not reached for applied voltages up to 30 V (the limit of our power supply) for CSIs contained in pure AR20. Further, the rupture potential values for CSIs tested here are all significantly higher than that (212 mV, n=7) found with DPhPC DIBs formed in hexadecane.

Example 9

Quantitative Characterization of Voltage-Induced CSIs

Figure 14A:
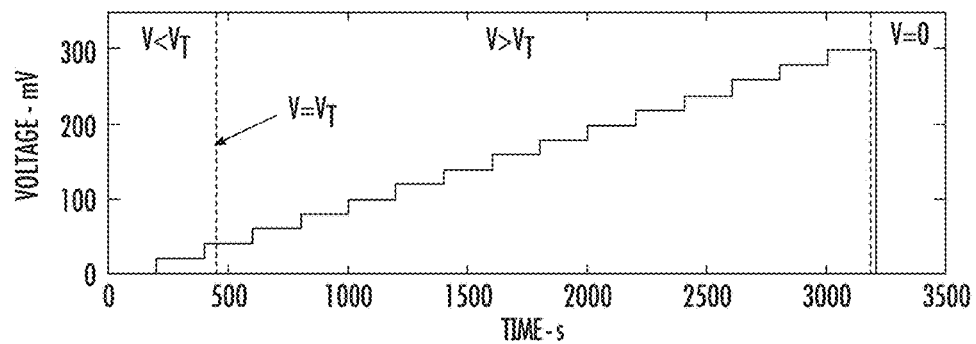
FIGS. 14A-14C are plots showing applied bias voltage (FIG. 14A) and the resulting CSI membrane capacitance (FIG. 14B); and resistance (FIG. 14C).
Figure 14B:
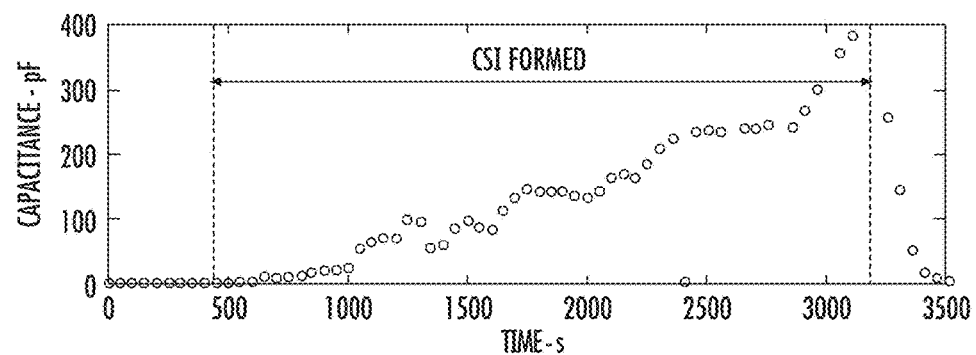
Figure 14C:
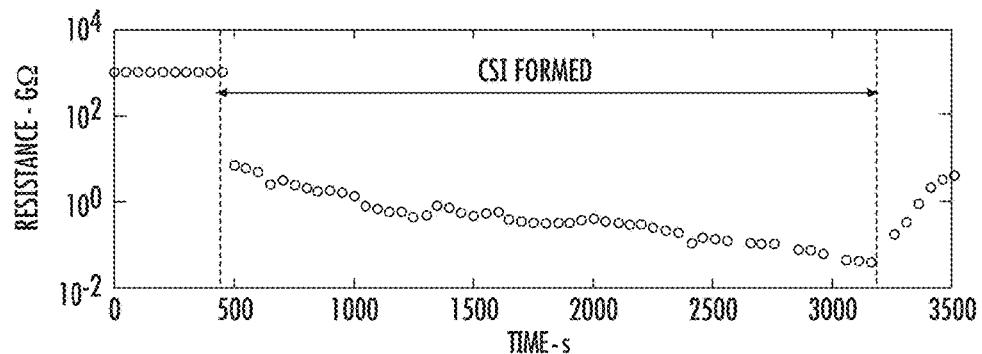

A lipid bilayer is commonly modeled as a resistor and capacitor wired in parallel (B. Hille, *Ion channels of excitable membranes*, Sinauer Sunderland, Mass., 2001). Therefore, to better understand the structures of CSIs and to evaluate their barrier properties, we measured the square-wave current induced by the sum of a 10 mV, 10 Hz triangle wave voltage and a dc bias varied between the adhesion threshold and rupture potential. Values for nominal membrane capacitance and resistance at each bias level are extracted from the current traces using a custom MATLAB script as described by B. Boreyko, G. Polizos, P. G. Datskos, S. A. Sarles and C. P. Collier, *Proceedings of the National Academy of Sciences*, 2014, 111, 7588-7593; A. J. Heron, J. R. Thompson, B. Cronin, H. Bayley and M. I. Wallace, *Journal of the American Chemical Society*, 2009, 131, 1652-1653. FIGS. 14A-14C show an example set of capacitance and resistance data obtained from the induced square-wave current measured while also applying a sequentially step-wise increasing bias potential (FIG. 14A) across a CSI in hexadecane. Reflecting the behavior seen in FIG. 12B for separated droplets, we observe that membrane capacitance is negligible and membrane resistance is maximum (our fitting routine permits a maximum value of 1000GΩ) until the bias reaches a value of approximately ~50 mV. However as applied potential exceeds $V_T$ (t~450s in FIGS. 14A-14C), nominal capacitance begins to increase and nominal resistance exhibits a sharp decrease to a value of ca. 40-50GΩ. The changes in these electrical properties coincide with formation of a planar adhesive connection between the droplets. The data in FIGS. 14A-14C show that additional increases in the bias potential cause the capacitance and resistance to continue to rise and fall, respectively. Finally, we observe these parameters rebound to the values of C and R observed when $V=V_T$ as the droplets detach upon returning the bias to zero. Resistance does not return to a value of 1000GΩ because of the non-linear nature of the fitting routine, which overestimates values of R prior to initial droplet adhesion.

These data pose interesting questions about the mechanism for changes in both capacitance and resistance as a function of the bias. Specifically, what causes the capacitance to increase: a change in area of adhesion, or a decreasing interfacial thickness, or both? Also, does the reduction in membrane resistance correspond to a voltage-dependent leakage, or is this change driven solely by changes in membrane area? To answer these questions, we performed a separate set of experiments with gel-supported CSIs assembled using the droplet-on-hydrogel (DHB) method (L. C. M. Gross, A. J. Heron, S. C. Baca and M. I. Wallace, *Langmuir*, 2011, 27, 14335-14342; J. R. Thompson, A. J. Heron, Y. Santoso and M. I. Wallace, *Nano Lett.*, 2007, 7, 3875-3878; A. J. Heron, J. R. Thompson, B. Cronin, H. Bayley and M. I. Wallace, *Journal of the American Chemical Society*, 2009, 131, 1652-1653). This approach allows us to accurately image the area of the interface while performing current measurements.

Figure 15A:
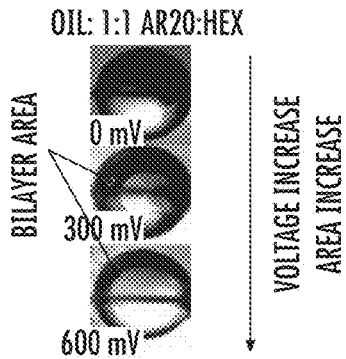
FIG. 15A is an image of a gel-supported CSI in 1:1 AR20:hexadecane, which shows the visible growth in adhesive area due to voltage.
Figure 15B:
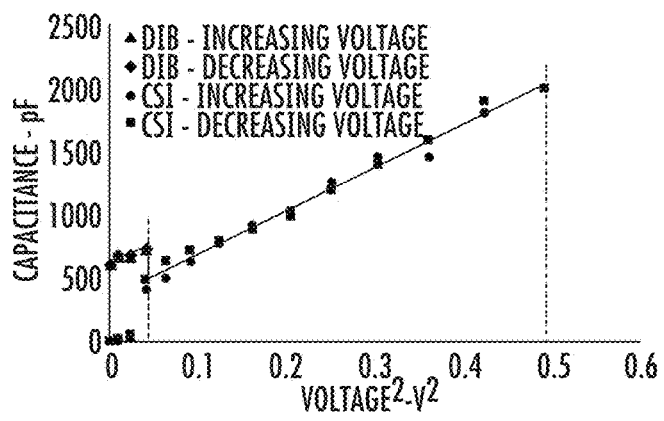
FIG. 15B is a plot showing nominal capacitance measured on a DPhPC DIB in hexadecane and a CSI in the same oil as in FIG. 15A versus the square of the applied bias. Data for a DIB with increasing voltage is shown with triangles. Data for a DIB with decreasing voltage is shown in diamonds. Data for a CSI with increasing voltage is shown in circles. Data for a CSI with decreasing voltage is shown with squares.
Figure 15C:
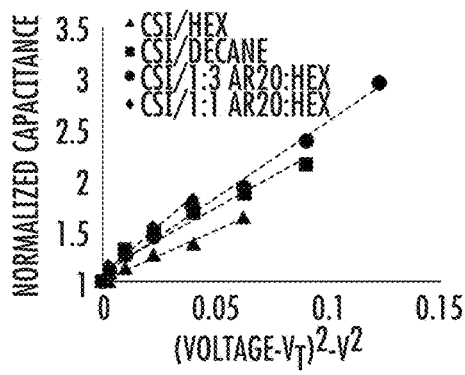
FIG. 15C is a plot showing normalized capacitance versus change in voltage squared for CSI in various hydrophobic medium: CSI in hexadecane, triangles; CSI in decane, squares; CSI in 1:3 AR20:hexadecane, circles; CSI in 1:1 AR20:hexadecane, diamonds.
Figure 15D:
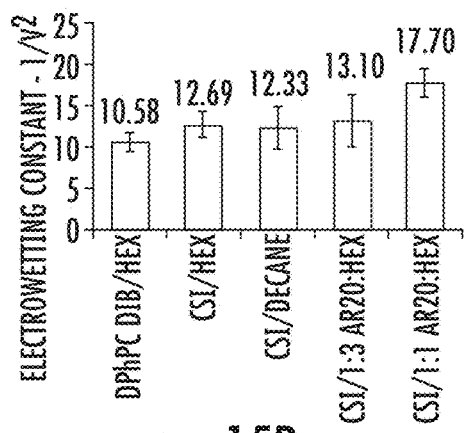
FIG. 15D is a bar graph showing the mean electrowetting constant after formation of the membrane for both a DPhPC DIB in hexadecane and CSIs in different oils.

FIG. 15A shows the visual changes in the adhesive region underneath a gel-supported polymer coated droplet in decane when the voltage is increased from 0 mV to 300 mV; the arrows indicate the perimeter of the adhesive region (i.e., the CSI). Note, the DHB method for CSI formation is utilized here due to the extremely low monolayer tensions of polymer-coated droplets in oil that complicates the calculation of bilayer area using images of adjacent, sagging droplets. Plotting the measured capacitance versus the square of the bias voltage (FIG. 15B) shows that the capacitance of the CSI exhibits a sharp increase at the threshold potential (~200 mV) and then increases linearly with respect to voltage squared. This trend is indicative of electrowetting behavior observed at capactive liquid interfaces as has been quantified for DIBs elsewhere herein, for example. For comparison, the voltage-dependent change in membrane capacitance for a DPhPC DIB (~30% increase) is provided in FIG. 15B to emphasize the much larger change (~400%) in membrane capacitance relative to nominal capacitance measured at $V_T$ observed for the CSI. Repeating this experiment for CSIs in different oils shows that normalized membrane capacitance (relative to capacitance at $V_T$) varies linearly with respect to the square of the voltage difference between the bias potential and the threshold potential for that oil type (FIG. 15C). The slopes of the curves for each oil type in FIG. 15C represent the electrowetting constant, a, which describes the voltage-sensitivity of a capacitive interface. The bar graph in FIG. 15D compares the average values of electrowetting coefficient for CSIs formed in different oils (n=3 in each oil) to that for DPhPC DIBs formed in hexadecane. All values range from 10-20 $V^{-2}$, and the data show that the strength of CSI electrowetting increases with the fraction of silicone oil in the nonpolar solvent surrounding droplets.

Figure 16A:
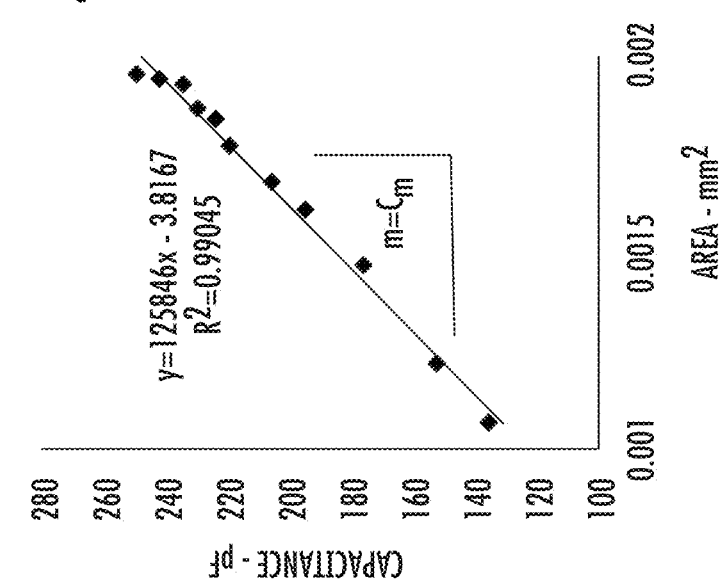
FIGS. 16A-16C are a series of plots and bar graphs showing representative nominal capacitance versus adhesive area data obtained for a CSI formed in 1:1 AR20:hexadecane. This type of data for each interface allows calculation of the average specific capacitance (FIG. 16B) and equivalent membrane thickness (FIG. 16C).
Figure 16B:
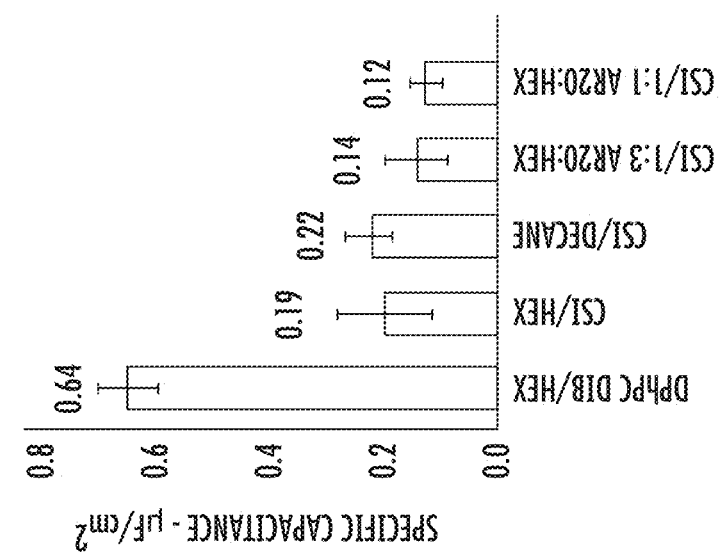

FIG. 16A shows the steady-state capacitance determined from the squarewave current magnitude, plotted versus the optically measured interfacial area of a CSI formed in 1:1 hexadecane:AR20. Unlike lipid-based DHBs which enable control of membrane area by changing the vertical position of the droplet (L. C. M. Gross, A. J. Heron, S. C. Baca and M. I. Wallace, *Langmuir*, 2011, 27, 14335-14342; J. R. Thompson, A. J. Heron, Y. Santoso and M. I. Wallace, *Nano Lett.*, 2007, 7, 3875-3878; L. C. M. Gross, O. K. Castell and M. I. Wallace, *Nano Letters*, 2011, 11, 3324-3328), these data reflect variations in membrane area caused by changing the applied bias voltage. Attempts to lift droplets with an electrode resulted in the droplets falling from the probe due to the low surface tension of copolymer-encased droplets. Yet, similar to a DIB (see other data presented elsewhere herein, for example), we find that nominal capacitance varies linearly with interfacial area. The slope of the capacitance-area curve, which for this oil type has a value of 0.126 $\mu F/cm^2$, represents the specific capacitance, $C_m$, as given by:

$$C_m = \frac{C}{A} = \frac{\varepsilon_r \varepsilon_0}{t}, \qquad \text{Equation 10}$$

where $\varepsilon_r$ is the relative permittivity of the hydrophobic region of the membrane, $\varepsilon_0$ is the dielectric permittivity of vacuum (8.85×10$^{-12}$ F/m), and t is the hydrophobic thickness of the membrane. Linear relationships between nominal capacitance and interface area are also found for the other oils (not shown; $C_m$ cannot be determined in pure silicone oil due to the voltage limit of our current measurement device). The linearity of these data indicate that for $V > V_T$, voltage-driven increases in CSI capacitance are explained fully by increases in interfacial area at constant hydrophobic thickness (i.e. $C_m$ is not voltage dependent). As shown in FIGS. 15A-15D, these electrowetting-driven increases in membrane area range from 150-400% for CSIs, which is considerably higher than what we observe for a DPhPC lipid bilayer in hexadecane (~30%). FIG. 16B compares the average values of $C_m$ measured for CSIs in various oils. Compared to a DPhPC DIB in hexadecane, CSIs exhibit much lower values of $C_m$. Moreover, we observe that CSIs formed in oils containing silicone oil exhibit slightly lower values of $C_m$ than those formed in alkanes.

Figure 16C:
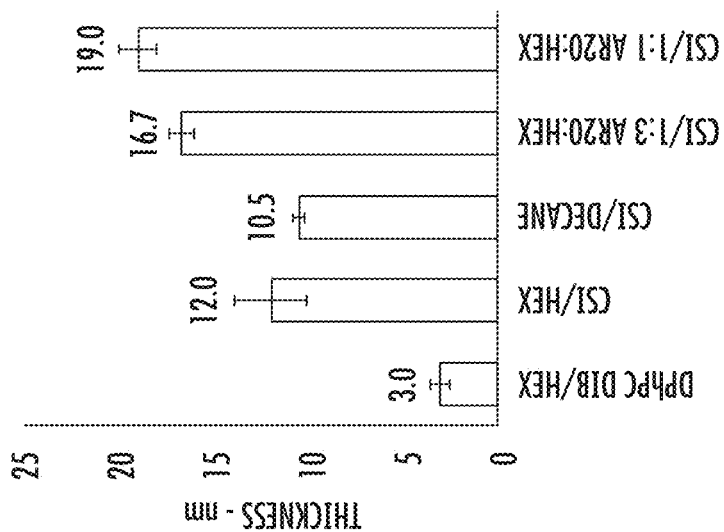

The hydrophobic thickness for each CSI is determined from these values of $C_m$ using Equation 10 and shown in FIG. 16C. The calculation is performed by using a value of $\varepsilon_r$=2.6 to describe the dielectric properties of the triblock copolymer interface hydrophobic region ($\varepsilon_r$ for PDMS ranges from 2.3-2.8 eds. J. Brandrup, E. H. Immergut and E. A. Grulke, N.Y.: Wiley-Interscience, New York, Editon edn., 1999; M. B. H. Othman, M. R. Ramli, L. Y. Tyng, Z. Ahmad and H. M. Akil, *Materials & Design*, 2011, 32, 3173-3182). It is noted that thinned CSIs may contain some residual amount of solvent as with lipid bilayers (S. H. White, *Nature*, 1976, 262, 421-422; S. H. White, *Biophys. J.*, 1978, 23, 337-347), and the relative permittivity of alkanes like decane and hexadecane tends to be closer to 2.2 (G. Valincius, F. Heinrich, R. Budvytyte, D. J. Vanderah, D. J. McGillivray, Y. Sokolov, J. E. Hall and M. LOsche, *Biophysical Journal*, 2008, 95, 4845-4861), thus our approximation could slightly overestimate hydrophobic thicknesses (especially in cases where pure alkanes are used, since AR20 and PDMS are expected to both have a dielectric permittivity of ~2.6). Nonetheless, these calculations show (FIG. 16B) that the reduction in $C_m$ for CSIs compared to a DIB ($\varepsilon_r$=2.2) is the result of the interface having a considerably thicker hydrophobic region (10-20 nm). These data also show that CSIs in alkanes are thinner than those in silicone oil mixtures, which suggests that CSIs formed in alkanes contain less residual solvent upon voltage-initiated adhesion. Measured thickness values also compare well to those predicted for polymer brushes with 100% surface coverage described by the Alexander-deGennes model (Israelachvili, *Intermolecular and Surface Forces* (3$^{rd}$ Edition), Academic Press, Saint Louis, Mo., USA, 2011).

$$L \approx Na. \qquad \text{Equation 11}$$

Here L represents the height (or thickness) of the "brush," which in this case is comprised of the hydrophobic PDMS middle block extending into the oil, N is the number of PDMS segments, and a is the segment length. A 2 kDa PDMS block consists of approximately 28 repeat units; however we estimate N as being at most 14 segments in length to account for the fact that the copolymer likely resides in a looped configuration at the oil-water interface due to the ABA design of the triblock copolymer (X. Wang, J. L. Davis, J. P. Hinestrosa, J. W. Mays and S. M. Kilbey, *Macromolecules*, 2014, 47, 7138-7150; J. Alonzo, J. W. Mays and S. M. Kilbey Ii, *Soft Matter*, 2009, 5, 1897-1904). With a value of 0.6 nm for the segment length from literature (G. Beaucage, S. Sukumaran, S. J. Clarson, M. S. Kent and D. W. Schaefer, *Macromolecules*, 1996, 29, 8349-8356), L is estimated to be 8.4 nm. Therefore, a bilayer formed between co-polymer droplets displays a hydrophobic thickness on the order of ~17 nm. These values (8.4 nm and 17 nm) represent the limiting situation where the PDMS chains of the membrane are laterally crowded such that they are maximally extended into the oil. In oils where PDMS is less soluble or chains less crowded, we expect the brush height and total membrane thickness to be reduced due to the fact that the PDMS blocks would prefer to reside in a more compact, less swollen state. The differences between the measured values of hydrophobic thickness and the predicted total membrane thickness may also be the result of inclusion of oil in the midplane, which can occur in planar lipid bilayers formed in oil (T. J. McIntosh, S. Simon and R. MacDonald, *Biochimica et Biophysica Acta (BBA)-Biomembranes*, 1980, 597, 445-463).

Figure 17B:
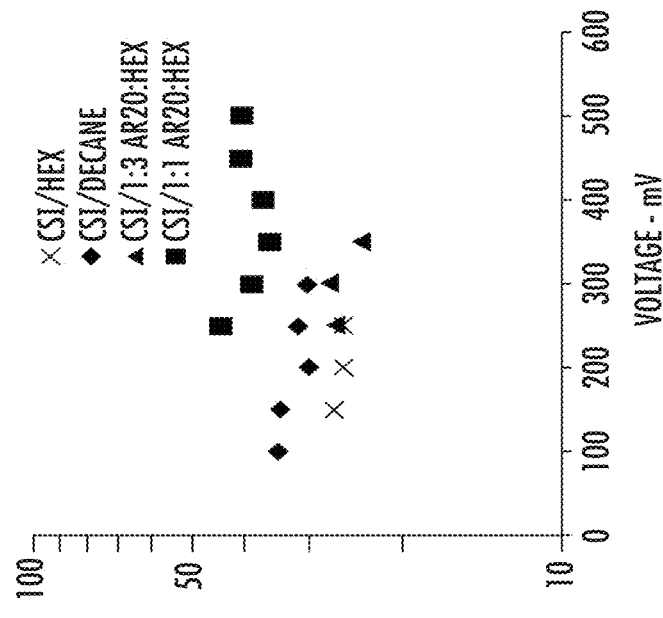
FIG. 17B is a plot showing membrane resistance versus nominal voltage ($V>V_T$) of CSIs in various solvents: hexadecane (Xs), decane (diamonds), 1:3 AR20:hexadecane (triangles), and 1:1 AR20:hexadecane (squares)
Figure 17A:
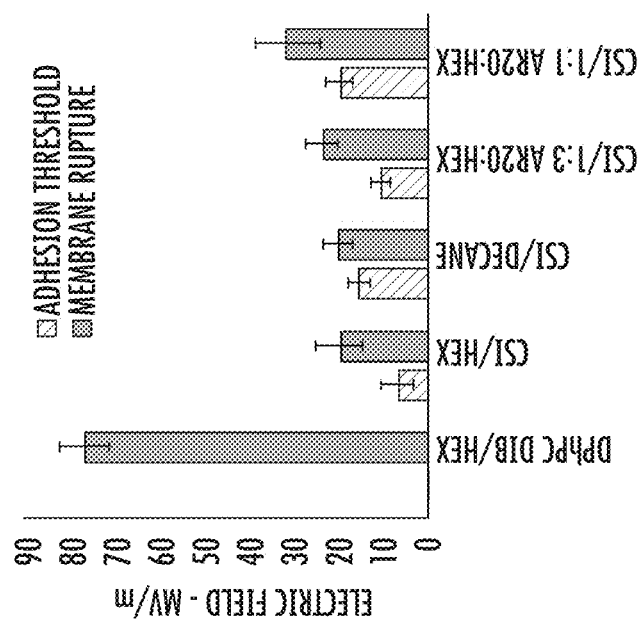
FIG. 17A is a bar graph showing computed electric field at both adhesion threshold (striped bars) and rupture voltages (gray bars) for a DPhPC DIB in hexadecane and for CSIs under different solvents.

With values of thickness known for CSIs in different oils, we next computed the magnitudes of electric field required to initiate adhesion and cause rupture (FIG. 17A). These data are again compared to that for a DPhPC DIB, and we see that despite the higher rupture potentials for CSIs, the electric field required to rupture a DPhPC bilayer is approximately 2-3× higher than that which is required to cause rupture in the triblock-stabilized interfaces. Examination of the raw current measurements made on CSIs at voltages near the rupture potential shows that the applied voltage causes transient increases in current shortly before an irreversible increase in current that coincides with membrane rupture and droplet coalesence. This observation, which we also observe in lipid bilayers, suggests the applied voltage causes electroporation of CSIs, which leads to membrane rupture.

Finally, values of membrane resistance ($R_m$=R×A) are computed by multiplying the measured resistance of a CSI by its respective area (determined by dividing nominal capacitance by $C_m$) at every bias voltage (FIG. 17B). Despite CSIs exhibiting far lower values of nominal resistance (0.2-2 GΩ) than lipid bilayers (10-100GΩ), values of CSI membrane resistance on the order of 20-30MΩ cm$^2$ are quite similar in magnitude to those for lipid bilayers (10-100MΩ cm$^2$). Additionally, we see that the membrane resistance of each CSI-oil combination is generally constant versus voltage, and thus interfacial area. As a result, we can interpret the decrease in nominal resistance observed in FIG. 14C as being due primarily to the increase in area, and not due to voltage-initiated permeation. The permeability of this type of membrane to species other than ions is still largely untested, however a preliminary experiment demonstrated that carboxyfluoroscein does not diffuse through a CSI formed (with V>$V_T$) in a 1:1 mixture of hexadecane:AR20.

While the results described thus far show how voltage affects CSI thickness and interdroplet contact area, little is known about the organization of triblock molecules and thus the tension states for both monolayer and the adhesive interface of a CSI. Knowledge of the monolayer and interfacial tensions of droplet-supported CSIs assembled in different oils would shed light on the mechanism for voltage-initiated adhesion, specifically pertaining to the role of solvent. Initially, we attempted to measure the monolayer tension of a triblock-covered water droplet in oil using a pendant drop goniometer. However, we observed the droplet to quickly sag in the less dense oil and then fall from the dispensing tip, which prevented us from being able to determine steady-state monolayer tension using the conventional pendant drop method.

As disclosed elsewhere herein, the steady-state monolayer tension of a DIB can be measured by tracking the electrowetting response of an interface for which $C_m$ is known. The method is based on the Lippmann relationship (J. Requena and D. A. Haydon, *Journal of Colloid and Interface Science*, 1975, 51, 315-327) which states that upon application of voltage across the capacitive bilayer interface, bilayer tension, $\gamma_b$, is reduced by the magnitude of the energy stored at the interface due to capacitive charging as given by $$\gamma_{b,0} - \gamma_b(V) = \frac{C_m}{2}V^2, \qquad \text{Equation 12}$$

where $\gamma_{b,0}$ is the bilayer tension at zero volts, $C_m$ is the specific capacitance of the interface, and V is the applied voltage. For adhesive droplets that exhbit a planar interface and an external half contact angle, θ, $\gamma_b$ is related to the monolayer tension, $\gamma_m$, via Young's relationship which is given by $$\gamma_b = 2\gamma_m \cos\theta. \qquad \text{Equation 1}$$

For a DIB that forms spontaneously at a zero bias, combining Equations 4 and 5 produces an expression that relates the change in the cosine of the contact angle to $C_m$, $\gamma_m$, and V. However, because CSIs exhibit electrowetting only at non-zero biases, Equations 12 and 1 are rewritten as $$\cos\theta_{ref} - \cos\theta(V) = \frac{C_m}{4\gamma_m}(V^2 - V_{ref}^2) \qquad \text{Equation 13}$$

to reflect how the cosine of the contact angle changes with respect to $\theta_{ref}$, defined as the external contact angle measured at a non-zero reference bias $V_{ref}$ located above the threshold potential.

Figure 18A:
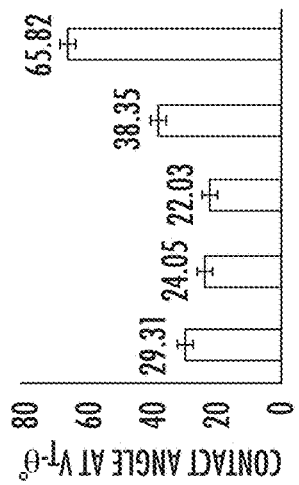
FIGS. 18A-18E are a series of plots and graphs showing the change in cosine of contact angle versus voltage squared for (FIG. 18A) CSIs in hexadecane (Hex, triangles) and decane (squares), and (FIG. 18B) for CSIs in 1:3 AR20:Hex (circles) and 1:1 AR20:Hex (diamonds).
Figure 18B:
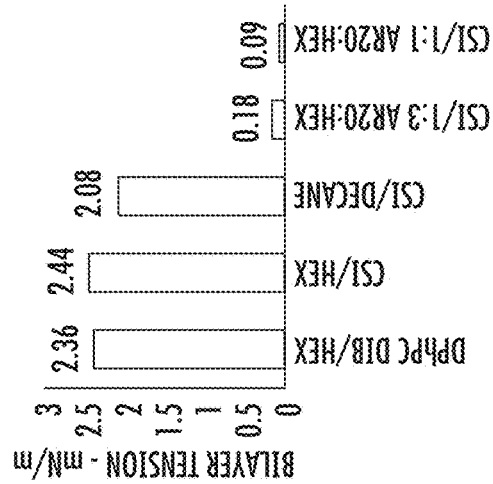
Figure 18C:
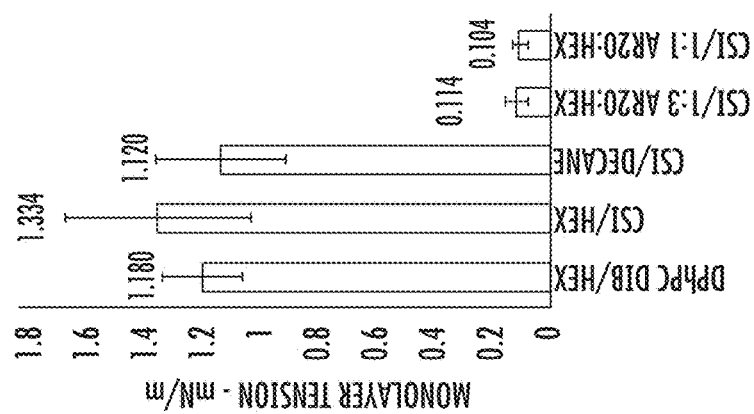

Since $C_m$ is known for the CSIs in various solvents, Equations 13 and 1, respectively can be used to determine unknown values of $\gamma_m$ and $\gamma_b$ by measuring the change in the cosine of θ versus the change in V$^2$. Therefore, a final series of experiments was performed on CSIs formed between adjacent droplets to investigate how the contact angle between droplets changes with the bias. FIGS. 18A and 18B show representative data for the measured change in the cosine of the contact angle versus (V$^2$—V$_{ref}^2$) for CSIs in each oil. The data are plotted on separate axes to account for the difference in scale between the values obtained for CSIs in alkanes versus those in silicone oil mixtures. All curves display a generally linear relationship between change in cosine of the contact angle and the difference in the square of the applied bias; R$^2$ correlation coefficient values for all curves are greater than 0.89, and greater than 0.96 for CSIs in silicone oil mixtures. In total, data were obtained from three separate interfaces formed for each CSI-oil combination. With Equation 13 and the corresponding average value of $C_m$ for each CSI-oil (FIG. 16A), the slope of each linear regression is used to calculate $\gamma_m$. FIG. 18C compares the average monolayer tensions of CSIs to that measured on a DPhPC DIB. Interestingly, while the monolayer tensions for CSIs in alkanes are similar in magnitude to that for a DPhPC monolayer (~1-1.3 mN/m (G. A. Venkatesan, J. Lee, A. B. Farimani, M. Heiranian, C. P. Collier, N. R. Aluru and S. A. Sarles, *Langmuir*, 2015, 31, 12883-12893)), these data show that copolymer monolayers at a water-silicone oil mixture interface are considerably lower (~0.1 mN/m).

Figure 18D:
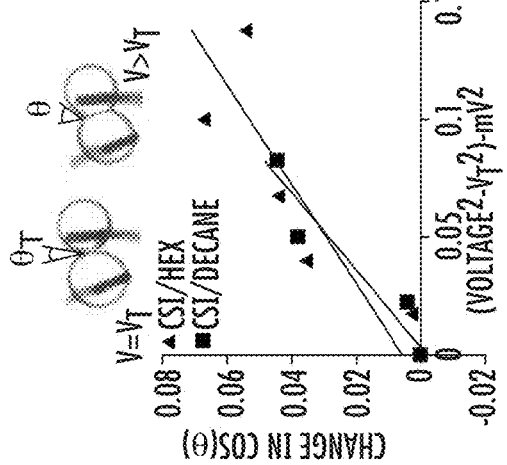
Figure 18E:
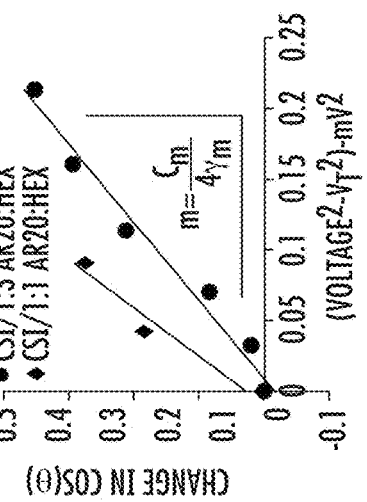

Average values for $\gamma_b$ at $V_T$ are computed for each CSI-oil case via Young's equation (Equation 1). $\gamma_m$ was computed for each in the previous section, and the contact angle, $\theta_t$, measured at $V_T$ is measured from images taken of adhered droplets after equilibration at $V_T$. Resulting values of $\theta_t$ and $\gamma_b$ are shown in FIGS. 18D and 18E for all CSIs and a DPhPC DIB. As observed with $\gamma_m$, these data again show that CSIs in alkanes exhibit membrane tensions (~2.0-2.5 mN/m) similar in magnitude to a lipid DIB, due to both similar values of monolayer tension and contact angle (20-30°). However, CSIs formed in silicone oil mixtures, those which display very low monolayer tensions, have substantially larger contact angles and thus even smaller relative membrane tensions (<0.2 mN/m). The Lippman (Equation 12) and Young (Equation 1) relationships predict that these interfaces reach an even lower tension, which corresponds to a higher contact angle, due to electrowetting at higher biases. This behavior is confirmed indirectly by the increasing contact angle observed with increasing voltage prior to rupture (FIG. 13). In fact, some of these interfaces approach an external half angle of 90°, which signifies the membrane reaches a zero-tension state.

Figures 19A, 19B:
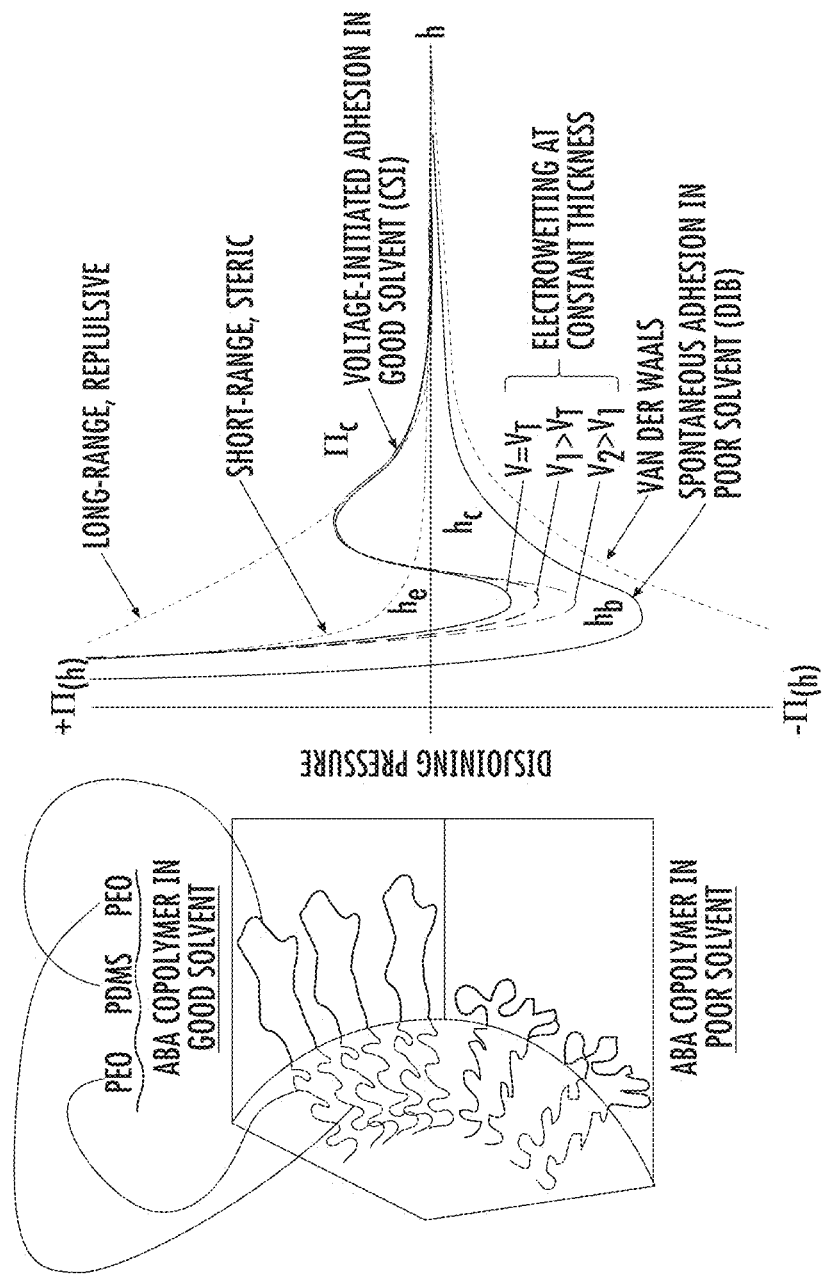
FIG. 19A is an illustration of conformations of copolymer molecules at the water-oil interface in good and poor solvents.
FIG. 19B is a plot showing qualitative disjoining pressure profiles versus separation distance for voltage-initiated CSI membranes formed in good solvents and DIBs assembled in poor solvents.

These findings confirm why polymer-coated droplets consistently fell from the syringe tip during goniometer trials (extremely low $\gamma_m$), but they also reveal important differences about molecular packing at the interface. Specifically, the difference in tensions for CSIs in alkanes versus silicone oil mixtures suggest that copolymer molecules, likely in a looped configuration at the oil-water interface, are packed more tightly when the solvent contains silicone oil. Building on analysis by P. G. de Gennes, *Macromolecules,* 1980, 13, 1069-1075, we interpret the reduced tension and increased thicknesses of CSIs in silicone oil mixtures to confirm that the hydrophobic-PDMS middle block, which likely resides in a looped configuration at the oil-water interface, is extended from the interface but tightly packed in a lateral direction which serves to more effectively minimize the interfacial tension. In alkanes, our data suggest that the molecules are arranged in a more expanded state laterally, and they are also less swollen by solvent, which results in a shorter height-thus alkanes are relatively poorer solvents for PDMS expansion but still sufficiently good, which prevents spontaneous droplet adhesion. FIG. 19A shows a qualitative representation of these differences in molecular arrangement.

Discussion of Examples 8-9

Mechanism of Reversible, Voltage-Initiated Adhesion and CSI Stability

Examples 8 and 9 highlight key differences between the adhesion behavior and stability of DIBs and CSIs. DPhPC-coated droplets adhere spontaneously in hexadecane as well as in decane and silicone oil, confirming that these oils acts as poor solvents for the acyl chains of the DPhPC monolayers (P. Poulin and J. Bibette, *Langmuir,* 1998, 14, 6341-6343). In a poor solvent, solvent is excluded due to unfavorable interactions, creating a solvent-depleted region of contact between droplets. This causes the area of the solvent-depleted region and the contact angle between droplets to scale inversely with tail solubility in the oil, which has been previously demonstrated: DPhPC DIBs formed in dodecane (S. Punnamaraju and A. J. Steckl, *Langmuir,* 2010, 27, 618-626), a smaller-molecule solvent in which the acyl chains have greater solubility, have a significantly smaller contact area compared to lipid-coated droplets connected in silicone oil (A. R. Thiam, N. Bremond and J. Bibette, *Langmuir,* 2012, 28, 6291-6298).

Like DIBs, polymer-coated droplets in alkane and silicone oil mixtures do not coalesce when placed in contact. However, unlike DIBs, they required a bias voltage to form an adhesive connection since the exclusion of oil is not favored, and they fully separate when this voltage is removed due to steric repulsion between opposing looped chains decorating the interface. The images and table in FIG. 13 highlight that the minimum voltage required to cause adhesion depends on the type of oil surrounding the droplets and that it increases for silicone-based oils versus pure alkane mixtures and with decreasing alkane length (i.e. decane versus hexadecane), a trend that is also observed in lipid bilayers (D. Needham and D. A. Haydon, *Biophys. J.,* 1983, 41, 251-257). This finding indicates that silicone oil is a better solvent than the two alkanes tested herein. In addition to the minimum voltage required to initiate adhesion, our knowledge of DIB area versus alkane length leads us to expect that the contact area of a voltage-thinned CSI at the threshold would scale inversely with solvent solubility. The images of CSIs in decane and hexadecane in FIG. 13 demonstrate this trend: CSI formation in decane, which appears to be a better solvent for PDMS, results in a smaller interfacial area at voltages above the threshold compared to the larger, more-easily excluded hexadecane. However, the fact that very low droplet surface tensions were obtained with solvents containing silicone oil allowed the droplets to assume a flattened, non-spherical shape. As a result, the images in FIGS. 12A, 12B and 13 may not provide an accurate trend of relative bilayer size versus droplet radius for all oils tested. In a separate experiment, we studied the interactions of droplets coated with PEO-b-PDMS-b-PEO in a mixture of chloroform, hexadecane, and squalene at a volume ratio of 0.1:0.8:3.2. In this sufficiently poor solvent, we observed droplets to spontaneously adhere without voltage.

Together, these findings confirm that the relative solubility of the hydrophobic copolymer middle block in an oil dictates the adhesion response of adjacent triblock-coated droplets. Our understanding of the mechanism of reversible, voltage-initiate adhesion for triblock polymer-coated droplets immersed in a good solvent is explained in the framework of the disjoining pressure. The disjoining pressure for reversible CSI formation in good solvent is illustrated qualitatively in FIG. 19B (black trace) as a function of separation distance, h, between two polymer-coated droplets, and this relationship is compared to that for spontaneous adhesion between surfactant-coated droplets in a poor solvent such as is observed with DIBs (gray trace).

As two droplets approach one another at large values of h, long-range repulsive interactions develop due to the presence of swollen polymer chains extending into the oil from each droplet surface. These interactions between polymer "brush" layers are entropic in nature and stem from a combination of osmotic repulsion interactions between solvated polymer coils which favors their expansion and the energy required to elastically stretch these chains (J. N. Israelachvili, *Intermolecular and Surface Forces* (3rd Edition), Academic Press, Saint Louis, Mo., USA, 2011). The net effect is a repulsive barrier that prevents spontaneous adhesion. The application of voltage works to compress the thick interface and acts in opposition to these repulsive interactions, where the magnitude of the electrocompression (Z. Liu, S. T. Chan, H. A. Faizi, R. C. Roberts and H. C. Shum, *Lab on a Chip,* 2015, 15, 2018-2024) is given by $$\prod(h) = \frac{1}{2}\varepsilon_r\varepsilon_0\left(\frac{V}{h}\right)^2. \qquad \text{Equation 14}$$

This applied pressure thins the interface through both elastic compression of the chains and through hydraulic exclusion of solvent from the interface. As applied voltage increases above zero but remains below the voltage threshold for adhesion, the system moves stably up the disjoining pressure curve (from right to left in FIG. 19B). A critical thickness is reached as soon as voltage reaches $V_T$, whereupon the interface spontaneously transitions to an adhesive interface like those shown in FIGS. 12A, 12B and 13. This metastable point exists at a medium-range critical separation distance, denoted as $h_c$, where the electrocompressive forces cancel the long-range repulsive interactions, thereby thinning the interface, such that medium-range attractive van der Waals interactions between the two droplets now become the dominate forces balancing the system. This metastable balance point, denoted as $\Pi_c$ thus represents the peak of the repulsive barrier before the two droplets transition spontaneously into an adhered state with an equilibrium thickness, $h_e$ (FIG. 19B). The onset of adhesion is depicted as a reduction in the net disjoining pressure to a net negative value, and, importantly, is verified experimentally by the observed increase in contact angle between droplets when the voltage is increased above the threshold. Adhesion can be quantified by measuring or calculating the reduction in free energy per unit area of the system upon the formation of the adjoining interface (D. Needham and D. A. Haydon, Biophys. J., 1983, 41, 251-257) as given by $$-\Delta F(V) = 2\gamma_m - \gamma_b(V) = 2\gamma_m(1 - \cos\theta_v) \quad \text{Equation 15}$$

Equation 15 is written as a function of the applied voltage to emphasize that membrane tension is a function of applied voltage when electrowetting occurs. Once driven to an adhesive state, our measurements of $C_m$ and thickness confirm that increasing the voltage further ($V > V_T$) only changes the area of the interface at constant thickness via electrowetting. The effect of electrowetting on the disjoining pressure is shown using dashed lines to illustrate the reduction in the local minimum at the equilibrium thickness, $h_e$.

In summary, applying voltage between polymer-coated droplets immersed in a sufficiently good solvent does work to overcome the positive disjoining pressure necessary for expelling solvent and compressing the interface. The interface thins stably as the voltage is increased up to a critical distance, $h_e$, at which spontanous, attractive van der Waals interactions drive the droplets together to form an adhesive connection. Unlike recent reports of surfactant-coated droplets that coalesce under voltage (Z. Liu, S. T. Chan, H. A. Faizi, R. C. Roberts and H. C. Shum, Lab on a Chip, 2015, 15, 2018-2024), the interfaces between copolymer-decorated droplets do not coalesce because the laterally overlapped monolayer of chains at the droplet interface results in repulsive steric interactions between opposing droplets. In the adhesive state, electrowetting merely causes the area of the interface to vary at constant thickness. Moreover, the process is reversible because the voltage-induced solvent expulsion establishes an osmotic pressure difference between the bulk oil and the interfacial hydrophobic region that favors driving solvent back into the membrane. Thus when the bias is reduced, the voltage-induced pressure lessens, and the compression-induced osmotic pressure causes oil to re-enter the membrane, whereupon chain swelling thickens the interface and pries apart the droplets. This behavior corresponds to traversing the disjoining pressure curve in reverse, where the osmotic pressure provides the work needed to overcome the peak. Hence, the use of voltage to drive adhesion for surfactant-coated droplets in a good solvent provides a mechanism for obtaining complete reversibility of contact between adjacent volumes.

The energetics of voltage-initiated adhesion can be quantitatively compared for CSIs in the various oils by calculating the critical disjoining pressure, $\Pi_0$, and the free energy of formation, $\Delta F$. While the free energy of formation is related to the disjoining pressure profile, as given by $$\Delta F = -\int_\infty^h \Pi(h)dh, \quad \text{Equation 16}$$

Our measurements of interfacial thickness via electrical capacitance are not sensitive to detecting changes in thickness greater than $h_c$ (i.e. prior to droplet adhesion). Thus we are unable to convert values of $\Delta F$ into disjoining pressure units for the purposes of locating the minimum point in FIG. 19B. Additionally, we make the approximation that $h_c$ and $h_e$ are close in value since our measurement of thickness represents $h_e$. The results of these calculations are presented in Table 2.

Using the mean values of threshold voltage, monolayer tension, contact angle at the threshold voltage, we find that the critical disjoining pressure varies between ~1-4 kPa for CSIs, and it increases with increasing amounts of silicone oil in the solvent and increasing equilibrium thickness. This finding suggests that more pressure is required to exclude a silicone-oil-based organic phase due to the greater solubility of the PDMS block in AR20. This finding is supported by the increased thickness that we computed for thinned interfaces in silicone oil-suggesting that more oil remains even after repulsion is overcome with voltage. For the two alkanes, we see more pressure (and higher voltage) is required to exclude decane compared to hexadecane. This trend is consistent with lipid bilayers formed in alkanes, where smaller molecule solvents tend to be retained in the membrane more due to higher solubility. The inconsistency is the fact that despite a greater barrier to adhesion (suggesting higher solubility of decane in PDMS) our thickness data (FIG. 16C) does not indicate a statistically significant difference from that measured for CSIs in hexadecane, which has a lower adhesive barrier.

The values of free energy of formation per unit area reflect the decrease in free energy gained by adopting a planar interface with reduced tension between droplets. Larger external contact angles and lower membrane tensions thus correspond to a greater percentage reduction in free energy per membrane area compared to the energy per unit area (i.e. tension) of polymer monolayers prior to forming the adhesive interface. This calculation shows that CSIs formed in silicone oil exhibit a much larger relative decrease (20-60%) in energy per unit area than those formed in alkanes (~8%), as well as that for a DPhPC DIB in hexadecane (~6%).

Our experiments also show that voltage-initiated CSIs rupture at lower electric fields compared to their lipid bilayer counterparts (FIG. 17A). Examination of the raw current measurements for all CSI/oil combinations shows that these membranes become leaky prior to rupture-which we interpret as the formation of pores in the membrane that grow unstably. In thin films, pore formation is governed by the balance of the energy required to form new pore perimeter (characterized by an edge energy) versus the energy lost due to reduction in membrane area (characterized by a lateral membrane tension). This balance is a quadratic expression in terms of pore radius, and it can be modified (I. Genco, A. Gliozzi, A. Relini, M. Robello and E. Scalas, Biochimica et Biophysica Acta (BBA)—Biomembranes, 1993, 1149, 10-18; J. C. Weaver and Y. A. Chizmadzhev, Bioelectrochemistry and Bioenergetics, 1996, 41, 135-160; A. R. Thiam, N. Bremond and J. r. m. Bibette, Physical Review Letters, 2011, 107, 068301) to include the contribution from an applied electric field, E, as given by:

$$\Delta W_p = 2\pi\Gamma r - \pi\gamma_b r^2 - \frac{1}{2}\left(\frac{\varepsilon_w}{\varepsilon_b} - 1\right)\varepsilon_b h E^2 \pi r^2, \quad \text{Equation 17}$$

where $\Delta W_p$ is the change in energy required to form a pore of radius, r, $\Gamma$ is the edge energy of the open pore, $\gamma_b$ is the lateral tension of the bilayer, $\varepsilon_w$ is the dielectric constant of water (~80), $\varepsilon_b$ is the dielectric constant of the hydrophobic region of the membrane (2), $C_m$ is the specific capacitance of the membrane, and h is the thickness of the dielectric portion of the membrane. The final grouping of terms in Equation 17 describes the reduction in energy by substituting a charged region of membrane with a charged region of water that fills an open pore (J. C. Weaver and Y.

A. Chizmadzhev, *Bioelectrochemistry and Bioenergetics*, 1996, 41, 135-160). The critical pore radius is defined at the peak of this inverted parabola, a point at which a pore will grow spontaneously. The critical pore size and the energy required to get to this size thus define the barrier for stable versus unstable pores formed in membranes.

The difference in electric field required to drive rupture for DIBs and CSIs cannot simply be due to the difference in membrane tensions (FIG. 18E), since decreasing $\gamma_b$ with respect to $\Gamma$ favors a greater barrier to unstable pore formation. Further, we do not anticipate the slightly higher dielectric permittivity of a CSI membrane over a lipid bilayer to drive this reduction in electric field at rupture. Therefore, we conclude that both 1) a lower edge energy for pores in polymeric membranes compared to a pore in a lipid bilayer and 2) the higher thicknesses of CSIs cause pore formation that leads to rupture to occur at a lower electric field. Edge energy is related to the surfactant shape and the strength of surfactant-surfactant interations. For example, it has been shown that short-chained (12 carbon), saturated PC lipids, which prefer to form micelles, exhibit lower edge energies compared to longer, saturated PCs (I. Genco, A. Gliozzi, A. Relini, M. Robello and E. Scalas, *Biochimica et Biophysica Acta (BBA)—Biomembranes*, 1993, 1149, 10-18). In contrast, the high strength of lipid-lipid interactions of the bulky DPhPC acyl chains are known to increase the energy barrier to unstable pore formation. The fact that the PEG-b-PDMS-b-PEG macromolecules are considerably longer than lipids and reside in a looped configuration at the oil-water interface suggests that they may have greater flexibility that allows them to reduce the energy of a pore edge compared tightly packed DPhPC lipids. This reduction in order should decrease their ability to resist pore formation; thus we anticipate CSIs to exhibit lower $\Gamma$ values compared to DPhPC membranes, favoring a lower electric field at rupture. In addition, our measurements proved that the dielectric thickness of CSIs (~10-20 nm) is 3-6× higher than that of DIBs (~3 nm). Both of these differences are responsible for the 2-3× lower electric field required to rupture a CSI compared to a DIB, and they are consistent with the fact that all CSIs (even ones with membrane tensions comparable to that for DPhPC DIBs (FIG. 18E) rupture at considerably lower electric field values (FIG. 17A).

Unfortunately, we are unable to make the same comparisons regarding rupture conditions to CSIs formed in pure silicone oil. Due to constraints on our test hardware, we were able only to visually monitor adhesion for these interfaces, and were thus unable to estimate specific capacitance, thickness, and rupture voltage (and electric field). While charge screening in dielectrics is believed to limit the electrowetting response at high potentials (J. Liu, M. Wang, S. Chen and M. O. Robbins, *Physical review letters*, 2012, 108, 216101; C. Quilliet and B. Berge, *Current Opinion in Colloid & Interface Science*, 2001, 6, 34-39; S. Chevalliot, S. Kuiper and J. Heikenfeld, *Journal of Adhesion Science and Technology*, 2012, 26, 1909-1930), we believe that CSIs formed in pure silicone oil are merely too thick to adequately charge or rupture. Based on measurements of CSIs formed in oils containing 25% and 50% AR20, we anticipate thin films formed in 100% AR20 to have thicknesses of >30 nm and specific capacitances of <0.001 µF/cm². According to Equations 12 and 13, lowering $C_m$ lessens the change in the wetting angle for adhesive droplets. The images in the far right column in FIG. 13 confirm this; they show that little increase in interfacial area is observed as the voltage is increased beyond the threshold value for CSIs in pure silicone oil. The higher interfacial thickness also reduces the magnitude of the electric field at a given voltage, which prevented us from being able to reach the critical electric field level required to cause rupture.

To-date planar membranes assembled from triblock copolymer membranes have utilized a combination of good and poor solvents (typically chloroform-good and decane or toluene-poor) in proportions that leave the mixture predominantly poor for the middle hydrophobic block. This selection has resulted in the spontaneous membrane thinning (D. Wong, T.-J. Jeon and J. Schmidt, *Nanotechnology*, 2006, 17, 3710; C. Nardin, M. Winterhalter and W. Meier, *Langmuir*, 2000, 16, 7708-7712). In contrast, Examples 8 and 9 showed that polymer-stabilized adhesion between droplets in a sufficiently good solvent for the middle block is pressure-dependent and completely reversible, which indicates that there is an initial energy barrier to forming an adhesive interface. We quantified this barrier in the form the minimum applied pressure achieved via electrocompression needed to remove excess oil from between opposing monolayers. The results of these measurements show that the height of the repulsive barrier to adhesion increases with increasing solubility of the hydrophobic block in the oil; thus, more voltage or mechanical pressure is required to exclude solvent. Characterizations of the thinned interface upon overcoming the barrier to adhesion show that CSIs formed in silicone oil-based solvents yield thicker membranes that also exist at a lower tension state. The demonstration of tuning this adhesion between small-volume droplets using voltage offers new capability for both connecting and disconnecting polymer-stabilized aqueous volumes, and enabling new forms of tunable modularity in droplet-based microfluidics, voltage-sensitive emulsions, and membrane-inspired material systems.

TABLE 1

Values obtained for DIBs formed at 25° C.

| Lipid Type | $C_M$ [µF/cm²] | $D_C$ [Å] | $\gamma_m$ [mN/m] * | $\gamma_m$ [mN/m] ** | $\gamma_b$ [mN/m] | $\theta_{0,eq}$ [°] | $\Delta F$ [mJ/m²] |
|---|---|---|---|---|---|---|---|
| DPhPC hexadecane | 0.652 (0.027) n = 13 | 29.9 | 1.18 (0.136) n = 8 | 1.19 (0.067) n = 3 | 2.04 (0.222) n = 8 | 29.31 (2.13) n = 116 | 0.302 |
| DPhPC, 1:1 AR20:hex | 0.667 (0.022) n = 9 | 29.2 | 1.03 (0.115) n = 4 | 1.01 (0.041) n = 3 | 1.54 (0.198) n = 4 | 41.63 (2.21) n = 37 | 0.520 |
| DPhPC, 9:1 AR20:hex | 0.701 (0.027) n = 9 | 27.8 | — | — | — | 42.15 (7.39) n = 84 | — |
| DPhPC, decane | 0.488 (0.043) n = 7 | 39.9 | 1.09 (0.095) n = 7 | — | 2.11 (0.173) n = 7 | 15.40 (1.06) n = 43 | 0.078 |

TABLE 1-continued

Values obtained for DIBs formed at 25° C.

| Lipid Type | $C_M$ [μF/cm$^2$] | $D_C$ [Å] | $\gamma_m$ [mN/m] * | $\gamma_m$ [mN/m] ** | $\gamma_b$ [mN/m] | $\theta_{0,eq}$ [°] | $\Delta F$ [mJ/m$^2$] |
|---|---|---|---|---|---|---|---|
| DPhPC, 20% Chol. hexadecane | 0.655 (0.030) n = 8 | 29.7 | 1.42 (0.051) n = 6 | 1.40 (0.111) n = 3 | 2.50 (0.095) n = 6 | 27.10 (1.65) n = 80 | 0.312 |
| DPhPC, 20% Chol. 1:1 AR20:hex | 0.713 (0.045) n = 3 | 27.3 | 1.24 (0.056) n = 4 | 1.15 (0.045) n = 3 | 1.92 (0.056) n = 4 | 38.85 (2.34) n = 128 | 0.548 |

*: DIB-electroweting/Young-Lippman method
**: Pendant drop with goniometer
: not measured
$D_C$: hydrophobic thickness, $D_C = (E_\gamma E_0)/C_M$

TABLE 2

Energetics of DIB and voltage-initiated CSI formation

| Oil type | $V_T$ (mV) | $\theta_T$ (°) | $V_m$ (mN/m) | $h_e$ (nm) | $\Pi_c (h_e)$ (kPa) | $-\Delta F (h_e)$ (mJ/m$^2$) | $\Delta F/2Y$ (% Reduction) |
|---|---|---|---|---|---|---|---|
| CSI/Hex | 83 | 24.1 | 1.32 | 0.19 | 1.20 | 0.23 | 8.1 |
| CSI/Decane | 166 | 22.0 | 1.075 | 0.22 | 0.81 | 0.16 | 7.4 |
| CSI/1:3 AR20:Hex | 179 | 38.4 | 0.114 | 0.14 | 2.42 | 0.05 | 21.9 |
| CSO 1:1 AR20:Hex | 371 | 65.8 | 0.104 | 0.12 | 3.77 | 0.12 | 57.7 |

REFERENCES

The references listed below as well as all references cited in the specification are incorporated herein by reference to the extent that they supplement, explain, provide a background for or teach methodology, techniques and/or compositions employed herein.

1. A. Petelska, M. Naumowicz and Z. Figaszewski, Cell Biochem. Biophys., 2006, 44, 205-211.
2. A. D. Petelska and Z. A. Figaszewski, Biophys. Chem., 2006, 120, 199-206.
3. A. D. Petelska, M. Naumowicz and Z. A. Figaszewski, Cell Biochem. Biophys., 2011, 61, 289-296.
4. C. Li and T. Salditt, Biophys. J., 2006, 91, 3285-3300.
5. Y. Wu, K. He, S. J. Ludtke and H. W. Huang, Biophys. J., 1995, 68, 2361-23.69.
6. R. P. Carney, T. M. Carney, M. Mueller and F. Stellacci, Biointerphases, 2012, 7, 17.
7. C. Leduc, J.-M. Jung, R. R. Carney, F. Stellacci and B. Lounis, ACS Nano, 2011, 5, 2587-2592.
8. A. Verma, O. Uzun, Y. Hu, Y. Hu, H.-S. Han, N. Watson, S. Chen, D. J. Irvine and F. Stellacci, Nat. Mater., 2008, 7, 588-595.
9. L. Ebihara, J. E. Hall, R. C. MacDonald, T. J. McIntosh and S. A. Simon, Biophysical Journal, 1979, 28, 185-196.
10. J. R. Elliott and D. A. Haydon, Biochimica et Biophysica Acta (BBA)—Biomembranes, 1984, 773, 165-168.
11. C. G. Pope, B. W. Urban and D. A. Haydon, Biochimica et Biophysica Acta (BBA)—Biomembranes, 1982, 688, 279-283.
12. J. Reyes and R. Latorre, Biophysical journal, 1979, 28, 259.
13. W.-C. Hung, M.-T. Lee, F.-Y. Chen and H. W. Huang, Biophysical Journal, 2007, 92, 3960-3967.
14. F. N. Barrera, J. Fendos and D. M. Engelman, Proceedings of the National Academy of Sciences, 2012, 109, 14422-14427.
15. J. Pan, S. Tristram-Nagle and J. F. Nagle, Physical review. E, Statistical, nonlinear, and soft matter physics, 2009, 80, 021931.
16. N. Kučerka, J. D. Perlmutter, J. Pan, S. Tristram-Nagle, J. Katsaras and J. N. Sachs, Biophysical Journal, 2008, 95, 2792-2805.
17. T. J. McIntosh, Biochimica et Biophysica Acta (BBA)—Biomembranes, 1978, 513, 43-58.
18. D. Needham and D. A. Haydon, Biophysical Journal, 1983, 41, 251-257.
19. A. D. Petelska, cent. eur. j. chem., 2012, 10, 16-26.
20. J. Requena and D. A. Haydon, Journal of Colloid and Interface Science, 1975, 51, 315-327.
21. A. R. Thiam, N. Bremond and J. Bibette, Langmuir, 2012, 28, 6291-6298.
22. M. Yanagisawa, T.-a. Yoshida, M. Furuta, S. Nakata and M. Tokita, Soft Matter, 2013, 5891-5897.
23. S. Thutupalli, S. Herminghaus and R. Seemann, Soft Matter, 2011, 7, 1312-1320.
24. S. Punnamaraju and A. J. Steckl, Langmuir, 2010, 27, 618-626.
25. S. S. Dixit, A. Pincus, B. Guo and G. W. Faris, Langmuir, 2012, 28, 7442-7451.
26. M. Naumowicz, A. D. Petelska and Z. A. Figaszewski, Electrochimica Acta, 2005, 50, 2155-2161.
27. L. C. M. Gross, A. J. Heron, S. C. Baca and M. I. Wallace, Langmuir, 2011, 27, 14335-14342.
28. A. V. Babakov, L. N. Ermishkin and E. A. Liberman, Nature, 1966, 210, 953-955.
29. T. Hanai, D. A. Haydon and J. Taylor, Journal of Theoretical Biology, 1965, 9, 433-443.
30. S. H. White, Biophysical Journal, 1970, 10, 1127-1148.
31. A. Clowes, R. Cherry and D. Chapman, Biochimica et Biophysica Acta (BBA)-Biomembranes, 1971, 249, 301-317.

32. S. H. White and T. E. Thompson, *Biochimica et Biophysica Acta (BBA)—Biomembranes*, 1973, 323, 7-22.
33. S. H. White, *Biochimica et Biophysica Acta (BBA)—Biomembranes*, 1974, 356, 8-16.
34. R. Benz, O. Fröhlich, P. Läuger and M. Montal, *Biochimica et Biophysica Acta (BBA)—Biomembranes*, 1975, 394, 323-334.
35. J. Requena, D. F. Billett and D. A. Haydon, *Proceedings of the Royal Society of London. A. Mathematical and Physical Sciences*, 1975, 347, 141-159
36. J. Requena and D. A. Haydon, *Proceedings of the Royal Society of London. A. Mathematical and Physical Sciences*, 1975, 347, 161-177.
37. D. E. Brooks, Y. K. Levine, J. Requena and D. A. Haydon, *Proceedings of the Royal Society of London. A. Mathematical and Physical Sciences*, 1975, 347, 179-194.
38. S. H. White, *Biophysical Journal*, 1975, 15, 95-117.
39. E. Bamberg and R. Benz, *Biochimica et Biophysica Acta (BBA)—Biomembranes*, 1976, 426, 570-580.
40. R. Benz and K. Janko, *Biochimica et Biophysica Acta (BBA)—Biomembranes*, 1976, 455, 721-738.
41. O. Alvarez and R. Latorre, *Biophysical Journal*, 1978, 21, 1-17.
42. S. White, *Biophysical journal*, 1978, 23, 337-347.
43. D. Bach and I. Miller, *Biophysical journal*, 1980, 29, 183.
44. T. J. McIntosh, S. A. Simon and R. C. MacDonald, *Biochimica et Biophysica Acta (BBA)—Biomembranes*, 1980, 597, 445-463.
45. J. P. Dilger, *Biochimica et Biophysica Acta (BBA)—Biomembranes*, 1981, 645, 357-363.
46. H. Bayley, B. Cronin, A. Heron, M. A. Holden, W. L. Hwang, R. Syeda, J. Thompson and M. Wallace, *Molecular BioSystems*, 2008, 4, 1191-1208.
47. G. Villar, A. J. Heron and H. Bayley, *Nat Nano*, 2011, 6, 803-808.
48. G. Villar, A. D. Graham and H. Bayley, *Science*, 2013, 340, 48-52.
49. N. Malmstadt, M. A. Nash, R. F. Purnell and J. J. Schmidt, *Nano letters*, 2006, 6, 1961-1965.
50. J. Poulos, S. Portonovo, H. Bang and J. Schmidt, *Journal of Physics: Condensed Matter*, 2010, 22, 454105.
51. J. L. Poulos, T.-J. Jeon, R. Damoiseaux, E. J. Gillespie, K. A. Bradley and J. J. Schmidt, *Biosensors and Bioelectronics*, 2009, 24, 1806-1810.
52. J. L. Poulos, W. C. Nelson, T.-J. Jeon, C.-J. C. Kim and J. J. Schmidt, *Applied Physics Letters*, 2009, 95
53. T. Thapliyal, J. L. Poulos and J. J. Schmidt, *Biosensors and Bioelectronics*, 2011, 26, 2651-2654.
54. S. A. Sarles and D. J. Leo, *Analytical Chemistry*, 2010, 82, 959-966.
55. L. C. M. Gross, O. K. Castell and M. I. Wallace, *Nano Letters*, 2011, 11, 3324-3328.
56. G. J. Taylor and S. A. Sarles, *Langmuir*, 2015, 31, 325-337.
57. W. L. Hwang, M. Chen, B. d. Cronin, M. A. Holden and H. Bayley, *Journal of the American Chemical Society*, 2008, 130, 5878-5879.
58. M. A. Holden, D. Needham and H. Bayley, *Journal of the American Chemical Society*, 2007, 129, 8650-8655.
59. W. L. Hwang, M. A. Holden, S. White and H. Bayley, *Journal of the American Chemical Society*, 2007, 129, 11854-11864.
60. Y. Elani, R. V. Law and O. Ces, *Nat Commun*, 2014, 5.
61. Y. Elani, R. V. Law and O. Ces, *Physical Chemistry Chemical Physics*, 2015, 17, 15534-15537.
62. A. J. Heron, J. R. Thompson, A. E. Mason and M. I. Wallace, *Journal of the American Chemical Society*, 2007, 129, 16042-16047.
63. A. Fischer, M. A. Holden, B. L. Pentelute and R. J. Collier, *Proceedings of the National Academy of Sciences*, 2011, 108, 16577-16581.
64. J. B. Boreyko, G. Polizos, P. G. Datskos, S. A. Sarles and C. P. Collier, *Proceedings of the National Academy of Sciences*, 2014, 111, 7588-7593.
65. N. Stuurman, A. D. Edelstein, N. Amodaj, K. H. Hoover and R. D. Vale, *Current protocols in molecular biology/edited by Frederick M. Ausubel . . . [et al.]*, 2010, Unit14.20.
66. A. R. Thiam, N. Bremond and J. Bibette, *Physical review letters*, 2011, 107, 068301.
67. A. D. Petelska and Z. A. Figaszewski, *Bioelectrochemistry and Bioenergetics*, 1998, 46, 199-204.
68. R. Shamai, D. Andelman, B. Berge and R. Hayes, *Soft Matter*, 2008, 4, 38-45.
69. S. Chevalliot, S. Kuiper and J. Heikenfeld, *Journal of Adhesion Science and Technology*, 2012, 26, 1909-1930.
70. F. Mugele and J.-C. Baret, *Journal of Physics: Condensed Matter*, 2005, 17, R705.
71. A. Quinn, R. Sedev and J. Ralston, *The Journal of Physical Chemistry B*, 2005, 109, 6268-6275.
72. J. C. Weaver and Y. A. Chizmadzhev, *Bioelectrochemistry and Bioenergetics*, 1996, 41, 135-160.
73. S. White and W. Chang, *Biophysical journal*, 1981, 36, 449.
74. J. Requena, D. A. Haydon and S. B. Hladky, *Biophysical Journal*, 1975, 15, 77-81.
75. S. Punnamaraju, H. You and A. J. Steckl, *Langmuir*, 2012, 28, 7657-7664.
76. G. Valincius, F. Heinrich, R. Budvytyte, D. J. Vanderah, D. J. McGillivray, Y. Sokolov, J. E. Hall and M. Losche, *Biophysical Journal*, 2008, 95, 4845-4861.
77. P. Poulin and J. Bibette, *Langmuir*, 1998, 14, 6341-6343.
78. E. Baykal-Caglar, E. Hassan-Zadeh, B. Saremi and J. Huang, *Biochimica et Biophysica Acta (BBA)—Biomembranes*, 2012, 1818, 2598-2604.
79. C. Karolis, H. G. L. Coster, T. C. Chilcott and K. D. Barrow, *Biochimica et Biophysica Acta (BBA)—Biomembranes*, 1998, 1368, 247-255.
80. T. P. W. McMullen, R. N. A. H. Lewis and R. N. McElhaney, *Biochemistry*, 1993, 32, 516-522.
81. S. Chiu, E. Jakobsson, R. J. Mashl and H. L. Scott, *Biophysical Journal*, 2002, 83, 1842-1853.
82. Y. Suzuki, *Journal of lipid research*, 1982, 23, 62-69.
83. I. W. Levin, E. Keihn and W. C. Harris, *Biochimica et Biophysica Acta (BBA)-Biomembranes*, 1985, 820, 40-47

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of determining a plurality of physical properties of an artificial cellular membrane, wherein the method comprises:
    (a) preparing an artificial cellular membrane comprising a bilayer of amphiphilic molecules at an interface between a first droplet and a second droplet, wherein the first and second droplets each comprise an aqueous solution, wherein the first droplet is attached to a first electrode and the second droplet is attached to second electrode, and wherein the first and second droplets are suspended in a hydrophobic liquid medium;

(b) determining a specific capacitance of the artificial cellular membrane, wherein the determining comprises determining a nominal capacitance and an artificial cellular membrane area for the artificial cellular membrane at each of a plurality of artificial cellular membrane areas, wherein the area of the artificial cellular membrane is varied by changing the position of the first or second droplet relative to the other of the first or second droplet, and wherein the specific capacitance is calculated from the nominal capacitance and artificial cellular membrane area data, optionally from the slope of a linear least squares regression of nominal capacitance versus area data; and (c) determining an artificial cellular membrane tension, wherein the determining comprises fixing the positions of the first and the second droplets relative to each other, measuring a contact angle between the droplets at a plurality of applied bias voltages, and calculating monolayer tension and bilayer tension.

2. The method of claim 1, wherein the plurality of physical properties comprise specific capacitance, monolayer tension, and bilayer tension.

3. The method of claim 1, wherein the method further comprises determining one or more of membrane thickness, free energy of formation, and a parameter that describes electrowetting behavior, optionally alpha, beta, and/or B coefficients.

4. The method of claim 1, wherein the amphiphilic molecules are selected from the group consisting of a lipid, an amphiphilic polymer, a biological membrane extract, and a mixture thereof.

5. The method of claim 4, wherein the aqueous solution further comprises one or more of the group consisting of a small molecule, a peptide, a protein, a biomolecule, and a pharmaceutically active agent.

6. The method of claim 1, wherein the amphiphilic molecules comprise a lipid or lipid mixture selected from the group consisting of a fatty acyl, a glycerolipid, a glycerophospholipid, a shingolipid, a sterol lipid, a prenol lipid, a saccharolipid, a polyketide, a phospholipid, a fluorescent lipid, a glycolipid, cholesterol, a biological membrane extract, and a mixture thereof.

7. The method of claim 6, wherein the amphiphilic molecules comprise one or more of the group consisting of 1,2-diphytanoyl-sn-glycero-3-phosphocholine (DPhPC), 1,2-dioleoyl-sn-glycero-3-phosphocholine (DOPC), palmitoyl oleoyl phosphatidylcholine (POPC), 1-palmitoyl-2-oleoyl-phosphatidylethanolamine (POPE), 1-palmitoyl-2-oleoylphosphatidylglycerol (POPG), 1,2-di-O-phytanyl-sn-glycero-3-phosphocholine (DoPhPC), dipalmitoyl phosphaditdylcholine (DPPC), 1,2-dioleoyl-sn-glycero-3-phosphoglycerol (DOPG), 1,2-distearoyl-sn-glycero-3-phosphocholine (DSPC), diphytanoyl phosphatidylglycerol (DPhPG), diphytanoyl phosphatidylserine (DPhPS), 1,2-dioleoyl-sn-glycero-3-phophoserine (DOPS), 1,2-dipalmitoyl-sn-glycero-3-phosphoserine (DPPS), 1,2-dipalmitoyl-sn-glycero-3-phosphoethanolamine (DPPE), Rhodamine-DPPE, 1,2-dipalmitoyl-sn-glycero-3-phosphoethanolamine-N-(7-nitro-2-1,3-benzoxadiazol-4-yl) (NDB-DPPE), and cholesterol.

8. The method of claim 1, wherein the hydrophobic liquid medium comprises a natural oil, an alkane, an alkene, a fluorocarbon, a silicone oil, a hydrophobic polymer, an amphiphilic polymer, a wax, or a mixture thereof.

9. The method of claim 8, wherein the hydrophobic liquid medium is one or more of the group consisting of n-hexadecane, heptadecane, tetradecane, squalene, dodecane, silicone oil, decane and mixtures thereof.

10. The method of claim 1, wherein the hydrophobic liquid medium is contained in a transparent chamber, wherein a side of said chamber, optionally a top side of the chamber, is completely or partially open to receive the electrodes, further optionally wherein the transparent chamber comprises or consists of polydimethylsiloxane (PDMS), glass, acrylic or rubber.

11. The method of claim 1, wherein a microscope and/or camera is positioned to obtain optical images of the artificial cellular membrane.

12. The method of claim 1, wherein the first electrode and the second electrode are coated with one of the group consisting of a hydrogel, agarose, polyacrylamide, nitrocellulose, cellulose acetate, glass, mesoporous silica, cross-linked polyethylene glycol, a chemically linked layer of biomolecules, proteins, or other species to provide a hydrophilic surface, and a patterned or textured surface created to display a desired wetting property.

13. The method of claim 1, wherein the first and second electrode each comprise silver/silver chloride.

14. The method of claim 1, wherein at least one of the first and the second electrodes is attached to a micromanipulator.

15. The method of claim 14, wherein a three-axis micromanipulator is attached to each of the first electrode and the second electrode, and the positioning of the first and/or second droplets is performed using one or more of the micromanipulators.

16. The method of claim 1, wherein the first and second droplets each have a volume of between about 10 nanoliters (nL) and about 1000 nL, optionally between about 200 nanoliters and about 500 nanoliters.

17. The method of claim 16, wherein the first and second droplets each have a volume of about 300 nL.

18. The method of claim 1, wherein the preparing of step (a) comprises: (i) preparing the aqueous solution, wherein the aqueous solution comprises an amphiphilic molecule or mixture of amphiphilic molecules; (ii) attaching the first droplet of the aqueous solution to a tip of the first electrode and attaching the second droplet of the aqueous solution to a tip of the second electrode; (iii) suspending the first and second droplets in the hydrophobic liquid medium; and (iv) moving the first and/or second electrode to position the first and second droplets relative to one another to form an interface between the first and second droplets.

19. The method of claim 18, wherein the amphiphilic molecule or mixture of amphiphilic molecules comprises an amphiphilic polymer, optionally an ABA block copolymer, and wherein step (iv) further comprises applying a voltage.

20. The method of claim 1, wherein the determining of a nominal capacitance and an artificial cellular membrane area at each of a plurality of artificial cellular membrane areas in step (b) comprises: (v) moving the first and/or second electrode to change the relative position of the first and second droplets and thus the artificial cellular membrane area; (vi) waiting for the nominal capacitance to stabilize, optionally wherein the waiting is for between about 30 seconds and about 60 seconds; (vii) recording the nominal capacitance and acquiring an optical image of the artificial cellular membrane; (viii) calculating the area of the artificial cellular membrane using data from the optical image; and (ix) repeating steps (v)-(viii) one or more times, optionally four times, prior to calculating the specific capacitance.

21. The method of claim 1, wherein the contact angle between droplets at each of the plurality of applied bias voltages is measured using an optical image of the droplets taken during the application of each of the applied bias voltages.

22. The method of claim 1, wherein calculating the monolayer tension comprises determining the slope of a linear least squares regression of a plot of the change in the cosine of the contact angle as a function of voltage squared and using the slope and the specific capacitance determined in step (b) to determine monolayer tension using the Young-Lippmann equation.

23. The method of claim 1, wherein calculating the bilayer tension comprises using the Young-Dupre equation.

24. A method of determining the effect of a change in the chemical composition of an artificial cellular membrane, wherein the method comprises:
   (a) preparing an artificial cellular membrane at an interface between a first droplet and a second droplet of a first aqueous solution wherein the first aqueous solution comprises an amphiphilic molecule or mixture of amphiphilic molecules, and wherein the first droplet and the second droplet are each attached to separate electrodes and suspended in a hydrophobic liquid medium;
   (b) determining specific capacitance of the artificial cellular membrane, wherein the determining comprises determining a nominal capacitance and an artificial cellular membrane area at each of a plurality of artificial cellular membrane areas, wherein artificial cellular membrane area is varied by changing the position of the first or second droplet relative to the other of the first and second droplets, and optionally wherein the specific capacitance is calculated from the slope of a linear least squares regression of the nominal capacitance versus area data;
   (c) determining an artificial cellular membrane tension, wherein the determining comprises fixing the positions of the first and the second droplets relative to each other, measuring the contact angle of the droplets at a plurality of applied bias voltages, and calculating the monolayer and bilayer tension;
   (d) repeating steps (b)-(c) for an artificial membrane formed at the interface of a first and a second droplet of a second aqueous solution, wherein the second aqueous solution comprises an amphiphilic molecule or molecules, and wherein the chemical composition of the second aqueous solution differs from the chemical composition of first aqueous solution, and wherein the first and the second droplet of the second aqueous solution are each attached to separate electrodes and suspended in a hydrophobic liquid medium; and
   (e) comparing the data obtained in for the artificial cellular membrane formed with droplets of the first aqueous solution to that obtained for the artificial membrane formed with droplets of the second aqueous solution, thereby determining the effect of a change in chemical composition of the artificial cellular membrane.

25. The method of claim 24, wherein the second aqueous solution comprises a small molecule, peptide, protein, biomolecule, or pharmaceutically active agent that may or may not be present in the first aqueous solution, and wherein the method determines the effect of the small molecule, peptide, protein, biomolecule, or pharmaceutically active agent on the artificial cellular membrane.

26. The method of claim 25, wherein the second aqueous solution comprises a small molecule or pharmaceutically active agent, wherein the pharmaceutically active agent is an anesthetic or model anesthetic, optionally lidocaine or ethanol.

* * * * *